United States Patent [19]
Wong et al.

[11] Patent Number: 5,962,660
[45] Date of Patent: Oct. 5, 1999

[54] SIALYL LEWIS X MIMETICS INCORPORATING FUCOPEPTIDES

[75] Inventors: Chi-Huey Wong, Rancho Santa Fe; Chun-Cheng Lin, San Diego, both of Calif.; Tetsuya Kajimoto, Wako, Japan

[73] Assignee: The Scripps Research Institute, La Jolla, Calif.

[21] Appl. No.: 08/933,775

[22] Filed: Sep. 19, 1997

Related U.S. Application Data

[63] Continuation-in-part of application No. PCT/EP96/01244, Mar. 21, 1996, which is a continuation-in-part of application No. 08/519,203, Aug. 25, 1995, Pat. No. 5,614,615, which is a continuation-in-part of application No. 08/407,912, Mar. 21, 1995, Pat. No. 5,599,915.

[51] Int. Cl.$^6$ .................................................. C07H 15/00
[52] U.S. Cl. .................. 536/17.9; 536/4.1; 536/18.7; 514/23; 530/322; 548/535
[58] Field of Search .................................. 536/4.1, 17.9; 514/23; 530/322; 548/535

[56] References Cited

U.S. PATENT DOCUMENTS

| | | | |
|---|---|---|---|
| 5,079,353 | 1/1992 | Ratcliffe | 536/53 |
| 5,143,712 | 9/1992 | Brandley | 424/1.1 |
| 5,296,594 | 3/1994 | Ratcliffe | 536/53 |
| 5,599,915 | 2/1997 | Wong | 536/18.7 |
| 5,614,615 | 3/1997 | Wong | 536/17.9 |

FOREIGN PATENT DOCUMENTS

| | | |
|---|---|---|
| WO91/19501 | 12/1991 | WIPO . |
| WO91/19502 | 12/1991 | WIPO . |
| 9629339 | 9/1996 | WIPO . |

OTHER PUBLICATIONS

Allanson, et al., "A Novel Mimic of the Sialyl Lewis X Determinant" *Tetrahedron Lett.,* 34: 3945–3948 (1993).

Ball, et al., "Synthesis and Structural Analysis Using 2–D NMR of Sialyl Lewis X (Sle) and Lewis X (Le) Oligosaccharides: Ligands Related to E–Selectin (ELAM–1) Binding", *J. Am. Chem. Soc.,* 114: 5449–5451 (1992).

Brandley, et al., "Structure–Function Studies on Selectin Carbohydrate Ligands. Modifications to Fucose, Sialic Acid and Sulphate as a Sialic Acid Replacement", *Glycobiology,* 3:633–639 (1993).

DeFrees, et al., "Ligand Recognition by E–Selectin: Analysis of Conformation and Activity of Synthetic Monomeric and Bivalent Sialyl Lewis X Analogs", *J. Am. Chem. Soc.,* 115: 7549–7550 (1993).

DeFrees, et al., "Ligand Recognition by E–Selectin: Synthesis, Inhibitory Activity, and Conformational Analysis of Bivalent Sialyl Lewis X Analogs", *J. Am. Chem. Soc.,* 117: 66–79 (1995).

Giannis, "The Sialyl Lewis X Group and its Analogues as Ligands for Selectins: Chemoenzymatic Synthesis and Biological Functions", *Angew. Chem. Int. Ed. Engl.* 33: 178–180 (1994).

Graves, et al., "Insight into E–Selectin/Ligand Interaction from the Crystal Structure and Mutagenesis of the Iec/EGF Domains", *Nature,* 367: 532–538 (1994).

Hanessian, et al., "A Novel Asymmetric Synthesis of Alpha–and Beta–Amino Aryl Phosphonic Acids", *Synlett,* 868:35–36 (1993).

Huang, et al., "Synthesis of Biologically Active Sialyl Lewis X Mimetics", *J. Org. Chem.,* 60: 3100–3106 (1995).

Ichikawa, et al., "Chemical Enzymatic Synthesis and Conformational Analysis of Sialyl Lewis X and Derivatives", *J. Am. Chem. Soc.,* 114: 9283–9298 (1992).

Lin, et al., "Conformational Studies of Sialyl Lewis X in Aqueous Solution", *J. Am. Chem. Soc.,* 114: 5452–5454 (1992).

Mulligan, et al., "Protective Effects of Oligosaccharides in P–Selectin–Dependent Lung Injury", *Nature,* 364: 149–151 (1993).

Narasinga Rao, et al., "Sialyl Lewis X Mimics Derived from a Pharmacophore Search are Selectin Inhibitors with Anti-Inflammatory Activity", *J. Biol. Chem.,* 269: 19663–19666 (1994).

Nelson, et al., "Higher–Affinity Oligosaccharide Ligands for E–Selectin", *J. Clin. Invest.,* 91: 1157–1166 (1993).

Prodger, et al., "Synthesis of a Novel Analogue of Sialyl Lewis X", *Tetrahedron Lett.,* 36: 2339–2342 (1995).

Ragan, et al., Synthesis of a Galactose–Fucose Disaccharide Mimic of Sialyl Lewis X, *Bioorganic Med. Chem. Lett.,* 4: 2563–2566 (1994).

Ramphal, et al., "Structure–Activity Relationships of Sialyl Lewis–X–Containing Oligosaccharides. 1. Effect of Modifications of the Fucose Moiety" *J. Med. Chem.,* 37: 3459–3463 (1994).

Tyrrell, et al., "Structural Requirements for the Carbohydrate Ligand of E–Selectin", *Proc. Natl. Acad. Sci., USA,* 88: 10372–10376 (1991).

Uchiyama, et. al., "Design and Synthesis of Sialyl Lewis X Mimetics", *J. Am. Chem. Soc.,* 117: 5395–5396 (1995).

Wu, et al, "Synthesis of Fucopeptides as Sialyl Lewis X Mimetics" *Angew. Chem. Int. Ed. Engl.,* 35(1):88–90 (1996).

*Primary Examiner*—Cecilia J. Tsang
*Assistant Examiner*—David Lukton
*Attorney, Agent, or Firm*—Donald G. Lewis

[57] ABSTRACT

Sialyl Lewis X mimetics incorporating fucopeptides are synthesized and shown to mimic the configuration and essential functional groups of sialyl Lewis X in space. The fucopeptides exhibit substantially the same biological activity as sialyl Lewis X in the E-selectin binding assay and can be employed for blocking neutrophil inflamatory conditions.

8 Claims, 18 Drawing Sheets

| Amine | Coupling Method | R | n | X | Final Compounds | Yield |
|---|---|---|---|---|---|---|
| 250 | A | (HO, PO-CH<) | 1 | H | 2000 | 52% |
| 250 | B | | 2 | H | 3000 | 50% |
| 250 | C | | 1 | NH$_2$ | 4000 | 65% |
| 260 | A | (HO, PO-(CH)$_2$) | 1 | H | 5000 | 49% |
| 260 | B | | 2 | H | 6000 | 56% |
| 260 | C | | 1 | NH$_2$ | 7000 | 49% |
| 270 | A | (HO, PO-(CH)$_3$) | 1 | H | 8000 | 65% |
| 270 | B | | 2 | H | 9000 | 63% |
| 270 | C | | 1 | NH$_2$ | 1000 | 50% |
| 280 | D | (PO, PO) | 1 | H | 1100 | 68% |
| 280 | E | | 2 | H | 1200 | 53% |
| 290 | F | (PO, HO) | 1 | H | 1300 | 45% |
| 290 | G | | 2 | H | 1400 | 29% |

| Structure | m | n | X | Final Compounds | IC$_{50}$ |
|---|---|---|---|---|---|
| | 1 | 1 | H | 2000 | 10 mM[2] |
| | 1 | 2 | H | 3000 | 10 mM[2] |
| | 1 | 1 | NH$_2$ | 4000 | 0.6 mM[2] |
| | 2 | 1 | H | 5000 | inactive[1] |
| | 2 | 2 | H | 6000 | 4.2 mM[1] |
| | 2 | 1 | NH$_2$ | 7000 | 1 mM[1] |
| | 3 | 1 | H | 8000 | 1 mM[1] |
| | 3 | 1 | H | 8000a | 1 mM[3] |
| | 3 | 1 | H | 8000b | 1 mM[3] |
| | 3 | 2 | H | 9000 | inactive |
| | 3 | 1 | NH$_2$ | 1000 | 1.5 mM[3] |

| Structure | n | Final Compounds | IC$_{50}$ |
|---|---|---|---|
| (structure with n) | 1 | 1100 | inactive |
| | 2 | 1200 | 0.3 mM |
| (structure with n) | 1 | 1300 | 0.3 mM |
| | 2 | 1400 | 0.2 mM |

FIG. 17

SIALYL LEWIS X MIMETICS INCORPORATING FUCOPEPTIDES

CROSS-REFERENCE TO RELATED APPLICATION

This application is a continuation-in-part of PCT/EP96/01244, filed Mar. 21, 1996, now WO 96/29339 which is a continuation-in-part of application Ser. No. 08/519,203, filed Aug. 25, 1995, now U.S. Pat. No. 5,614,615, which is a continuation in part of application Ser. No. 08/407,912, filed Mar. 21, 1995, now U.S. Pat. No. 5,599,915.

STATEMENT OF GOVERNMENT RIGHTS

This invention was made with government support under Grant No. CHE-9310081 awarded by the National Science Foundation. The U.S. government has certain rights in the invention.

TECHNICAL FIELD

The present invention relates to compounds that inhibit cellular adhesion. More particularly, the present invention relates to Sialyl Lewis X mimetics which incorporate fucopeptides and which mimic the inhibition of selectin-mediated cellular adhesion by Sialyl Lewis X.

BACKGROUND

Sialyl Lewis X (SLe$^x$) is a cell surface carbohydrate ligand found on neutrophils, anchored onto the outer membrane thereof by integral membrane glycoproteins and/or glycolipids. SLe$^x$ mediates binding of neutrophils to vascular endothelial cells by binding to E-selectin. (M. Phillips, et al.,. Science. 1990, 250, 1130.; J. Lowe, et al, Cell. 1990, 63, 475; T. Feizi, Trends. Biochem. Sci. 1991, 16, 84; M. Tiemeyer., et al., Proc. Natl. Acad. Sci. U.S.A. 1991, 88, 1138; L. Lasky. Science. 1992, 258, 964; and T. Springer, L. A. Lasky, Nature 1991, 349, 196.) E-selectin is a cell surface protein inducibly expressed in endothelial cells in response to inflammatory factors such as interleukin Iβ(IL-Iβ) and tumor necrosis factor α(TNFα), leukotriene B$_4$, neurotoxins and bacterial endotoxins, e.g., lipopolysaccharides. These compounds augment polymorphonuclear leukocyte (neutrophil), and monocyte adhesion. Binding of neutrophils to endothelial cells is observed at an early stage after tissue injury and is associated with various acute and chronic inflammations. Neutrophil-mediated inflammatory diseases may be treated by administration of sLe$^x$. Administration of sLe$^x$ inhibits the sLe$^x$/E-selectin interaction and blocks adhesion of neutophils to endothelial cells. (M. Buerke, et al., J. Clin. Invest., 1994, 1140.)

In addition to binding to neutrophils, vascular endothelial cells play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Specialized cell surface receptors on endothelial cells and platelets, designated E-selectin (endothelial leukocyte adhesion molecule-1; ELAM-1) and P-selectin (granule membrane protein-140; GMP-140), respectively, are involved in the recognition of various circulating cells by the endothelium and platelets. For example, E-selectin has been shown to mediate endothelial leukocyte adhesion, which is the first step in many inflammatory responses. Specifically, E-selectin binds human neutrophils, monocytes, eosinophils, certain T-lymphocytes, NK cells, and the pro-myelocytic cell line HL-60.

P-selectin (also known as GMP-140 and PADGEM) is present on the surface of platelets and endothelial cells, where it mediates platelet-leukocyte and endothelium-leukocyte interactions. Thus, for example, activated platelets that express P-selectin on their surface are known to bind to monocytes and neutrophils, and also to bind monocyte-like cell lines, e.g., HL-60 and U937.

P-selectin is an alpha granule membrane protein of molecular mass 140,000 that is expressed on the surface of activated platelets upon platelet stimulation and granule secretion. It is also found in megakaryocytes within the Weibel-Palade bodies. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin). In addition to lymphocyte homing, MEL-14 antigen/LAM-1 is believed to function early in neutrophil binding to the endothelium.

The term "selectin" has been suggested for a general class of receptors, which includes E-selectin (ELAM-1), P-selectin (GMP-140) and L-selectin (MEL-14), because of their lectin-like domain and the selective nature of their adhesive functions. The structure and function of selectin receptors has been elucidated by cloning and expression of full length cDNA encoding each of the above receptors.

The extracellular portion of selectins can be divided into three segments based on homologies to previously described proteins. The N-terminal region (about 120 amino acids) is related to the C-type mammalian lectin protein family as described by Drickamer, J. Biol. Chem., 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

U.S. Pat. No. 5,079,353 and its divisional Patent No. 5,296,594 teach the synthesis and use of the sialyl Lewis X (sialyl Le$^X$ or SLe$^x$) and sialyl Lewis A (sialyl Le$^a$ or Sle$^a$) antigens that are present in cancerous tissues, and are ligands for the before-described selectin receptors. U.S. Pat. No. 5,143,712 teaches the binding interactions between various receptors such as ELAM-1 (E-selectin) and ligands such as sialyl Le$^X$ as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe$^x$.

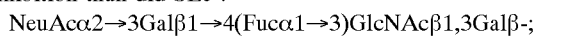
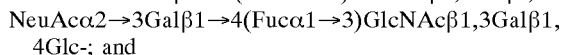
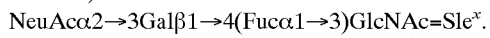

Mulligan et al., *Nature*, 364; 149–151 (1993) reported upon the in vivo effects of Sle$^x$ and a pentamer such as that above present as a —O(CH$_2$)$_5$CO$_2$CH$_3$ glycoside in a neutrophil/P-selection-dependent rat model. Those authors found that intravenous infusion of up to 200 μg of SLe$^x$ or the pentamer dramatically reduced lung injury and diminished tissue accumulation of neutrophils in rats that received an intravenous infusion of cobra venom. Based on the concentrations used, 200 μg, the effective intravenous concentration of SLe$^x$ was calculated to be less than 1 μM.

DeFrees etal., *J. Am. Chem. Soc.*, 117:66–79 (1995) reported on the in vitro inhibition of binding between E-selectin and SLe$^x$-bearing HL-60 cells for a number of SLe$^x$-related materials including SLe$^x$ itself, an ethyl glycoside of the above pentamer and a number of bivalent SLe$^x$ analogs. Those authors noted that although the affinity of SLe$^x$ for E-selectin is relatively weak in vitro, the IC$_{50}$ value in vivo for protecting against lung injury in rats was in the 1 μM range.

Although SLe$^x$ has been considered to be potentially useful as anti-inflammatory agent and its synthesis on large scales has been developed for clinical evaluation, this natural saccharide can only be used as an injectable form in cases presenting with acute symptoms as it is orally inactive and unstable in the blood stream, because of glycosidase reductions.

The search for novel SLe$^x$ mimetics with simpler structure, higher affinity for the receptor, and better stability against glycosidases, especially fucosidase and sialidase, has been of current interest. A sLe$^X$ mimetic is a compound which includes the functional groups of sLe$^X$ and which mimics the active conformation of sLe$^x$ in space, but which lacks one or more of the glycosidic bonds of sLe$^X$ and/or one or more of the saccharide subunits or analogs thereof. Several active sLe$^X$ mimetics and sLe$^X$ analogs have been designed and synthesized, e.g., a) Allanson, et al., *Tetrahedron Lett*, 34:3945 (1993), 3945 (30-fold less active than SLe$^x$); b) Ragan, et al., *Bioorg. Med. Chem. Lett*, 4:2563 (1994) (a mixture of 4 diastereomers with 40- to 50-fold less activity); c) Hanessian, et al., *Synlett*, 868 (1993) (inactive); and d) H. Huang and C.-H. Wong. *J. Org. Chem.* 1995, 60, 3100; J. C. Prodger, et al. *Tetrahedron Lett.* 1995, 36, 2339; and B. N. Narasinga Rao,. *J. Biol. Chem.* 1994, 269, 19663. Two sLe$^X$ mimetics synthesized by Uchiyama et al. are of particular note because they exhibit activities similar to sLe$^x$ in the E-selectin binding assay. (T. Uchiyama, et al. *J. Am. Chem. Soc.* 1995, 117, 5395.) For active natural products inhibiting E-selectin, see Narasinga Rao, et al., *J. Biol. Chem.*, 269:19663 (1994).

The key structural features of sLe$^x$ required for recognition by E-selectin have been determined by structural and conformational studies and by comparative studies of the blocking activity of sLe$^x$ analog families. (B. Brandley, *Glycobiology* 1993, 3, 633; S. DeFrees, *J. Am. Chem. Soc.* 1993, 115, 7549; J. Ramphal, *J. Med. Chem.* 1994, 37, 3459; D. Tyrrell, *Proc. Natl. Acad. Sci. USA* 1991, 88, 10372; R. Nelson, *J. Clin. Invest.* 1993, 91, 1157; and A. Giannis, *Angew. Chem. Int. Ed. Engl.* 1994. 33. 178.) The solution conformation of sLe$^x$ has been characterized using physical methodologies. (Y. C. Lin, et al., *J. Am. Chem. Soc.* 1992, 114, 5452; Y. Ichikawa, et al. *J. Am. Chem. Soc.*, 1992, 114, 9283; and G. E. Ball et al., *J. Am. Chem. Soc.*, 1992, 114, 5449.) The three-dimensional structure of the human E-selectin has been characterized by X-ray diffraction. (B. J. Graves, et al., *Nature,* 1994, 367, 532.) It has been found that the L-fucose, D-galactose (Gal) and sialic acid moieties of sLe$^x$ are the major components that interact with E-selectin. N-acetylglucosamine unit appears to act merely as a linker to connect L-fucose and sialyl galactose. The six functional groups of sLe$^x$ molecule including the 2-, 3- and 4-OH groups of L-fucose, the 4- and 6-OH groups of Gal and the —CO$_2$— group of sialic acid are essential for E-selectin recognition, as illustrated in FIG. 1.

Although sLe$^x$ and active sLe$^x$ analogs can be employed as anti-inflammatory agents, these tetrasaccharides can only be used in acute symptoms as they are unstable in the blood and orally inactive. In addition, it is generally difficult to synthesize oligosaccharides on a large-scale. The use of sLe$^X$ mimetics can obviate the above problems associated with sLe$^X$ analogs. Unfortunately, sLe$^X$ mimetics generally have low activity. What are needed are sLe$^x$ mimetics which are more stable as compared to sLe$^x$ and sLe$^x$ analogs; which possess better bioavailability as compared to sLe$^x$ and sLe$^x$ analogs; which are easier to synthesize than sLe$^x$ and sLe$^x$ analogs; and which exhibit greater activity as compared to known sLe$^X$ mimetics.

SUMMARY OF THE INVENTION

The invention is directed to SLeX mimetics. More specifically, the invention is directed to compounds of formula I:

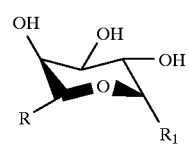

wherein
i) R is CH$_3$, and either
R$_1$ is a radical of formulae (a$_1$) or (a$_2$)

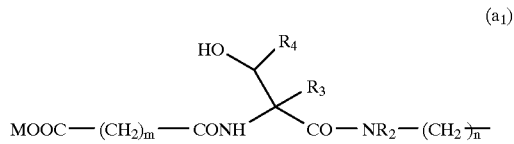

-continued

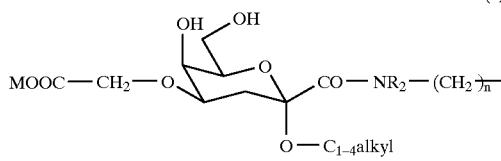 (a₂)

wherein m is 2 or 3;

n is 2 or 3;

M is a cation;

$R_2$ is H or a saturated or unsaturated hydrocarbon residue with up to 20 carbon atoms, optionally bearing in ω position a formyl or a $C_{1-4}$ alcohol acetal or $C_{2-4}$ diol acetal group;

$R_3$ is H, —$CH_2OH$ or —$CH_2CH_2OH$; and $R_4$ is H, $C_{1-4}$alkyl, —$CH_2OH$, —$CH_2CH_2OH$ or —$CH_2CH_2CH_2OH$ with the provisos that
1) one of $R_3$ and $R_4$ is H, and
2) when $R_4$ is H, $R_3$ is —$CH_2OH$ or —$CH_2CH_2OH$, and
3) when $R_3$ is H, $R_4$ is $CH_3$, —$CH_2OH$, —$CH_2CH_2OH$ or —$CH_2CH_2CH_2OH$;

or $R_1$ is a radical of formula (b)

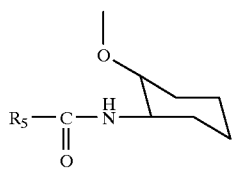 (b)

wherein $R_5$ is

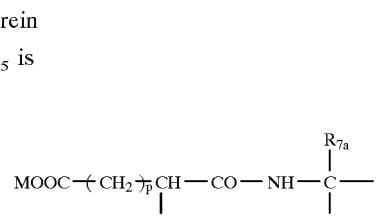 (b₁)

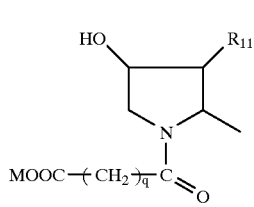 (b₂)

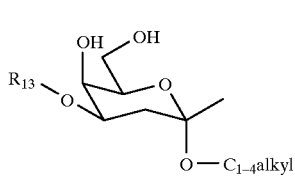 (b₃)

or

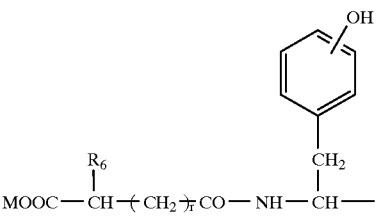 (b₄)

wherein p is 1 or 2;

q is 2 or 3;

r is 1 or 2;

$R_6$ is H, $NH_2$ or —$NHR_x$ wherein $R_x$ is an amino protecting group;

$R_{7a}$ is —$CH_2OH$, —$CH_2CH_2OH$ or —$CH(OH)$—$CH_2OH$ and $R_{7b}$ is H or each of $R_{7a}$ and $R_{7b}$ is $CH_2OH$;

$R_{11}$ is H or —OH;

$R_{13}$ is —$(CH_2)_j$—COOM or —$SO_3M$ wherein j is 1, 2 or 3; and

M is as defined above;

or $R_1$ is a radical of formula (c)

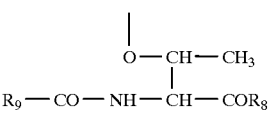 (c)

wherein $R_8$ is $OM_1$, $OR_{14}$, $R_s$-$R_p$ or —$NHR_y$ wherein $M_1$ is a cation, $R_{14}$ is a saturated or unsaturated hydrocarbon residue, $R_s$ is a spacer group, $R_p$ is a phosphatidyl residue and $R_y$ is a saturated or unsaturated lipophilic residue; and $R_9$ is

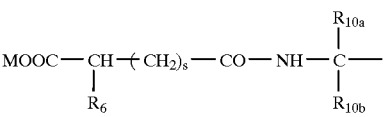 (c₁)

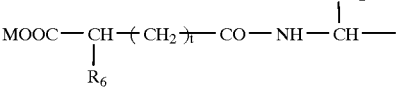 (c₂)

-continued

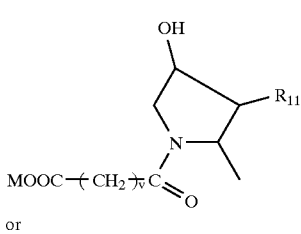

or

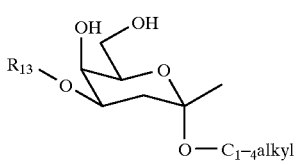

wherein
s is 1 or 2;
t is 1 or 2;
v is 2 or 3;
M, $R_6$, $R_{11}$ and $R_{13}$ are as defined above; and
$R_{10a}$ is —$CH_2OH$, —$CH_2CH_2OH$ or —$CH(OH)$—$CH_2OH$ and $R_{10b}$ is H or each of $R_{10a}$ and $R_{10b}$ is $CH_2OH$;
or wherein
ii) $R_1$ is OH, and
R is a radical of formula (d)

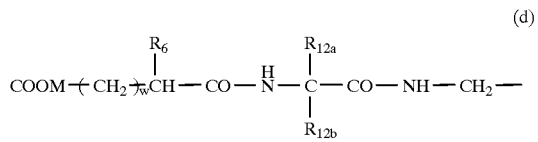

wherein
w is 1 or 2;
$R_{12a}$ is —$CH(OH)$—$(CH_2)_x$—OH and $R_{12b}$ is H or each of $R_{12a}$ and $R_{12b}$ independently is —$CH_2OH$ or —$H_2CH_2OH$;
x is 2 or 3; and
$R_6$ and M are as defined above.

M may be $H^+$ or any salt forming cation for a carboxy or sulfate which maintains the water-solubility of the compound of formula I, e.g. a monovalent or one equivalent of a polyvalent cation, for example an alkali metal ion such as lithium, sodium or potassium, an alkaline earth cation such as calcium or magnesium, as well as zinc, iron and aluminium ions and the ammonium ($NH^+_4$) ion. M is preferably $H^+$, $Li^+$ or $Na^+$. It is preferred that the cation M be a pharmaceutically acceptable cation. When the cation is polyvalent, an appropriate number of molecules of formula I or a mixture of compounds of formula I and one or more appropriate anions such as acetate, chloride, carbonate and the like are also present. $M_1$ may independently have one of the significance given above for M, preferably identical to M.

When $R_x$ is an amino protecting group, it may be such a group as disclosed in "Protective Groups in Organic Synthesis" T. W. Greene, J. Wiley & Sons New York, 2nd ed., chapter 7, 1991, and references therein, preferably a pharmaceutically acceptable amino protecting group, particularly tert.-butoxy-carbonyl or benzyloxycarbonyl.

When $R_2$ in the radical of formula ($a_1$) is a saturated or unsaturated hydrocarbon residue, it may be e.g. $C_{1-20}$alkyl, $C_{2-20}$alkenyl or $C_{2-20}$alkynyl. Examples of $R_2$ bearing a formyl group include e.g. 2-oxo-ethyl, 3-oxo-propyl, 5-oxo-pent-3-enyl, 8-oxo-octyl and 10-oxo-dec-4-enyl. When $R_2$ is an alkyl or alkenyl acetal group formed from a $C_{1-4}$alcohol or $C_{2-4}$diol, it may be e.g. any of the acetals preparable from the above aldehydes using $C_{1-4}$alcohols or $C_{2-4}$diols, e.g. methanol, ethanol, isopropanol, sec.-butanol, n-butanol, ethylene glycol, propylene glycol, 2,3-butanediol, 1,4-butanediol or 1,3-butanediol. $R_2$ is preferably H.

Any $C_{1-4}$alkyl as $R_4$ in the radical of formula ($a_1$) is preferably $CH_3$.

When $R_8$ is $R_s$-$R_p$ or $NHR_y$, the resulting compound of formula I may be or is suitably utilized in a liposomal preparation as part of the liposome membrane as a means for administering said compound. The spacer group $R_s$ is a residue which links the carbonyl to the oxygen of the phosphatidyl residue, e.g. a hydrocarbon residue. The phosphatidyl residue is a glycerophosphate esterified with saturated and/or unsaturated fatty acids, e.g. myristic, palmitic, stearic, palmitoleic or oleic acid.

$R_y$ may be a saturated or unsaturated aliphatic residue optionally comprising or interrupted by a functional group e.g. —CO—, e.g. a residue based on a dicarboxylic acid diester bearing saturated or unsaturated fatty aliphatic residues. $R_y$ is preferably

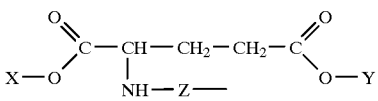

wherein each of X and Y independently is $C_{8-20}$alkyl or $C_{8-20}$alkenyl and Z is a bridging group, e.g. a polyethyleneoxy group, preferably a poly-(3–50, preferably 3–15)-ethyleneoxy group, or a —$C_{1-4}$alkylene-CO— or -phenylene-CO-group.

In the compounds of formula I, the following significances are preferred either individually or in any combination or sub-combination:
1. R is $CH_3$ and $R_1$ is a radical of formula ($a_1$).
2. In the radical of formula ($a_1$) $R_2$ is H.
3. In the radical of formula ($a_1$) $R_3$ is H and $R_4$ is —$CH_2OH$.
4. In the radical of formula ($a_1$) $R_3$ is H and $R_4$ is $CH_3$.
5. R is $CH_3$ and $R_1$ is a radical of formula (b).
6. In the radical of formula (b), $R_5$ is a radical ($b_1$).
7. In the radical ($b_1$) $R_{7a}$ is $CH_2OH$ or $CH(OH)$—$CH_2OH$ and $R_{7b}$ is H.
8. In the radicals ($a_2$) and ($b_3$), the group —$OC_{1-4}$alkyl is preferably $OCH_3$.
9. R is $CH_3$ and $R_1$ is a radical of formula (c).
10. In the radical of formula (c) $R_8$ is $C_{1-6}$alkoxy, preferably methyl or ethyl.
11. In the radical of formula (c), $R_9$ is a radical ($c_1$).
12. In the radical ($c_1$), $R_{10a}$ is $CH(OH)$—$CH_2OH$ and $R_{10b}$ is H.
13. In the radical of formula (c), $R_9$ is a radical ($c_2$).
14. In the radical ($c_2$), $R_6$ is $NH_2$.
15. $R_1$ is OH and R is a radical of formula (d).
16. In the radical of formula (d), $R_{12a}$ is $CH(OH)$—$(CH_2)_x$—OH and $R_{12b}$ is H.

The compounds of formula I may comprise one or more asymetric carbon atoms. It will be understood that the present invention includes all individual isomeric forms, enantiomers and diastereoisomers as well as mixtures, e.g. racemates, unless otherwise stated.

In the radical of formula ($a_1$), the asymmetric carbon atom bearing $R_3$ has preferably following configuration:

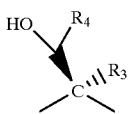

In the radical of formula ($b_1$), when the carbon atom bearing $R_{7a}$ and $R_{7b}$ is asymmetric (i.e. $R_{7b}$ is H), it preferably has following configuration:

The same applies to the asymmetric carbon atom bearing $R_{10a}$ when $R_{10b}$ is H in residue ($c_1$).

In the radicals ($b_2$) and ($c_3$), the pyrrolidinyl moiety preferably has following configuration:

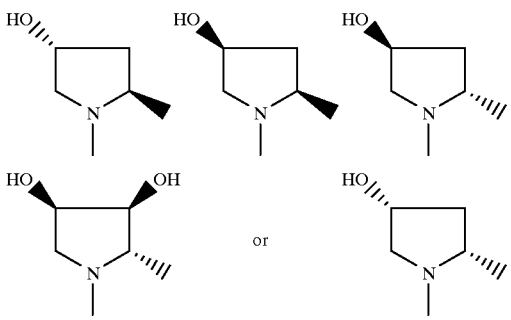

In the radicals ($b_4$) and ($c_2$) the asymmetric carbon atom bearing the substituted benzyl moiety preferably has following configuration:

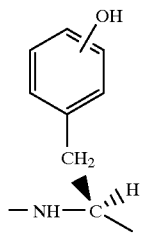

The radical of formula (c) has preferably following stereochemistry:

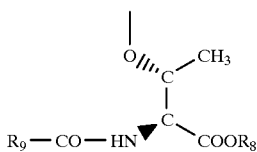

In the radical of formula (d), when $R_{12b}$ is H, the asymmetric carbon atom bearing $R_{12a}$ has preferably following configuration:

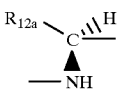

The present invention also includes a process for the production of the compounds of formula I. They may be produced by analogy to known methods. The compounds of formula I may be produced for example by removing at least one protecting group which is present in a compound of formula I in protected form, e.g. amino and/or hydroxy protected form.

The compounds of formula I in protected form are mainly compounds wherein the hydroxy group(s) present in the fucose moiety is (are) protected. Groups which can be employed in the present invention to block or protect the hydroxy group are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Hydroxy-protecting (blocking) groups which are advantageously used are those which are common in carbohydrate chemistry especially for primary alcohols, secondary alcohols and vicinal cis and trans diols.

Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$–$C_6$) alkylsilyl (e.g. trimethylsilyl, triethylsilyl), triisopropylsilyl, isopropyldimethylsilyl, t-butydimethylsilyl, methyldiisopropylsilyl or methyldi-t-butylsilyl), t-butyl-diphenylsilyl, triarylsilyl (e.g. triphenylsilyl, tri-p-xylylsilyl) or triaralkylsilyl (e.g. tribenzylsilyl). Examples of these and other suitable hydroxy-protecting groups e.g. for the protection of 1,2- or 1,3-dihydroxy groups, for example cyclic ether groups such as optionally substituted methylene acetal or ethylidene acetal and methods for their formation and removal are known in the art, e.g., see Protective Groups in Organic Synthesis, second ed., T. W. Greene and P. G. M. Wuts, John Wiley & Sons, New York, 1991, Chapter 2 and references therein.

Compounds of formula I wherein $R_6$ is $NHR_x$ may also be converted in compounds of formula I wherein $R_6$ is $NH_2$ by removal of the amino protecting group $R_x$.

The compounds of formula (I) thus obtained may be recovered in free form or in salt form.

Compounds of formula I in protected form wherein R is $CH_3$ and $R_1$ is a radical of formula (a), used as starting materials may be produced, e.g. as indicated in Scheme 1.

Figure 13:
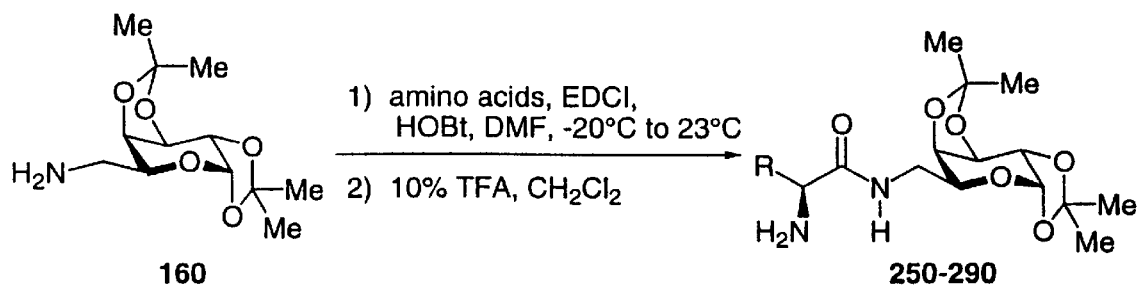

FIG. 13 illustrates the coupling of amino acids 170–190, and 240 with galactose amine core 160.

Figure 14:
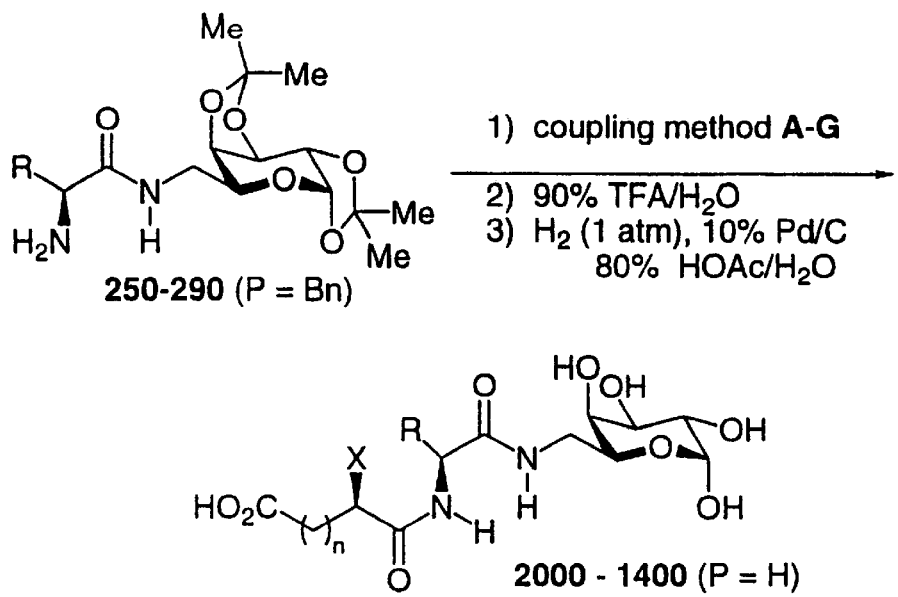

FIG. 14 shows the introduction of the sialic acid mimic and final deprotection with the following indicated coupling methods: A) succinic anhydride, MeOH; B) glutaric anhydride, MeOH; C) EDCI, HOBt, DMF, N-Cbz-benzyloxyaspartic acid; D) $BnO_2C-(CH_2)_2COCl$, $CH_2Cl_2$, $Et_3N$; E) $BnO_2C(CH_2)_3COCl$, $CH_2Cl_2$, $Et_3N$; F) EDCI, HOBt, DMF, $BnO_2C(CH_2)_2CO_2H$; G) EDCI, HOBt, DMF, $BnO_2C(CH_2)_3CO_2H$.

Figure 15:
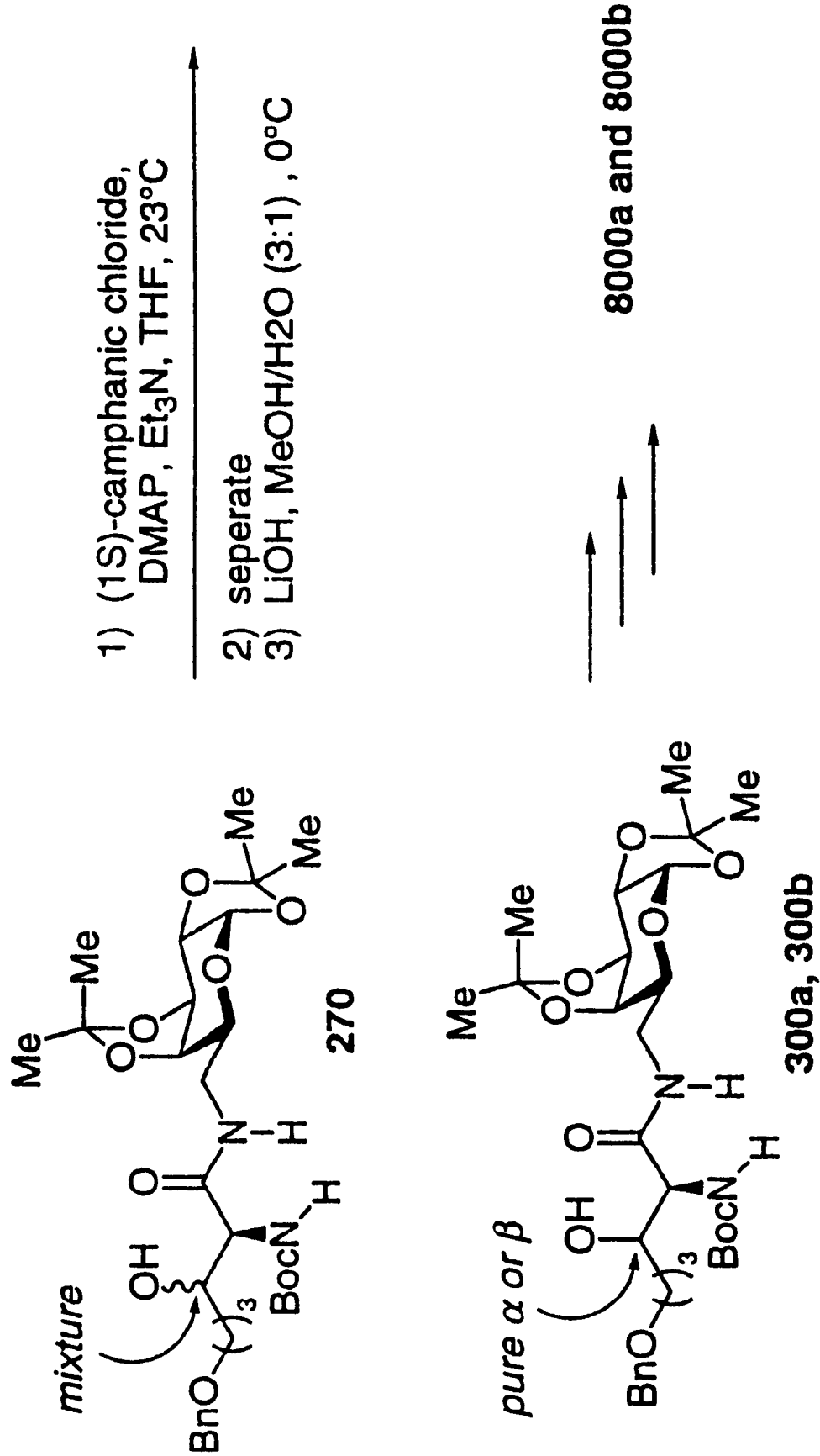

FIG. 15 illustrates the resolution of 8000 into 8000a and 8000b.

Figure 16:
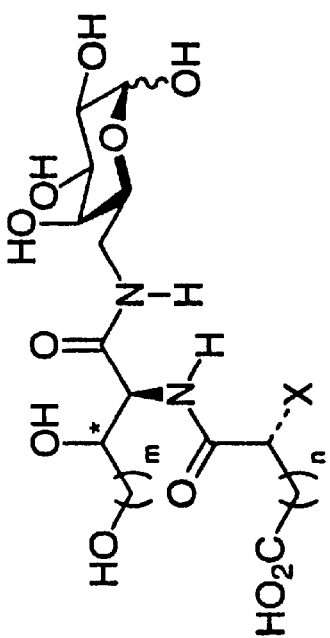

FIG. 16 shows a table representing IC50 values of mimics derived from the enzymatically synthesized amino acids. (1) These compounds were submitted as a mixture at the 2° OH on both the amino acid side chain (indicated with and asterisk) and the anomeric center; (2) the activity shown is derived from a mixture at the anomeric center only, the amino acid stereochemistry (indicated by an asterisk is R); (3) 8000a and 8000b, are enantiomerically pure at the amino acid center but the absolute stereochemistry is unknown.

FIG. 17 shows a table representing IC50 values of mimics derived from synthetically prepared amino acids.

Figure 18:
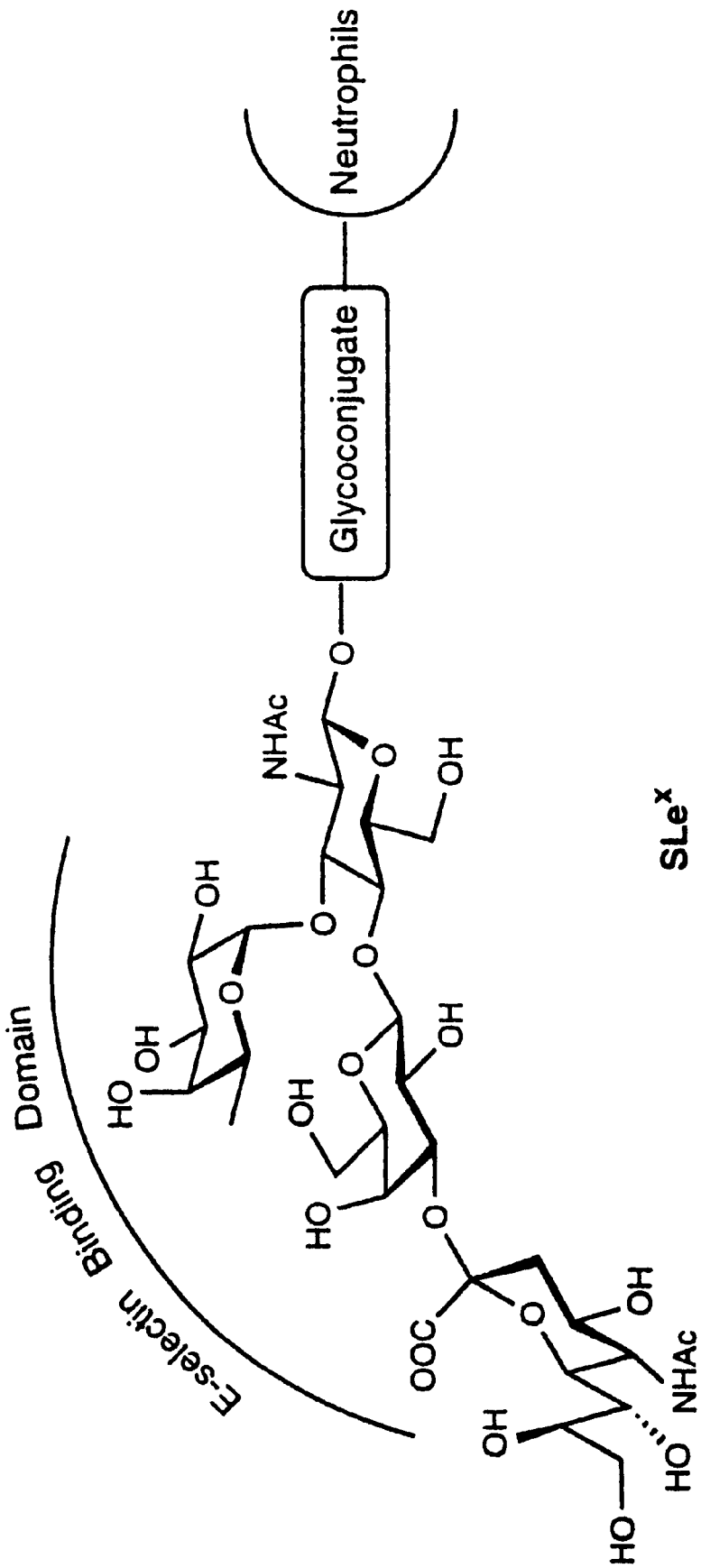

FIG. 18 illustrates the structure/binding domain relationship between $SLe^x$ and E-selectin. Synthesis of mimetics takes into effect this shown binding relationship.

DETAILED DESCRIPTION

The present invention relates to Sialyl Lewis X mimetics, a process for their production, their use as a pharmaceutical and pharmaceutical preparations contaning them. Compounds of this class of $sLe^x$ mimetics possess enhanced and/or substantially the same activity as $sLe^x$ in selectin binding assays.

It is widely accepted that a family of receptors, the selectins, are involved in the recognition of various circulating cells by the endothelium and platelets and play a role in certain diseases including cancer, autoimmune disorders, inflammation, atherosclerosis and blood clotting. There are three known members of this family: L-selectin, P-selectin and E-selectin.

E-selectin (also designated endothelial leukocyte adhesion molecule, ELAM-1) is a cell surface protein inducibly expressed in endothelial cells. For example, its production is increased on vascular endothelial cells when adjacent tissue has been damaged or invaded by a microorganism. E-selectin recognizes sialyl Lewis X ($SLe^x$) which is a cell surface carbohydrate ligand found on neutrophils and monocytes, anchored onto the outer membrane thereof by integral membrane glycoproteins and/or glycolipids. $SLe^x$ mediates binding of neutrophils and monocytes to the activated vascular endothelial cells by binding to E-selectin, so that these leukocytes may diffuse into the damaged tissue.

However, there are many situations in which the recruitment of leukocytes by adhesion to the endothelial cells is abnormal and in excess, and the end result is tissue damage instead of repair.

Although $SLe^x$ has been considered to be potentially useful as an anti-inflammatory agent and its synthesis on large scales has been developed for clinical evaluation, this natural saccharide can only be used as an injectable form in cases presenting with acute symptoms as it is orally inactive and has a short half-life in blood.

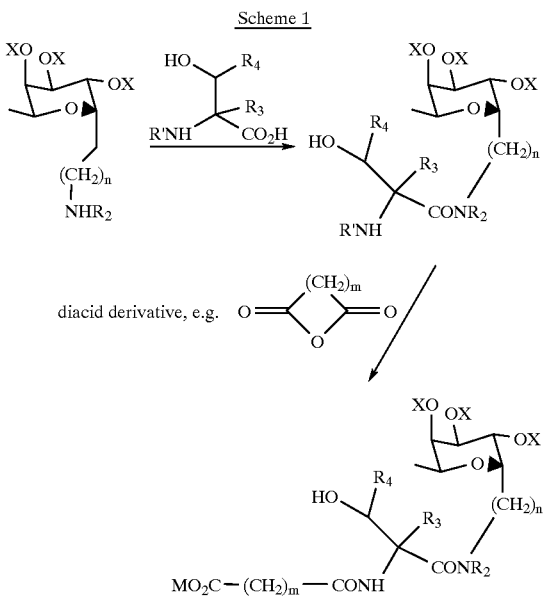

Scheme 1

X is a hydroxy protecting group, e.g. as indicated above. R' is a leaving group, e.g. an amino protecting group, for example Boc or Fmoc. Preferably the starting materials are used as specific enantiomers in order to obtain the compounds of formula I with the desired configuration.

Compounds of formula I in protected form wherein R is $CH_3$ and $R_1$ is a radical of formula (b) used as starting materials may be prepared, e.g. as indicated in Scheme 2.

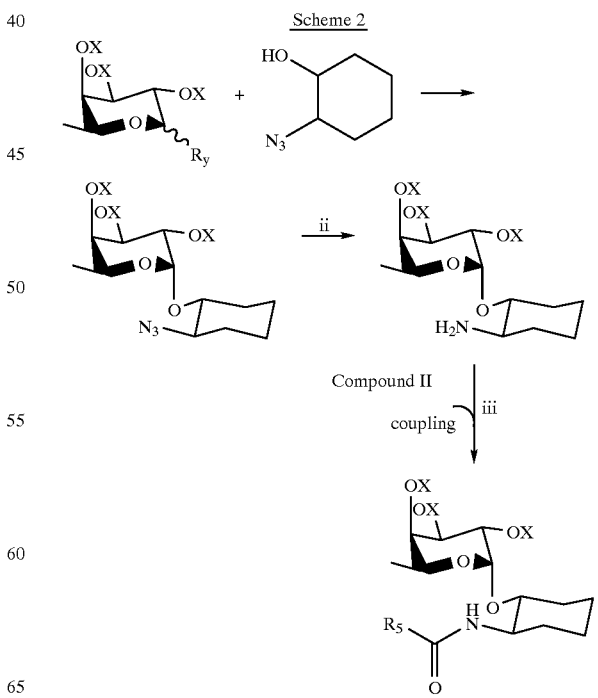

Scheme 2

$R_y$ is a leaving group, e.g. halogen, preferably F. Step ii is a reduction which is intended to include well-known reduction procedures for the azido group such as reaction with a phosphine, e.g. triphenylphosphine, or a hydride, e.g. lithium aluminium hydride. Step iii is an amide bond coupling e.g. as known in the art of peptide chemistry. Compound II may be selected e.g. from Asp-Ser-OH, Glu-Ser-OH, Glu-(α-hydroxymethyl)Ser-OH in protected form, e.g. Compound 10. Step iii may also comprise coupling with an appropriate amino acid in protected form followed by reacting with a diacid derivative as disclosed in Scheme 1.

Compounds of formula I in protected form wherein R is $CH_3$ and $R_1$ is a radical of formula (c) may be prepared e.g. as indicated in Scheme 3.

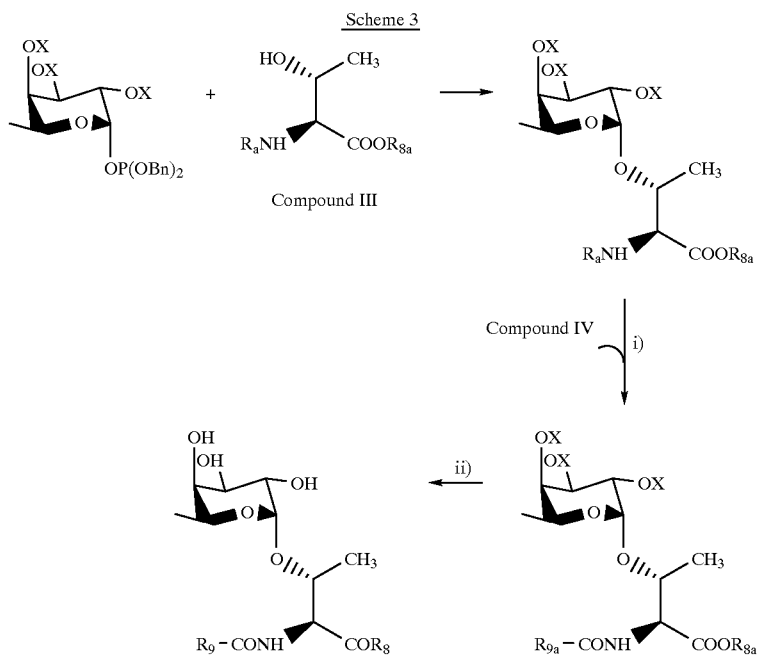

$R_{8a}$ is $C_{1-6}$alkyl. $R_a$ is an amino protecting group. Compound IV may be selected e.g. from 2-amino-3,4-dihydroxybutyric acid, α-hydroxymethyl serine or Glu-Tyr-OH in protected form, e.g. (2S,3R)-N-Boc-2-amino-4-benzyloxy-3-hydroxybutyric acid. $R_{9a}CO$ is the amino acid residue (optionally completed with a diacid residue) of Compound IV. Steps i) and ii) are amide bond coupling reactions effected according to standard procedures. Step ii) may also comprise coupling with an appropriate amino acid in protected form followed by reacting with a diacid derivative, e.g. as disclosed in Scheme 1. Step ii) may further also comprise the conversion of —$COOR_{8a}$ into —$COR_8$, e.g. into an acid, acid salt, lipophilic ester or lipophilic amide, e.g. as disclosed in Examples 44 and 45. Compound III may be used in the form of one or another of the individual enantiomers or in the form of mixtures. Above Scheme 3 illustrate the preparation of a compound of formula I wherein R is $CH_3$ and $R_1$ is a radical of formula (c) with the preferred configuration.

Compounds of formula I in protected form wherein $R_1$ is OH and R is a radical of formula (d) wherein $R_{12a}$ is $CH(OH)$—$(CH_2)_x$—OH, used as starting materials, may be produced e.g. as indicated in Scheme 4.

Scheme 4

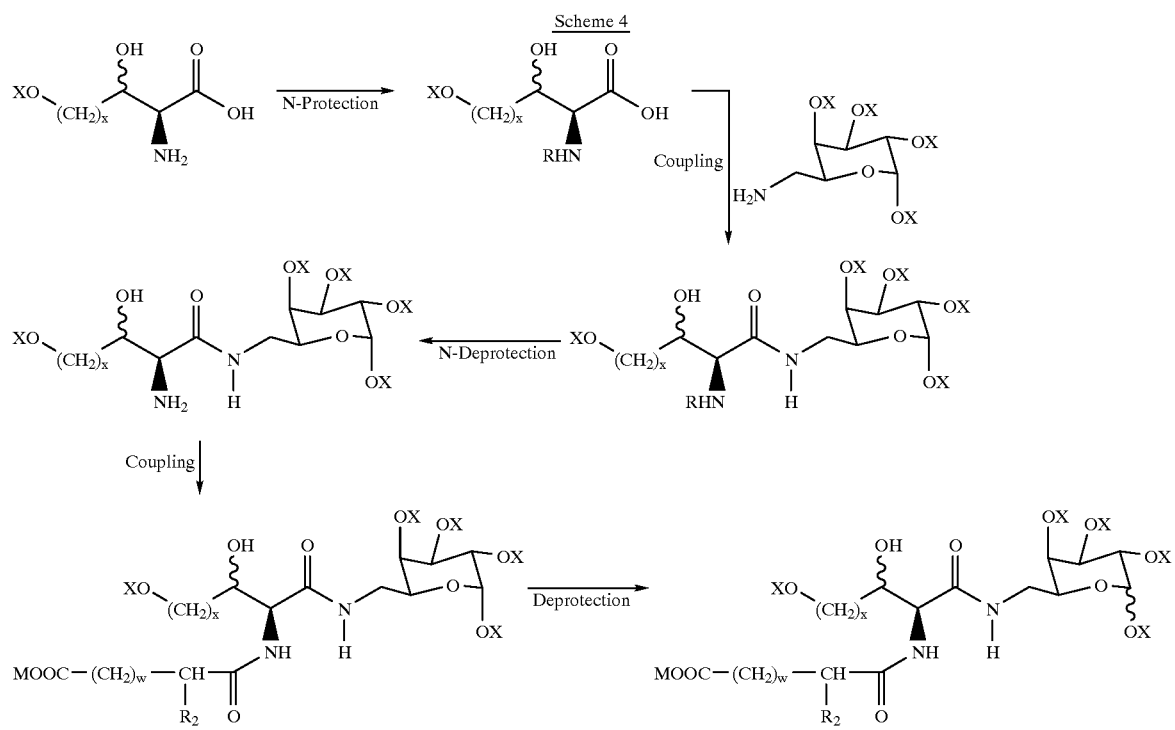

Preferably 2 vicinal X groups (hydroxy protecting groups) form together

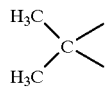

on the fucose moiety.

The above reactions may be effected in analogy with known methods, e.g. as described in the following examples. Insofar as the production of the starting materials is not particularly described, the compounds are known or may be prepared analogously to methods known and practiced in the art.

The following examples are illustrative of the invention. All temperatures are in °C.

Following abbreviations are used:

Ac=—COCH$_3$
Bn=benzyl
Boc=t.-butoxycarbonyl
Fmoc=9-fluorenylmethoxycarbonyl
DAST=diethylaminosulphur trifluoride
EDCI=1-(3-dimethylaminopropyl)-3-ethylcarbodiimide hydrochloride
EDAC=1-ethyl-3-(3-dimethylaminopropyl)-carbodiimide
DMF=dimethylformamide
HOBT=1-hydroxybenzotriazole
TFA=trifluoroacetic acid

EXAMPLE 1

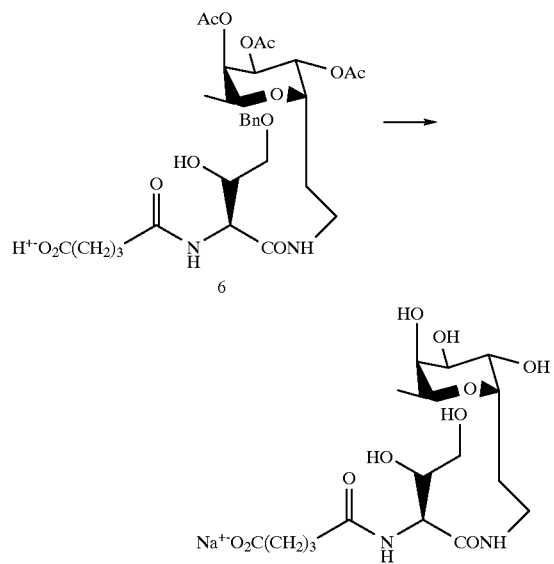

Compound 6 is deprotected by treatment with hydrogen gas over a palladium/carbon catalyst, followed by treatment with sodium methoxide to give the sodium salt of Compound 7.

$^1$H NMR (500 MHz, D$_2$O) δ 1.16 (d, J=6.3 Hz, 3H), 1.75–1.92 (m, 4H), 2.35 (m, 1H), 3.20 (m, 1H), 3.43 (m, 1H), 3.55 (dd, J=6.0, 12.0 Hz, 1H), 3.67 (dd, J=3.0, 12.0 Hz, 1H), 3.73 (m, 2H), 2.84–4.02 (m, 4H); $^{13}$C NMR (125 MHz, D$_2$O) δ 16.6, 21.6, 24.5, 34.3. 35.4, 37.5, 56.5, 63.4, 68.2, 68.7, 70.8, 71.9, 72.6, 74.4, 166.8, 172.5, 177.0; electrospray mass m/z 423 [(MH)⁺; calculated for $C_{17}H_{31}O_{10}N_2$: 423].

Compound 6, used as starting material, may be prepared as follows:

a) Fucose tetraacetate is treated with allyl trimethyl silane and boron trifluoride etherate in dry acetonitrile at room temperature to give Compound 2 (the ratio α;β is greater than 10:1). Kozikowsky, A. P. and Sorgi, K. L. Tetrahedron Lett. (1983), 24: 1563.

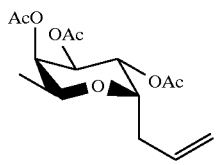

2 b) Compound 2 is ozonolyzed by reaction with ozone in the presence of triphenyl phosphine. The product aldehyde is then subjected in situ to reductive amination by treatment with hydrogen gas over a palladium/carbon catalyst in the presence of ammonium acetate to give the corresponding fucose tetraacetate bearing a 2-amino-ethyl group (Compound 3).

c) Compound 3 as obtained above is coupled with (1S, 2R)-2-N-Boc-amino-4-benzyloxy-3-hydroxy butyric acid (prepared from glycine and O-benzylglycoaldehyde by a threonine aldolase-catalyzed reaction according to Wong et al. Tetrahedron Lett. 1995, 36, 4081) in 1-(3-dimethylaminopropyl)-3-ethylcarbodiionide hydrochloride solution to form the amide Compound 5

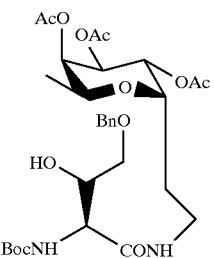

5 d) The protecting group is removed from Compound 5 by treatment with ethyl acetate in acidic solution (4N HCl). The deprotected product is then treated in situ with glutaric anhydride (in triethylamine buffer) to obtain Compound 6.

By following a procedure in analogy with that of Example 1 above, the compounds of formula

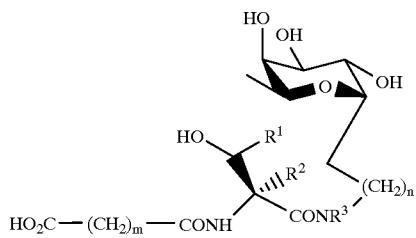

wherein $R_1$, $R_2$, n and m have the significances as indicated in Table 1 below, may be prepared.

TABLE 1

| Ex. | $R_1$ | $R_2$ | n | m |
|---|---|---|---|---|
| 2 | CH₂OH | H | 2 | 3 |
| 3 | CH₃ | H | 1 | 3 |
| 4 | H | CH₂OH | 1 | 3 |
| 5a | CH₃ | H | 1 | 2 |
| 5b | CH₂CH₂OH | H | 1 | 2 |
| 5c | CH₂CH₂OH | H | 1 | 3 |

By following a procedure in analogy with that of Example 1 but using the appropriate starting materials, the compound of Example 6 may be obtained:

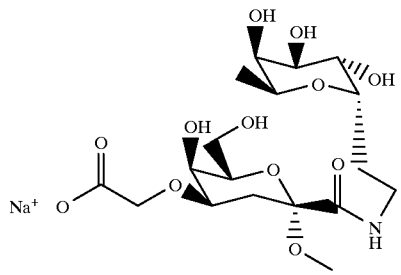

EXAMPLE 7

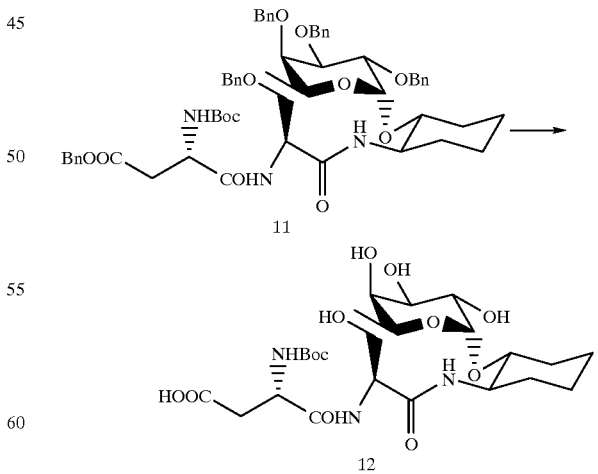

Compound 11 (122 mg, 0.12 mmol) is dissolved in methanol (2 mL), Pd(OH)₂ on carbon (20 mg) is added and the mixture is stirred under hydrogen (1 atm) for 12 hours.

The catalyst is filtered through celite and the product is purified by silica gel chromatography (CHCl₃/methanol, 3:1) and biogel P2 chromatography (H₂O). Compound 12 is obtained after purification. $^1$H NMR (500 MHz, D₂O) δ 1.48 (d, 3H, J=7.0 Hz,H-6), 1.47–1.74 (m, 4H), 1.74 (s, 9H), 2.00–2.11 (m, 3H), 2.47 (m, 1H), 3.64 (s, 1H, H-4), 3.76 (m, 1H). 3.97–4.25 (m, 6H, H-2, H-3, H-5), 4.65–474 (m, 2H), 5.31 (d, 1H, J=3.5 Hz, H-1), $^{13}$C NMR (125 MHz, D₂O) δ 15.80, 23.73, 24.51, 28.18, 30.18, 31.60, 39.68, 49.47, 53.42, 55.89, 55.99, 62.39, 67.12, 68.42, 70.08, 72.39, 94.38, 94.65, 170.9, 171.1, 174.7, 178.1. HRMS calcd for $C_{24}H_{41}N_3O_{12}Cs$ (M+Cs+) 696.1745, found 696.1717.

Compound 11, used as starting material, may be prepared as follows:

a)

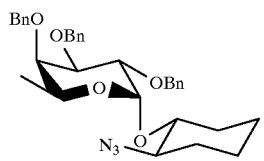

8

2,3,4-Tri-O-benzyl-L-fucopyranose is dissolved in anhydrous dichloromethane at 0° and DAST (1.06 g.0.0066 mol) is dropped in. After the mixture is stirred at 0° for 30 min., the reaction is quenched by the addition of water. The aqueous solution is extracted with dichloromethane and the organic fractions are combined, dried over MgSO₄ and filtered. The solvent is evaporated and the fluoride is used for the glycosylation without further purification. 4 Å Molecular sieves, tin (II) chloride (1.67 g, 0.0088 mol) and silver perchloride (1.82 g. 0.0088 mol) are added to a solution of the fluoride in anhydrous dichloromethane (20 mL) at 0°. The mixture is stirred for 5 min. and (R,R) azidocyclohexanol (0.93 g, 0.0066 mol) is added. The reaction is warmed to room temperature and stirred for 6 hours. After filtration through celite, the filtrate is concentrated and applied to silica gel chromatography (hexane/ethylacetate, 8:1). Compound 8 is obtained as a clear oil.

b)

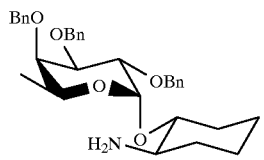

9

Compound 8 (1.3 g, 2.33 mmol) is dissolved in tetrahydrofuran (10 mL, containing 1% H₂O) and triphenylphosphine (638 mg, 2.56 mmol) is added. The mixture is stirred at room temperature for 5 h. After evaporation of the solvent, the residue is purified by chromatography on a silica gel column with CHCl₃/methanol (50:1→30:1).

Compound 9 is obtained as a syrup.

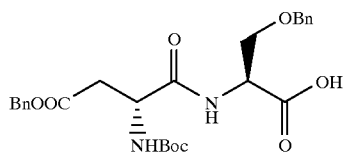

10 c) O-Benzyl-N-Boc-L-aspartic acid is dissolved in anhydrous dichloromethane and EDAC (640.3 mg, 3.34 mmol) and N-hydroxysuccinimide (384.4 mg, 3.34 mmol) are added. The mixture is stirred at 4° for 12 h and the solvent is evaporated. O-benzyl-N-Boc-aspartic N-hydroxy succinimide ester is obtained by silica gel chromatography (ethylacetate/hexane, 1:1.5→1:1).

O-Benzyl-N-Boc-aspartic N-succinimide ester (603 mg, 1.44 mmol) and O-benzyl-serine (281 mg, 1.44 mmol) are dissolved in DMF (2 mL) and Et₃N (1 mL) is added. The mixture is stirred at room temperature for 1 hour. After evaporation of the solvent and silica gel chromatography (CHCl₃) the product 10 is obtained.

d) Acid 10 (141 mg, 0.29 mmol), EDAC (81 mg, 0.42 mmol) and HOBT (57 mg, 0.42 mmol) are dissolved in dichloromethane (2 mL) at room temperature and stirred for 5 min. before compound 9 (148 mg, 0.56 mmol) is added. The mixture is stirred at room temperature for 3 hours and the solvent is evaporated. The residue is applied to a silica gel column (hexane/ethylacetate, 1.5:→1:1) and compound 11 is obtained as a syrup. $^1$H NMR (500 MHz, CDCl₃) δ 1.20 (d, 3H, J=6.5 Hz, H-6), 1.08–1.60 (m, 4H), 1.44 (s, 9H), 1.73 (m, 1H), 1.94 (m, 3H), 2.71 (m, 1H), 3.05 (m, 1H), 3.65 (dd, 1H, J=3.5, 9.5 Hz), 3.76 (m, 1H, H-4), 3.89 (dd, 1H, J=3.0, 9.5 Hz), 3.98 (dd, 1H, J=2.5, 10.0 Hz, H-3), 4.04 (dd, 1H, J=3.5, 10.0 Hz, H-2), 4.10 (m, 1H, H-5), 4.44 (m, 1H), 4.61 (m, 1H), 4.68 (m, 1H), 4.95 (d, 1H, J=3.5 Hz, H-1), 4.45–5.17 (m, 10H), 5.68 (m, 1H), 7.33 (m, 25H). $^{13}$C NMR (125 MHz, CDCl₃) δ 16.72, 23.34, 23.82, 28.20, 36.29, 36.59, 50.42, 50.65, 52.45, 52.58, 52.82, 66.69, 66.72, 66.78, 69.26, 73.09, 73.18, 74.80, 75.98, 75.98, 77.73, 79.35, 94.52. 128.0 (m), 135.2, 135.3, 137.5, 183.6, 139.0, 155.3, 169.6, 170.2, 170.6, 171.9. HRMS cacld for $C_{59}H_{71}N_3O_{12}Cs$ (M+Cs+) 1146.4092, found 1146.4035.

By following a procedure in analogy with that of Example 7 above, but using the appropriate starting materials, the following compounds of formula

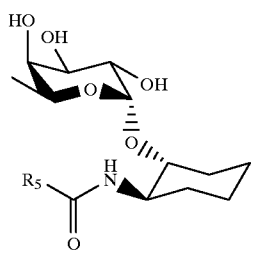

wherein R₅ is as indicated in Table 2, may be prepared.

TABLE 2

| Ex. | R$_5$ | HRMS Calc. | Found |
|---|---|---|---|
| 8 | HO₂C—(CH₂)₂CO—NH—CH— with CH(OH)—CH₂OH substituent | [M$^+$Cs$^+$] 611.1217 | 611.1241 |
| 9 | HO₂C—(CH₂)₂CO—NH—CH— with CH(OH)—CH₂OH substituent (opposite stereochem) | [M$^+$Cs$^+$] 611.1217 | 611.1241 |
| 10 | NaO₂C—(CH₂)₃CO—NH—CH— with CH₂OH substituent | 485.2111 | 485.2127 |
| 11 | HO₂C—(CH₂)₃CO—NH—CH— with CH(CH₂OH)(OH) substituent | [M$^+$Cs$^+$] 625.1373 | 625.1355 |
| 12 | HO₂C—CH₂—CH(NHBoc)—CO—NH—CH— with CH(CH₂OH)(OH) substituent | [M$^+$Cs$^+$] 726.1850 | 726.1832 |
| 13 | NaO₂C—CH₂—CH(NH₂)—CO—NH—CH— with CH(CH₂OH)(OH) substituent | [M$^+$Na$^+$] 516.2169 | 516.2169 |
| 14 | Methyl glycoside with OCH₂CO₂Na substituent | | |
| 15 | Pyrrolidine with 3,4-di-OH, N-CO(CH₂)₃CO₂H | [M$^+$Cs$^+$] 637.1373 | 637.1353 |
| 16 | HO₂C—CH(NH₂)—CH₂—CO—NH—CH— with CH₂-(4-hydroxyphenyl) substituent | [M$^+$Cs$^+$] 672.1533 | 672.1546 |

TABLE 2-continued

| Ex. | R$_5$ | HRMS Calc. | Found |
|---|---|---|---|
| 17 | 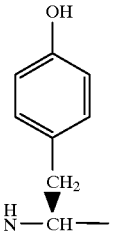 | | |
| 16 | 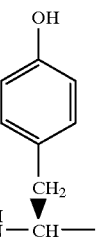 | [M$^+$Cs$^+$] 672.1533 | 672.1546 |
| 17 | 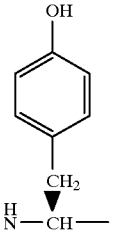 | | |

Compound of Example 11: $^1$H NMR(500MHz, D$_2$O) δ 1.10(d, 3H, J = 6.5Hz, H-6), 1.20(m, 4H), 1.75(m, 6H), 2.16(m, 1H), 2.56(t, 2H, J = 7.5Hz), 2.33(m, 2H), 3.41(m, 1H), 3.43(m, 2H), 3.63(m, 2H, H-2 and H-3), 3.69(m, 1H, H-4), 3.78(m, 1H, H-5), 4.09(ddd, 1H, J = 2.5, 6.0, 8.5Hz), 4.46(d, 1H, J = 2.5Hz), 5.02(d, 1H, J = 3.0Hz, H-1). $^{13}$C NMR(125MHz, D$_2$O) δ 15.85, 21.96, 23.71, 24.60, 28.84, 31.41, 35.38, 35.45, 53.67, 55.19, 62.73, 67.13, 68.26, 69.88, 71.65, 72.22, 75.19, 93.31, 172.3, 176.6.

Compound of Example 11: $^1$H NMR(500MHz, D$_2$O) δ 1.10(d, 3H, J = 6.5Hz, H-6), 1.20(m, 4H), 1.75(m, 6H), 2.16(m, 1H), 2.56(t, 2H, J = 7.5Hz), 2.33(m, 2H), 3.41(m, 1H), 3.43(m, 2H), 3.63 (m, 2H, H-2 and H-3), 3.69(m, 1H, H-4), 3.78(m, 1H, H-5), 4.09(ddd, 1H, J = 2.5, 6.0, 8.5Hz), 4.46(d, 1H, J = 2.5Hz), 5.02(d, 1H, J = 3.0Hz, H-1). $^{13}$C NMR(125MHz, D$_2$O) δ 15.85, 21.96, 23.71, 24.60, 28.84, 31.41, 35.38, 35.45, 53.67, 55.19, 62.73, 67.13, 68.26, 69.88, 71.65, 72.22, 75.19, 93.31, 172.3, 176.6.

Compound of Example 12: $^1$H NMR(500MHz, D$_2$O) δ 1.12(d, 3H, J = 6.5Hz, H-6), 1.08–1.26(m, 4H), 1.39(s, 9H), 1.65–1.80(m, 3H), 2.14(m, 1H), 2.74(m, 2H), 3.39–3.88(m, 9H), 4.37(m, 2H), 4.98 (d, 1H, J = 3.5Hz, H-1). $^{13}$C NMR(125MHz, D$_2$O) δ 15.82, 23.70, 24.58, 28.03, 29.30, 31.78, 37.32, 52.05, 53.40, 55.55, 62.93, 67.14, 68.32, 69.95, 71.99, 72.25, 76.23, 82.21, 94.06, 157.6, 170.8, 173.4, 175.8.

Compound of Example 13: $^1$H NMR(500MHz, D$_2$O) δ 1.15(d, 3H, J = 6.5Hz, H-6), 1.10–1.40(m, 4H), 1.66–1.85(m, 3H), 2.16(m, 1H), 2.59(dd, 1H, J = 8.5, 17.5Hz), 2.72(dd, 1H, J = 5.0, 17.5Hz), 3.40(m, 1H), 3.51(dd, 1H, J = 6.0, 12.0Hz), 3.56(dd, 1H, J = 3.5, 10.0Hz, H-3), 3.60(m, 1H), 3.64(dd, 1H, J = 4.0, 10.0Hz, H-2), 3.69(m, 1H, H-4), 3.73(m, 1H), 3.85(m, 1H), 3.91(m, 1H, H-5), 4.15(m, 1H), 4.40(d, 1H, J = 7.0Hz), 5.00(d, 1H, J = 4.0Hz, H-1). $^{13}$C NMR(125MHz, D$_2$O) δ 15.77, 23.69, 24.62, 29.06, 31.80, 38.41, 51.47, 53.40, 55.59, 62.76, 67.09, 68.35, 69.91, 71.79, 72.24, 75.68, 93.63, 170.6, 176.8, 176.8.

EXAMPLE 18

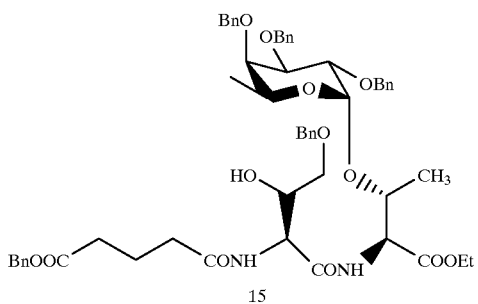

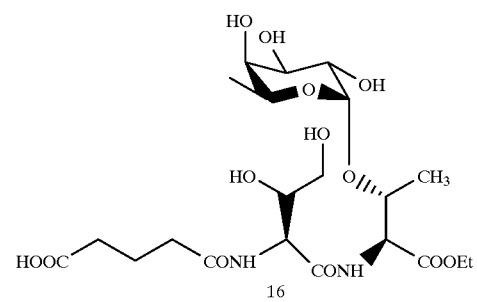

The benzyl groups of 15 are cleaved by hydrogenation according to procedure of Example 5. Compound 16 (amorphous): $^1$H NMR (400 MHz, $D_2O$) δ 4.98 (d, J=3.2 Hz, 1H, H-1), 4.61 (d, J=2.2 Hz, 1H), 4.56 (d, J=7.2 Hz, 1H), 4.46–4.44 (dd, J=2.2 and 6.4 Hz, 1H), 4.28–4.13 (m, 3H), 4.02–3.98 (m, 1H), 3.86–3.59 (m, 5H), 2.42–2.22 (m, 4H), 1.90–1.79 (m, 2H), 1.30–1.18 (m, 9H); electrospray negative mass (declustering potential=–80 V) m/z 523 [(M–H); calcd for $C_{21}H_{36}N_2O_{13}$: 524].

Compound 15, used as starting material, may be prepared as follows:

a)

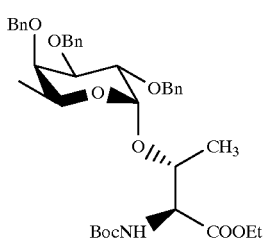

L-Fucose is first converted to tribenzylfucosyl phosphite according to Wong et al. J. Org. Chem. 1994, 59, 864. The resulting compound (1.0 equivalent) is coupled to Boc-L-Thr-OEt (1.1 equivalents) using trifluoromethanesulfonic acid (0.1 equivalent) as catalyst in methylene chloride at 0° to give compound 13 after standard workup and purification.

b)

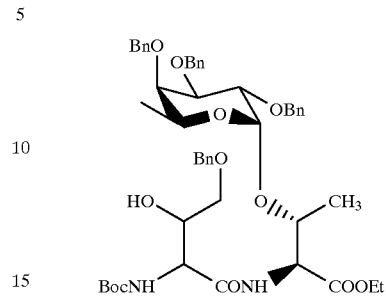

First Boc deprotection of 13 in 30% TFA in 0.1 M $CH_2Cl_2$ at 25°, 30 min; quench water, wash $NaHCO_3$, dry sodium sulfate; purification by flash chromatography gives the corresponding free amine. This amine (1.0 equivalent) is coupled with 1.1 equivalents of (2S,3R)-N-Boc-2-amino4-benzyloxy -3-hydroxy-butyric-acid using 1.5 equiv of EDCl, 1.5 equiv of HOBt, 0.1 M $CH_2Cl_2$, 0°, 30 h, to provide 14 after standard workup and flash column chromatography purification conditions.

c) Boc deprotection of 14 in 30% TFA, 0.1 M $CH_2Cl_2$ at 25°, 30 min is followed by quench with water, wash with $NaHCO_3$ and drying over sodium sulfate. Purification by flash chromatography is followed by coupling with 1.1 equivalents monobenzyl glutarate, 1.5 equiv of EDCl, 1.5 equiv of HOBt, $CH_2Cl_2$, 25°, 20 h, to provide compound 15. Compound 15: $^1$H NMR (400 MHz, $CDCl_3$) δ 8.00 (d, J=9.1 Hz, 1H), 7.21–7.50 (m, 25H), 6.75 (d, J=7.6 Hz, 1H), 5.12–4.57 (m, 11H), 4.35–3.99 (m, 7H), 3.80–3.60 (m, 5H), 2.45 (t, J=7.5 Hz, 2H), 2.43 (t, J=7.0 Hz, 2H), 1.98 (t, J=7.5 Hz, 2H), 1.20–1.26 (m, 6H), 1.06 (d, J=6.4 Hz, 3H); HRMS for $C_{56}H_{66}N_2O_{13}$+Cs+ (M+Cs+), calcd 1107.3614, found 1107.3667.

By following a procedure in analogy with that of Example 18 above but using the appropriate starting materials, the compounds of formula

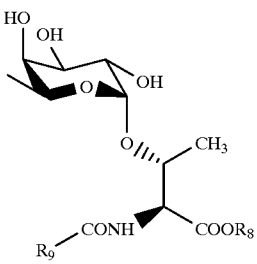

wherein $R_8$ and $R_9$ are as defined in Table 3, may be prepared.

TABLE 3
| Ex. | $R_8$ | $R_9$ | MS calc. | found |
|---|---|---|---|---|
| 19 | H | 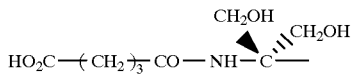 | ES (M − H⁺) 496 | 495 |
| 20 | Li⁺ | 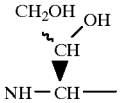 | ES (M − H⁺) 495 | 495 |
| 21 | H | 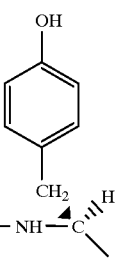 | ES (M − H⁺) 543 | 542 |
| 22 | $C_2H_5$ | 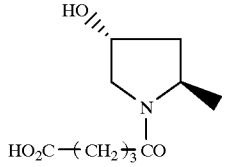 | [M+Na⁺] 543.2166 | 543.2175 |
| 23 | $C_2H_5$ | 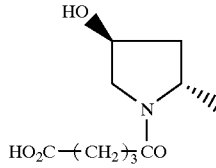 | [M − H⁺ + 2 Cs⁺] 543.2166 | 543.2148 |
| 24 | $C_2H_5$ | 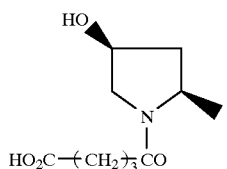 | [M − H⁺ + 2 Cs⁺] 785.0299 | 785.0328 |
| 25 | $C_2H_5$ | 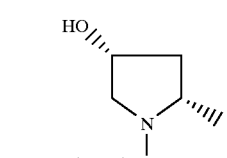 | [M − H]− 519 | 519 |

TABLE 3-continued

| Ex. | R$_8$ | R$_9$ | MS calc. | found |
|---|---|---|---|---|
| 26 | C$_2$H$_5$ | 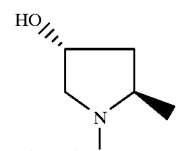 | | |
| 27 | C$_2$H$_5$ | 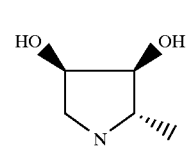 | [M + Cs+]<br>669.1272 | 669.1287 |
| 28 | C$_2$H$_5$ | 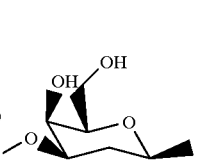 | [M − H + 2 CS]<br>842.9708 | 842.9672 |

EXAMPLE 29

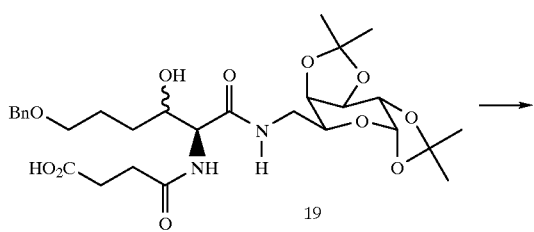

19

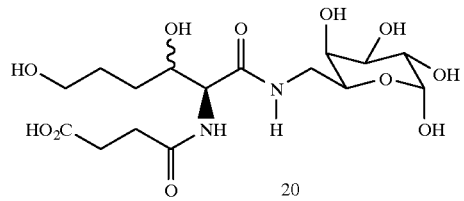

20

A solution of glycopeptide 19 (23.7 mg, 40 μmol) is stirred in 90% TFA in water (1 mL) at room temperature. After 3 hrs., the reaction solution is evaporated down under reduced pressure and azeotroped twice with toluene (2×5 mL). An nmr on the crude product is performed to ensure that the isopropylidene moieties are removed and the product is then taken on to the next step without purification.

The crude glycopeptide is then hydrogenated according to the procedure of Example 5 to give a white solid 20: R$_f$ (4:1:1 nBuOH:H$_2$O:HOAc) 0.29: $^1$H nmr (400 MHz; D$_2$O) 5.23 (d, J 3.7, H1$_\alpha$), 4.55 (dd, J 7.9 and 4.7, H1$_\beta$), 4.37–4.32 (m, H2'$_{(\alpha+\beta)}$), 4.15–4.05 (m, H5$_\alpha$+H3'$_\beta$), 3.95–3.92 (m, H4$_\alpha$+H3'$_\alpha$), 3.86 (d, J 3.4, H4$_\beta$), 3.83 (dd, J 10.3 and 3.2 H3$_\alpha$), 3.78 (dd. J 10.3 and 3.7, H2$_\alpha$), 3.74–3.68 (m, H5$_\beta$) 3.64–3.61 (m, H3$_\beta$+C6'H$_{2(\alpha+\beta)}$), 3.55–3.44 (m, H2$_\beta$+ C6H$_a$H$_{b(\alpha+\beta)}$), 3.42–3.31 (m, C6H$_a$H$_{b(\alpha+\beta)}$), 2.62–2.48 (m, C2"H$_{2(\alpha+\beta)}$)+C3"H$_{2(\alpha+\beta)}$), 1.76–1.47 (m, C4'H$_{2(\alpha+\beta)}$+ C5'H$_{2(\alpha+\beta)}$); $^{13}$C nmr (100 MHz, D$_2$O) 182.93, 179.11, 175.20, 174.66, 98.86, 94.80, 75.19, 75.08, 75.02, 74.21, 72.91, 71.78, 71.48, 71.28, 71.18, 70.71, 70.52, 63.84, 63.80, 61.00, 60.90, 60.48, 42.15, 42.03, 34.71, 34.19, 34.12, 31.84, 31.44, 31.14: High Resolution Mass Spectrum (Doped with NaI): Found M+Na, 447.1570. C$_{16}$H$_{28}$N$_2$O$_{11}$ requires M+Na, 447.1591.

Compound 19, used as starting material, may be prepared as follows:

a)

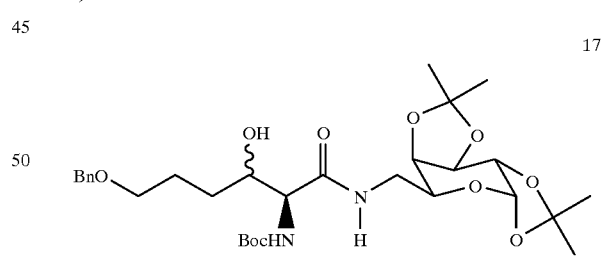

17

EDCI (95.4 mg, 500 μmol) is added to a stirred solution of 6-amino-6-deoxy-1,2,3,4-diisopropylidene-α-L-galactopyranoside (130 mg, 500 μmol), (2S,3RS)-2-N-Boc-amino-6-benzyloxy-3-hydroxy-hexanoic acid (177 mg, 500 μmol), HOBT (68 mg, 500 μmol) and 4-methyl morpholine (108 μL, 1000 μmol) in dry DMF (5 mL) under argon at −20°. The resulting mixture is stirred at −20° for 1 hr and then allowed to warm slowly to room temperature. After 14 hours, the reaction solution is quenched 5% w/v citric acid solution (20 mL) and extracted with ethyl acetate (6×25 mL). The combined organic extracts are washed with saturated sodium hydrogen carbonate solution (50 mL) and saturated sodium chloride solution (50 mL), dried (MgSO$_4$) and evaporated down under reduced pressure. The residual oil is purified by flash chromatography (silica gel, using gradient elution 40%→50%→66% ethyl acetate in hexane) to give 17 as a pale yellow foam: R$_f$ (75% ethyl acetate in hexane) 0.66.

b)

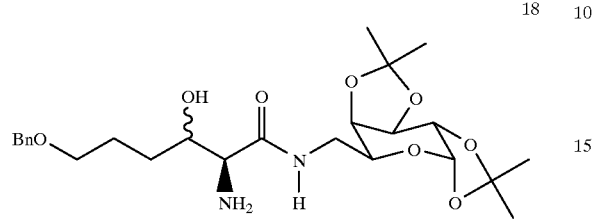

18

A solution of the glycopeptide (17) (59.5 mg, 100 μmol) in 15% v/v trifluoroacetic acid in dry 4-(dicyanomethylene)-2-methyl-6-(4-dimethylaminostyryl)4-H-pyran (1 mL) is stirred under argon at room temperature. After 2 hr., the solution is evaporated down under reduced pressure and the residual oil dissolved up in n-butanol:water:methanol (5:3:2) (10 mL). To the solution is added Dowex (Cl, prewashed with methanol, 100 mg) and the mixture stirred for 30 mins., then filtered and the solid washed with methanol (3×5 mL) and the combined filtrate and washings evaporated under reduced pressure. The residual oil is purified by flash chromatography (silica gel, using gradient elution 19:0.9:0.1→9:0.9:0.1 DCM:MeOH:NH$_3$ $_{(aq)}$) to give 18 as a light brown oil: R$_f$ (9:0.9:0.1 DCM:MeOH:NH$_3$ $_{(aq)}$) 0.42.

c) Succinic anhydride (6.0 mg, 60 μmol) is added to a stirred solution of amino glycopeptide 18 (27.7 mg, 56 μmol) in methanol (1 mL) at room temperature. After 1 hr, the solution is evaporated down under reduced pressure. The residual solid is purified by flash chromatography (silica gel, using gradient elution 5→10% acetic acid in ethyl acetate) to give compound 19 as a pale yellow gum. R$_f$ (10% acetic acid in ethyl acetate) 0.49: IR (Film) cm-1 3303, 2980, 2935, 1644, 1558, 1436, 1382, 1255, 1211, 1167, 1109, 1070, 1006, 901: $^1$H nmr (400 MHz; CD$_3$OD) 7.32–7.23 (5H, m, aromatic), 5.44 (1H, d, J 5.0, 2×H1), 4.59 (1H, dd, J 7.9 and 2.1, 2×H3), 4.48 (2H, s, 2×CH$_2$Ph), 4.38–4.34 (1H, m, 2×H'2), 4.31 (1H, dd, J 5.0 and 2.4, 2×H2) 4.21 (1H, d, J 7.9, 2×H4), 4.00–3.89 (1.5H, m, 2×H5+H3'), 3.84–3.76 (0.5H, m, H3'), 3.52–3.46 (3H, m, 2×C6H$_a$ H$_b$+2×C6'H$_2$), 3.27–3.20 (1H, m, 2×C6 H$_a$ H$_b$), 2.56–2.48 (4H, m, 2×C2"H$_2$+2×C3"H$_2$), 1.80–1.54 (4H, m, 2×C4'H$_2$+2×C5'H$_2$), 1.45 (3H, s, acetonide Me), 1.40 (3H, s, acetonide Me), 1.32 (3H, s, acetonide Me), 1.29 (3H, s, acetonide Me): $^{13}$C nmr (100 MHz; CD$_3$OD) 137.21, 126.78, 126.24, 126.03, 107.86, 107.34, 95.19, 71.24, 70.06, 69.56, 69.28, 69.24, 68.58, 64.68, 56.66, 38.02, 28.96, 28.35, 24.54, 23.83, 23.75, 22.62, 21.99: High Resolution Mass Spectrum (Doped with CsI): Found M+Cs, 727.1875. C$_{29}$H$_{42}$N$_2$O$_{11}$ requires M+Cs, 727.1843.

By following a procedure in analogy with that of Example 29 but using the appropriate starting materials, the compounds of formula

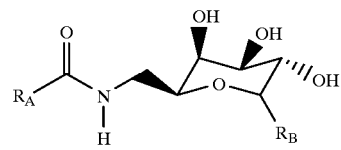

wherein R$_A$ and R$_B$ are as defined in Table 4, may be prepared.

TABLE 4

| Ex. | R$_A$ | R$_B$ |
|---|---|---|
| 30 | HO$_2$C—CH$_2$–CH(NH$_2$)—CO—NH—CH—(CH(OH)—(CH$_2$)$_2$OH) | ⁓OH |
| 31 | HO$_2$C—(CH$_2$)$_2$—CO—NH—CH—(CH(OH)—(CH$_2$)$_3$OH) | ⁓OH |
| 32 | HO$_2$C—(CH$_2$)$_2$—CO—NH—CH—(CH(OH)—(CH$_2$)$_3$OH) | ⁓OH |
| 33 | HO$_2$C—(CH$_2$)$_2$—CO—NH—CH—(CH(OH)—(CH$_2$)$_2$OH) | ⁓OH |

TABLE 4-continued

| Ex. | $R_A$ | $R_B$ |
|---|---|---|
| 34 | HO—(CH₂)₃—CH(OH)—CH— with HO₂C—(CH₂)₃—CO—NH (▲) | ⋯OH |
| 35 | HO—(CH₂)₂—CH(OH)—CH— with HO₂C—(CH₂)₃—CO—NH (▲) | ⋯OH |
| 36 | HO(▲)CH—CH₂OH, CH— with HO₂C—(CH₂)₂—CO—N(▲)H | ∿OH |
| 37 | HO(▲)CH—CH₂OH, CH— with HO₂C—CH₂—CH(NH₂)(▲)—CO—N(▲)H | ∿OH |
| 38 | HO(▲)CH—CH₂OH, CH— with HO₂C—(CH₂)₃—CO—N(▲)H | ∿OH |
| 39 | HO∿CH—(CH₂)₃—OH, CH— with HO₂C—CH₂—CH(NH₂)(▲)—CO—N(▲)H | ∿OH |
| 40 | HO—CH₂, CH₂OH, HO₂C—(CH₂)₂—CO—NH—C(▲)⫿ | ∿OH |
| 41 | HO—CH₂, CH₂OH, HO₂C—(CH₂)₃—CO—NH—C(▲)⫿ | ∿OH |
| 42 | HO—CH₂, CH₂OH, CH₂, HO₂C—(CH₂)₂—CO—NH—C(▲)⫿ | ∿OH |
| 43 | CH₂OH, HOCH₂, CH₂, HO₂C—(CH₂)₃—CO—NH—C(▲)⫿ | ∿OH |

EXAMPLE 44

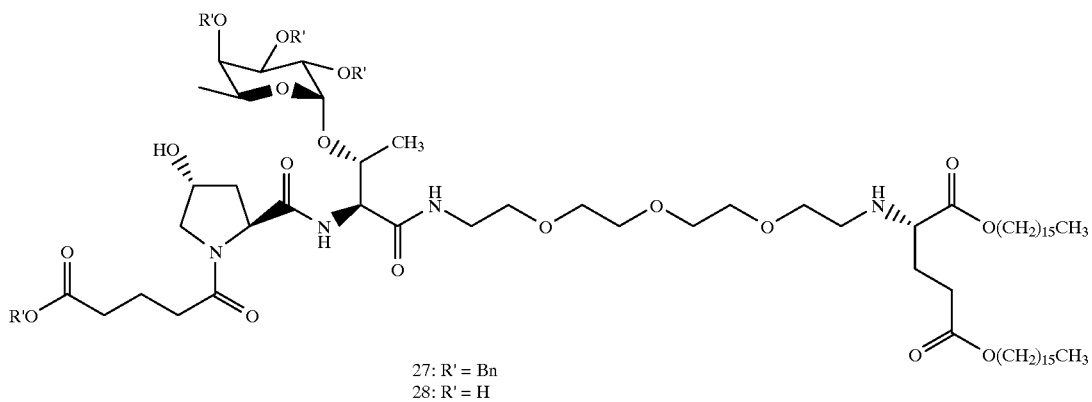

27: R' = Bn
28: R' = H

To the solution of compound 27 (91.4 mg, 59.2 μmol) in MeOH (5 mL) is added Pd(OH)$_2$ on carbon (20 mg). The mixture is stirred for 2 days under hydrogen balloon. The catalyst is filtered off and the filtrate is evaporated in vacuo. The residue is applied to silica gel column chromatography (CHCl$_3$:MeOH=1:1) and then sephadex LH20 gel filtration chromatography (eluted with MeOH) to obtain the desired amphiphile 28. $^1$H NMR (500 MHz, CD$_3$OD) d 0.80 (6H, t, J=6.5), 1.16 (6H, d, J=5.5), 1.23–1.41 (52H, m), 1.60–1.71 (4H, m), 2.04–2.17 (2H, m), 2.31–2.60 (6H, m), 2.66–2.77 (2H, m), 2.97–3.09 (2H, m), 3.31–3.40 (3H, m), 3.50–3.71 (14H, m), 3.79–3.87 (1H, m), 3.88–3.98 (1H, m), 4.04–4.26 (4H, m), 4.44–4.56 (3H, m), 4.95 (1H, brs). HRMS calcd for C$_{62}$H$_{114}$N$_4$O$_{17}$Cs (M+Cs) 1319.7233, found 1319.7264.

Compound 27, used as starting material, may be prepared as follows:

a)

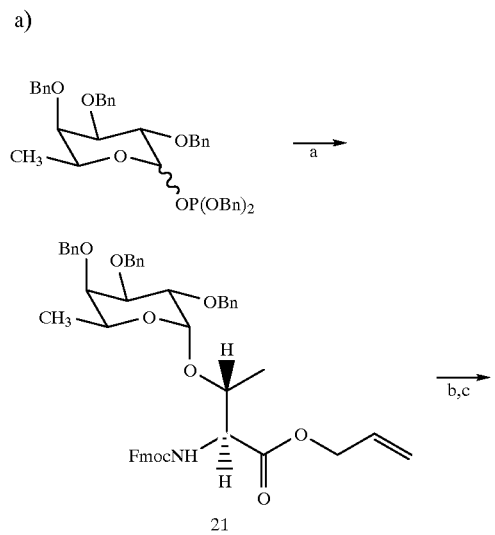

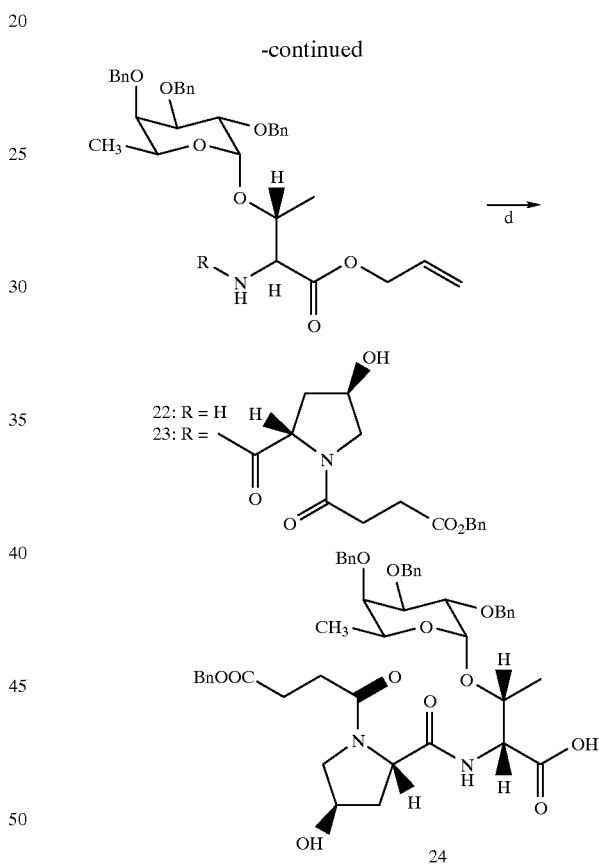

Compound 21

A suspension of dibenzyl 2,3,4-O-tribenzyl-α-L-fucopyranosyl phosphite (138 mg, 0.204 mmol), N-Fmoc threonine allyl ester (77.5 mg, 1 eq) and molecular sieve 4 Å (470 mg) is stirred for 18 hr at room temperature. To the mixture is added a solution of TMSOTf (13.6 mg, 0.3 eq) in CH$_2$Cl$_2$ (1 mL) at −15°. After stirring for 2 hr at the same temperature, saturated NaHCO$_3$aq is added to quench and the mixture is diluted with CH$_2$Cl$_2$. The organic lay is separated, dried over MgSO$_4$ and evaporated in vacuo. The residue is applied to silica gel column chromatography (Hex:EtOAc=4:1) to obtain the compound 21.

Compound 22

To a solution of compound 21 (104 mg, 0.13 mmol) in CH$_2$Cl$_2$ (5 mL) is added Et$_2$NH (0.72 mL, 53 eq) and the mixture is stirred for 18 hr at room temperature. The solvent and reagent are removed in vacuo and the residue is purified by silica gel column chromatography (CH$_2$Cl$_2$—CH$_2$Cl$_2$:MeOH=100:3) to obtain the compound 22.

Compound 23

To a solution of the compound 22 (242 mg, 0.42 mmol) and N-benzyl glutarylamide-L-proline (135 mg, 1 eq) in CH$_2$Cl$_2$ (5 mL) is successively added HOBT (86 mg, 1.5 eq) and EDC (105 mg, 1.3 eq) at 0°. The reaction mixture is stirred for 20 min at 0° and the temperature is allowed to rise to room temperature within 18 hr. The reaction mixture is evaporated in vacuo and the residue is dissolved with EtOAc. The EtOAc solution is washed with 1 N HCl, saturated NaHCO$_3$ and brine successively. The organic layer is dried over MgSO$_4$ and evaporated in vacuo. The residue is applied to silica gel column chromatography (toluene-toluene:acetone=2:1) to obtain the compound 23.

Compound 24

To a solution of the compound 23 (169 mg, 0.192 mmol) and morpholine (167 mg, 10 eq) in THF (10 mL) and DMF (1 mL) is added Pd(PPh$_3$)$_4$ (23 mg, 0.1 eq) under argon atmosphere at room temperature. After stirring for 24 hr, the reaction mixture is evaporated in vacuo. The residue is dissolved with EtOAc and washed with 1N HCl. The organic layer is separated, dried over MgSO$_4$ and evaporated in vacuo. The residue is purified on silica gel column chromatography (CH$_2$Cl$_2$—CH$_2$Cl$_2$:MeOH 10:1) to obtain the compound 24.

b) Synthesis of lipid part

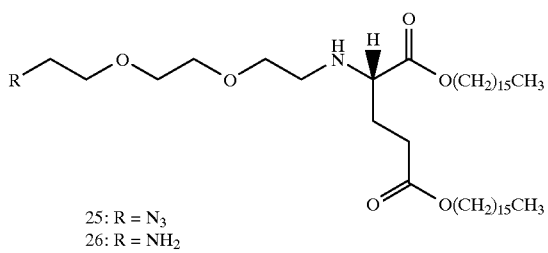

25: R = N$_3$
26: R = NH$_2$

Compound 25

To a solution of oxalyl chloride (1.54 mL, 2N CH$_2$Cl$_2$: solution) is added a solution of DMSO (277 mg, 1.5 eq) in CH$_2$Cl$_2$ (3 mL) and a solution of 2-[2-(2-azidoethoxy) ethoxy]ethanol in CH$_2$Cl$_2$ (5 mL) each 2 min interval at −78°. After the mixture is stirred for 30 min at the same temperature, Et$_3$N (1.64 mL) is added to the mixture at −78° and the temperature is allowed to rise to room temperature within 1 hr. The reaction mixture is poured into ice water and extracted with CH$_2$Cl$_2$. The organic layer is washed with 1N HCl and saturated NaHCO$_3$ successively, dried over MgSO$_4$ and evaporated in vacuo. The crude aldehyde is used without further purification. To a solution of the crude aldehyde and 1',3'-dicetyl-L-glutamate p-toluenesulfonic acid salt (500 mg, 1 eq) in THF (3 mL) and MeOH (9 mL) is added NaCNBH$_3$ (41 mg) at 0°. The mixture is stirred at 0° for 1 hr and the temperature is allowed to rise to room temperature within 18 hr. The solvent is evaporated in vacuo and the residue is dissolved with CH$_2$Cl$_2$. After the solution is washed with 1 N HCl, the organic layer is dried over MgSO$_4$ and evaporated in vacuo. The residue is applied to silica gel column chromatography (Hex-EtOAc=4:1) to obtain compound 25.

Compound 26

To the solution of compound 25 (320 mg, 0.427 mmol) in MeOH (13 mL), THF (3 mL) and 1N HCl (1.3 mL) is added Pd on carbon (99 mg). The mixture is stirred for 2 days under hydrogen balloon. The catalyst is filtered off and the filtrate is evaporated in vacuo. To the residue is added saturated NaHCO$_3$ and the mixture is extracted with EtOAc. The organic layer is dried over MgSO$_4$ and evaporated in vacuo to obtain compound 26.

Coupling between sLe$^x$ mimetic and Lipid

Compound 27

To a solution of compound 24 (94.6 mg, 0.113 mol) and compound 26 (81.7 mg, 1 eq) in CH$_2$Cl$_2$ (5 mL) is added HOBT (23 mg, 1.5 eq) and EDC (29 mg, 1.3 eq) successively at 20°. The reaction mixture is stirred at 0° and the temperature is allowed to rise to room temperature within 20 hr. The reaction mixture is evaporated in vacuo and the residue is dissolved with EtOAc. After the solution is washed with saturated NaHCO$_3$, the organic layer is dried over MgSO$_4$ and evaporated in vacuo. The residue is purified on silica gel column chromatography (toluene:acetone= 1:1) to obtain compound 27.

$^1$H NMR (500 MHz, CDCl$_3$) δ 0.88 (6H, t, J=7.0), 1.12 (3H, d, J=6.0), 1.17 (3H, d, J=6.0), 1.21–1.41 (52H, m), 1.57–1.65 (4H, m), 1.88–1.97 (2H, m), 2.12–2.20 (1H, m), 2.22–2.29 (1H. m), 2.38 (2H, t, J=7.0), 2.45–2.83 (5H, m), 3.18–3.27 (2H, m), 3.42–3.59 (10H, m), 3.63 (1H, brs), 3.66 (1H, dd, J=11.0, 4.0), 3.82 (1H, dd, J=10.3, 3.0), 3.84 (1H, q, J=7.0), 4.01–4.13 (4H, m), 4.48–4.58 (4H, m), 4.61 (1H, d, J=11.5), 4.64 (1H, d, 3=11.5), 4.69 (1H, d, J=11.5), 4.74 (1H, d, J=11.5), 4.75 (1H, d, J=11.5), 4.92 (1H, d, J=11.5), 4.96 (1H, d, J=3.5), 5.06 (2H, s), 7.10 (1H, brt, J=3.0), 7.25–7.43 (20H, m), 7.87 (1H, t, J=9.0). m/z C$_{90}$H$_{138}$N$_4$O$_{17}$ 1548 (M+H)

EXAMPLE 45

By following a procedure in analogy with that of Example 44 but using the appropriate starting materials, the following compound may be obtained

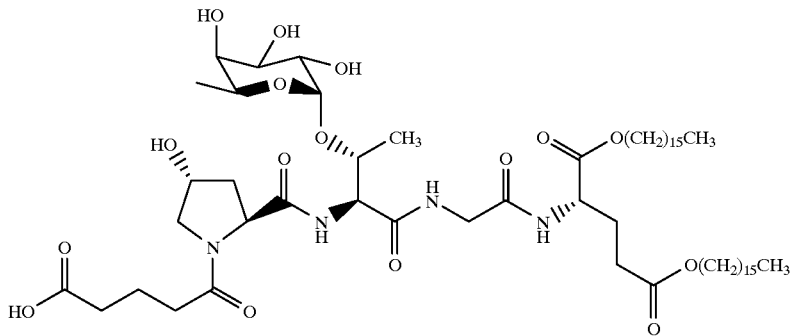

¹H NMR (500 MHz, CDCl₃) d 4.80 (d, J=2.6 Hz, 1H), 4.46 (t, J=8.5 Hz, 1H), 4.42–4.40 (m, 4H), 4.05–3.95 (m, 6H), 3.76–3.43 (m, 6H), 2.23 (t, J=7.7 Hz, 2H), 2.30–2.20 (m, 3H), 2.12–2.01 (m, 2H), 1.98–1.91 (m, 4H), 1.85–1.77 (m, 1H), 1.57–1.50 (m, 4H), 1.25–1.13 (br., >50H), 1.11 (d, J=6.3 Hz, 3H), 1.09 (d, J=6.6 Hz, 3H), 0.78 (t, J=6.7 Hz, 6H); MS m/e calc'd for $C_{59}H_{106}N_4O_{16}Cs$ (M+Cs⁺): 1259.6658, found 1259.6620

The compounds of formula I and their pharmaceutically acceptable salts exhibit pharmaceutical activity and are, therefore, useful as pharmaceuticals. In particular, they inhibit adhesion between cells containing a selectin such as E-selectin on their surfaces and effector cells such as neutrophils or HL-60 cells that have $SLe^x$ on their cell surfaces, or a synthetic poly-$SLe^x$-product or poly-$SLe^a$-product. More particularly, the compounds of formula I inhibit $sLe^x$ binding to E-selectin as indicated in the following test methods:

a) Preparation of a soluble form of E-selectin. The extracellular domain of E-selectin, fused to the constant region of the κ light chain (mCκ) is cloned into the baculovirus shuttle vector pVL941 (Invitrogen) and expressed in SF-9 cells. The soluble fusion protein is purified by affinity chromatography using the rat anti-mouse Cκ monoclonal 187.1 antibody coupled to Sepharose.

Cellular Binding Assays. The compounds of formula I are assayed for their ability to block the adhesion of HL-60 cells to E-selectin immobilized onto 96 well plates. Rat anti-mouse Cκ antibody is added to 96 well plates (20 μg/ml in carbonate/bicarbonate buffer, pH 9.5) and incubated overnight at 4° C. The plates are blocked with 3% BSA in assay buffer (20 mM HEPES, pH 7.4 containing 150 mM NaCl and 1 mM CaCl₂) for 8 hours at room temperature and washed 3× with assay buffer. E-selectin mouse Cκ fusion protein (10 μg/ml in assay buffer) is added and incubated for 2 hours at 37° C. or overnight at 4° C. The plates are washed 3× with assay buffer. Then the compound to be assayed is added and pre-incubated for 15–30 min at 37° C. 1×10⁵ labelled HL-60 cells in assay buffer are transferred to each well and allowed to adhere to the E-selectin for 30–45 min at 37° C. Then the plates are gently washed 3–4× with assay buffer to remove unbound cells. Adherent cells are quantified by measurement of fluorescence (Cytofluor 2350 system).

Fluorescent labelling of HL-60 cells with BCECF-AM: HL-60 cells are cultured in Iscove medium supplemented with 20% FCS, glutamine and non essential amino acids. One day before the experiment is performed, the cells are subcultured (1×10⁶ c/ml). The cells (1×10⁶ c/ml) are labelled by incubating with 5 μg/ml BCECF-AM (diluted from stock in DMSO) for 20 minutes at 37° C. in PBS.

Materials:
ELISA plate: Nunc Immuno Plate MaxiSorp (439454)
HL-60 cells: obtained from ATTC catalogue
Affinity purified E-selectin: each batch of E-selectin is tested functionally to determine the appropriate concentration for use in the assay.
Fluorescent dye: bis-carboxyethyl-carboxyfluorescein acetoxy methyl ester (BCECF-AM) available from Molecular Probes.

In this assay, compounds of formula I inhibit adhesion of HL-60 cells to E-selectin, at a concentration of from 0.3 to 10 mM. Compounds of Examples 12, 13 and 18 inhibit adhesion of HL-60 cells to E-selectin at a rate of 100% and 80% (for the 2 later) in a concentration of 10 mM.

b) $sLe^a$-polymer/E-selectin cell free binding assay. Rat anti-mouse Cκ antibody (10 μg/ml in carbonate-bicarbonate buffer, pH 9.5), prepared from rat hybridoma cell line 187.1 (ATCC) is coated onto microtiter plates overnight at 4° C. The plates are washed two times with assay buffer (20 mM HEPES, pH 7.4 containing 150 mM NaCl and 1 mM CaCl₂), blocked for 8 hours at 4° C. with 3% BSA in assay buffer and washed 3 times. To each well E-selectin mouse Cκ fusion protein (3 μg/ml in assay buffer) is added followed by an incubation overnight at 4° C. A complex is formed between biotinylated $sLe^a$-polymer (polyacrylamide-type glycoconjugate, Syntesome GmbH, Munich, Germany) containing 20% mol $sLe^a$ (=0.81 μmol $sLe^a$/mg polymer) and streptavidin-peroxidase (Boehringer Mannheim, Germany) by incubating 20 μl of $sle^a$-polymer (1 mg/ml) with 80 μl streptavidin-peroxidase, 20 μl fetal calf serum and 80 μl assay buffer without CaCl₂ for two hours at 37° C. (the pre-formed $sLe^a$-polymer/streptavidin-peroxidase complex is stable over several months at 4° C). The complex is then diluted 3:10'000 in assay buffer and added to the E-selectin coated wells together with the compound to be assayed. The complex is allowed to bind for two hours at 37° C. before the plates are washed twice with cold assay buffer. ABTS peroxidase substrate (Biorad) solution is added to the wells and the reaction is stopped after 10 min. Bound $sLe^a$-polymer complex is determined by measuring the optical density at 405 nm in a microplate reader. In this assay, compounds of formula I inhibit the $sLe^a$-polymer/E-selectin binding interaction when used at a concentration of from 0.07 to 10 nM.

Compounds of Examples 12, 13 and 18 inhibit the $SLe^a$-polymer/E-selectin binding interaction at an $IC_{50}$ (50% inhibition) of 1 mM, 10 mM and 0.5 mM, respectively.

c) In vivo assays. A compound of formula I may be used as a one-for-one replacement for $SLe^x$ in vivo treatments, e.g. as described in the rat/cobra venom model by Mulligan et al., Nature, 364: 149–151 (1993) or in the feline model of myocardial ischaemia/reperfusion injury by Murohara et al., Cardiovascular Research 30, 965–974 (1995). Compounds of formula I show a beneficial effect in these models.

The compounds of formula I are, therefore, useful in the treatment and/or prevention of disorders or diseases which are mediated by the binding of selectins in cellular adhesion, particularly E-selectin, e.g. acute or chronic inflammatory or autoimmune diseases such as rheumatoid arthritis, asthma, allergy conditions, psoriasis, contact dermatitis, adult respiratory distress syndrome, inflammatory bowel disease and ophthalmic inflammatory diseases, infection diseases such as septic shock, traumatic shock, thrombosis and inappropriate platelet aggregation conditions, cardiovascular diseases such as heart attacks, reperfusion injury, multiple sclerosis and neoplastic diseases including metastasis conditions, strokes and acute or chronic rejection of organ or tissue transplants.

For the above uses the required dosage will of course vary depending on the mode of administration, the particular condition to be treated and the effect desired. In general, however, satisfactory results are achieved at dosage rates of from about 0.5 to 80 mg/kg animal body weight. Suitable daily dosage rates for larger mammals, for example humans, art of the order of from about 100 mg to 1.5 g/day, conveniently administered once, in divided dosages 2 to 4×/day, or in sustained release form. Unit dosage forms suitably comprise from about 25 mg to 0.750 g of a compound of formula I, together with a pharmaceutical acceptable diluent or carrier therefor.

Compounds of formula I may be administered in free form or in pharmaceutically acceptable salt form. Such salts may be prepared in conventional manner and exhibit the same order of activity as the free compounds. The present invention also provides a pharmaceutical composition comprising a compound of the invention, in free base form or in pharmaceutically acceptable salt form in association with a pharmaceutically acceptable diluent or carrier. Such compositions may be formulated in conventional manner. Compounds of the invention may be administered by any conventional route, for example parenterally e.g in form of injectable solutions or suspensions, or in a nasal or a suppository form.

In accordance with the foregoing the present invention further provides:

a) a compound of the invention or a pharmaceutically acceptable salt for use as a pharmaceutical;

b) a method for preventing or treating disorders as indicated above in a subject in need of such treatment, which method comprises administering to said subject an effective amount of a compound of formula I or a pharmaceutically acceptable salt;

c) a compound of the invention or a pharmaceutically acceptable salt for use in the preparation of a pharmaceutical composition for use in the method as in b) above.

Figure 1:
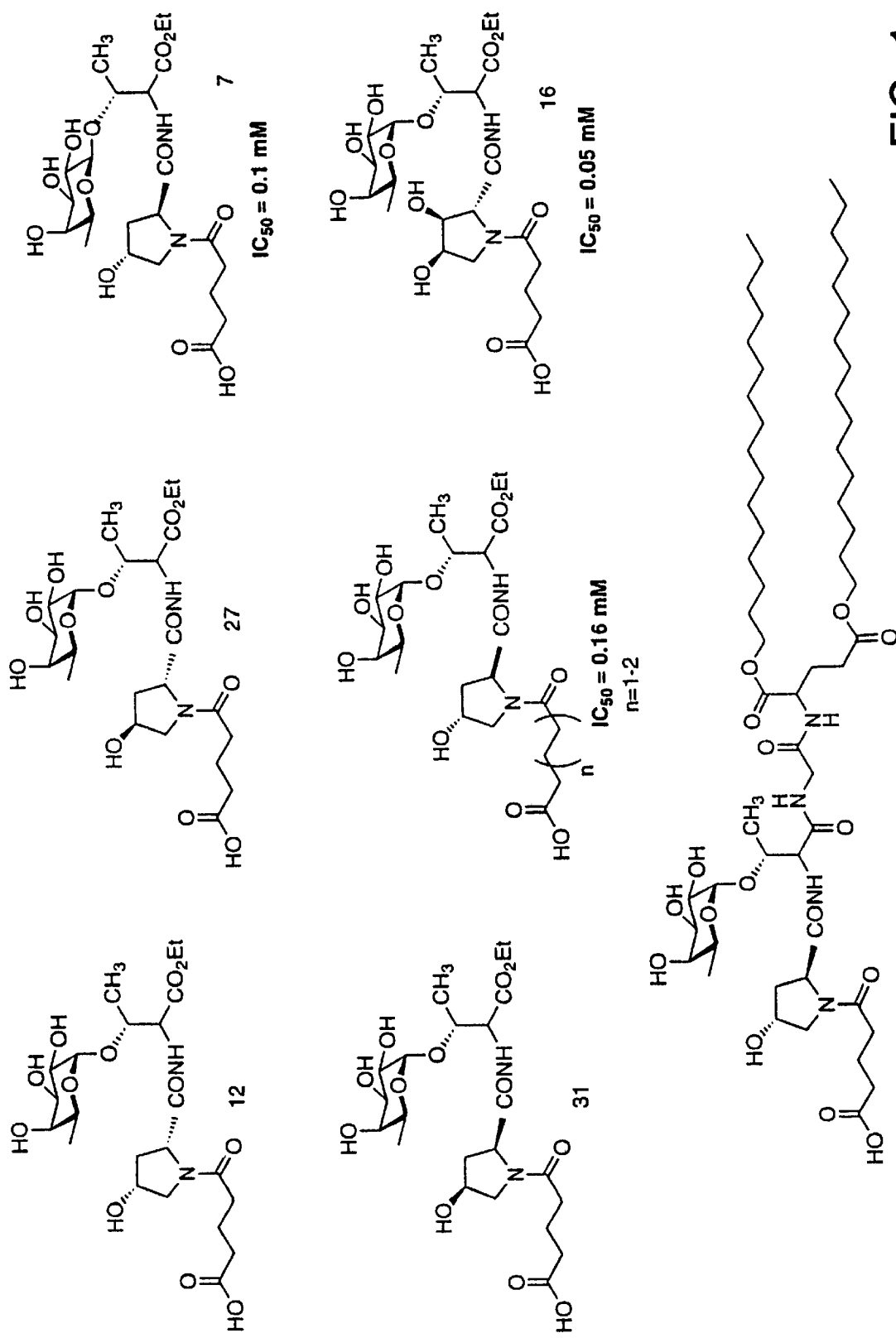
FIG. 1 illustrates various fucopeptide-pyrollidine substituted mimetics with $IC_{50}$ activities indicated.
Figure 2:
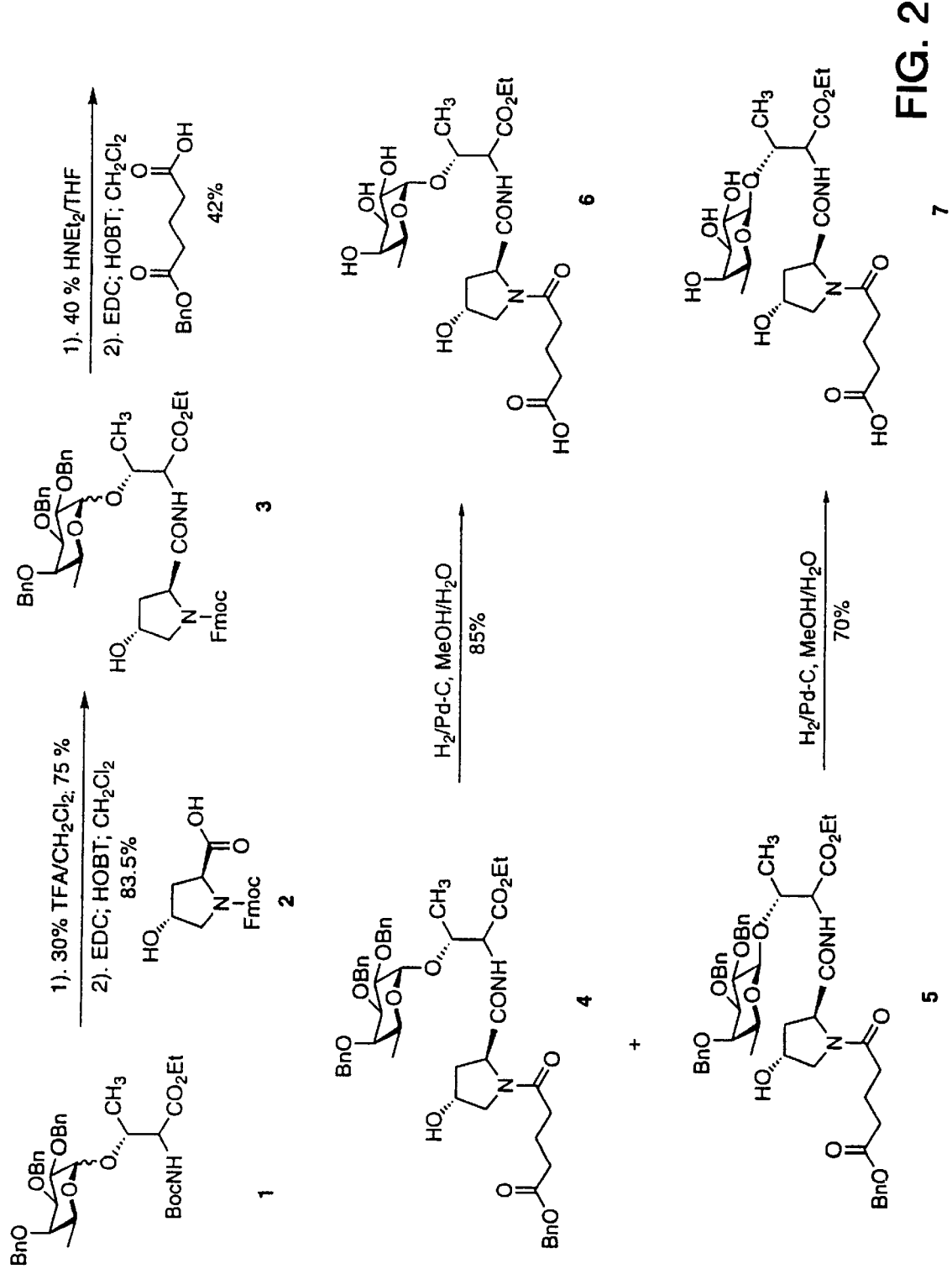
FIG. 2 illustrates the synthesis of fucopeptide 7.

Synthetic Methods
Synthesis of Compound 1 as Shown in FIG. 2

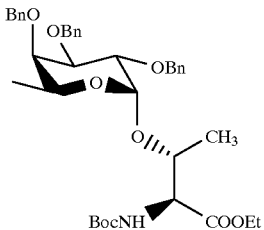

Compound 1

L-Fucose (Sigma) was first converted to tribenzylfucosyl phosphite, from methodology established by Muller et. Al. Liebigs Ann. Chem. 1994, 325 and Wong et. Al. J. Org. Chem. 1994, 59, 864. The resulting compound (1.0 equivalents) was successfully coupled to Boc-L-Thr-OEt (1.1 equivalents; Wong et. al. J. Org. Chem. 1994, 59, 864) using trifluromethanesulfonic acid or TMSOTf (0.1 equivalents) as catalyst in methylene chloride at 0° C. to give the Boc-L-Thr (tri-o-benzyl-α-Fuc)-OEt (1) in 80% yield after standard workup and purification (1× water, 1× $NaHCO_3$, brine, dry over sodium sulfate and then flash chromatography). $^1H$ NMR (400 MHz, $CDCl_3$) δ 7.25–7.40 (m, 15H), 5.34 (d, J=9.6 Hz, 1H, NH), 4.92 (d, J=11.6 Hz, 1H), 4.84 (d, J=3.8 Hz, 1H), 4.79 (d, J=11.4 Hz, 1H), 4.76 (d, J=11.5 Hz, 1H), 4.67 (d, J=11.7 Hz, 1H), 4.62 (d, J=11.9 Hz, 1H), 4.60 (d, J=11.6 Hz, 1H), 4.32–3.99 (m, 5H), 3.80 (dd, J=2.8 and 10.1 Hz, 1H), 3.69 (dq, J=7.0 Hz, 1 H), 3.60 (d, J=2.4 Hz, 1H), 1.48 (s, 9H), 1.20–1.26 (m, 6H), 1.06 (d, J=6.4 Hz, 3H); HRMS for $C_{38}H_{49}NO_9+Cs^+$ ($M+Cs^+$), calcd 796.2462, found 796.2485.

Synthesis of Compound 3 as Illustrated in FIG. 2

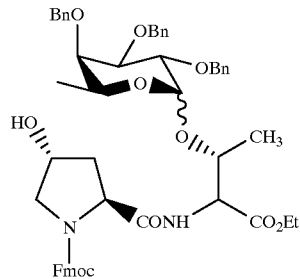

Compound 3

A solution of N-Boc-L-threonine esters 1 (30 μmol) dissolved in 30% TFA in $CH_2Cl_2$ (2 mL) was allowed to stand for 30 min at room temperature and evaporated in vacuo. The residue was dissolved in $CH_2Cl_2$ (1 mL) and neutralized with $Et_3N$ (0.5 mL). To the solution were successively added 1-hydroxybenztriazole (HOBT, 5.4 mg, 40 μmol), 2 (40 μmol; synthesized infra) and EDCI (7.7 mg, 40 μmol) at 0° C. The solution was stirred for 1 h at 0° C. and the temperature was allowed to rise to room temperature within 15 h. The reaction mixture was washed with 10% HCl, 5% $NaHCO_3$ and brine, successively, and dried over $MgSO_4$. After evaporation in vacuo, the residue was applied to silica gel column chromatography (hexane:EtOAc=1:2) to obtain the compound 3. The FMOC-trans-4-hydroxy-L-proline 2 was prepared as follows: 1.1 equivalents of FMOC-chloride is added to 1.0 equivalents of trans-4- hydroxy-L-proline (Aldrich company) and allowed to stir for 12 hour at 25° C. in 0.10 M methylene chloride. The resulting mixture is quenched with water, washed with sodium bicarbonate and dried over magnesium sulfate (standard workup conditions). The crude compound can then be purified by flash chromatography. Mass Spectral analysis: m/e calc'd for $C_{53}H_{58}O_{11}N_2Cs$ (M+Cs$^+$): 1031.3095, found 1031.3143.

Synthesis of Compounds 4 and 5 as Illustrated in FIG. 2

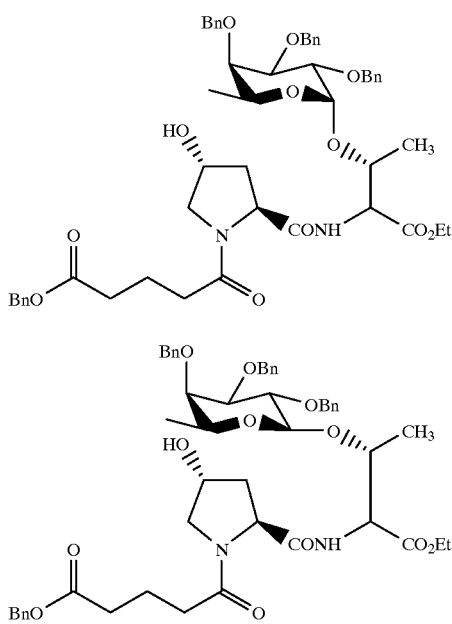

Compound 4 and 5

To a solution of 3 (258 mg, 0.27 mmole) in 40% HNEt (ethylamine; Aldrich chemical company) in THF (10 mL) was allowed to proceed at room temperature for 2 h and evaporated in vacuo. The residue was dissolved in 4 mL THF and then were succesively added benyl monoglutarate (Aldrich), 1-hydroxybeztiazole (HOBT, 73 mg, 0.54 mmole) and 1-(3-dimethylaminopropyl)-3-ethylcarbodiimide (EDC) (104 mg, 0.54 mmole) at 0° C. After being stirred at 0° C. for 10 h, the solvent was evaporated and the residue was diluted with EtOAc. The resulting organic layer was washed with $H_2O$ (2×10 mL), 1 N HCl (2×5 mL), saturated aqueous $NaHCO_3$ (2×5 mL), brine, dried over $MgSO_4$, filtered and concentrated. The organic residue was purified by flash column chromatography eluting with Toluene:EtOAc (1:1) then (1:2) to afford the products 4 and 5 (total yield 42%, 4:5=70:30). Compound 5. $^1$H NMR (500 MHz, CDCl$_3$) δ 7.40 (d, J=7.0 Hz, 1H), 7.35–7.26 (m, 20H), 5.09 (s, 2H), 4.94 (d, J=11.5 Hz, 1H), 4.87 (d, J=11.5 Hz, 1H), 4.75–4.64 (m, 5H), 4.55 (dd, J=8.8, 2.3 Hz, 1H), 4.52–4.44 (m, 3H), 4.35 (d, J=7.7 Hz, 1H), 4.03–3.99 (m, 2H), 3.71 (dd, J=9.7, 7.7 Hz, 1H), 3.56–3.51 (m, 2H), 3.46 (dd, J=9.7, 2.9 Hz, 1H), 3.43 (q, J=6.4 Hz, 1H), 3.35 (dd, J=10.8, 2.3 Hz, 1H), 2.43–2.39 (m, 2H), 2.35–2.25 (m, 3H), 2.05–2.01 (m, 1H), 1.97–1.92 (m, 2H), 1.31 (d, J=6.4 Hz, 3H), 1.15 (d, J=6.3 Hz, 3H), 1.13 (t, J=7.2 Hz, 3H).

Synthesis of Compound 6 as Illustrated in FIG. 2

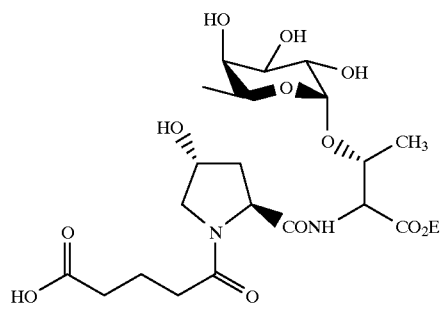

Compound 6

Compound 4 (16 mg, 0.015 mmole) was dissolved in methanol:$H_2O$ (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P2 (water). The collect fractions were combined and freeze dried to afford the title compound 6.

Synthesis of Compound 7 as Illustrated in FIG. 2

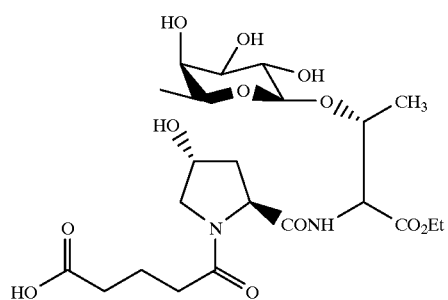

Compound 7

Compound 5 (16 mg, 0.015 mmole) was dissolved in methanol:$H_2O$ (2:1, 2 mL), and then a catalytic amount of Pd(OH)$_2$ (Degussa type) on carbon was added. Hydrogen was supplied to the reaction system through a ballon. The reaction was completed in 6 h. The mixture was filtered through celite and concentrated in vacuo. The crude product was purified by biogel P2 (water). The collect fractions were combined and freeze dried to afford the title compound 7 (5.6 mg, 70%). $^1$H NMR (500 MHz, D$_2$O) δ 4.48–4.41 (m, 4H), 4.18 (d, J=7.9 Hz, 1H), 4.05 (q, J=7.1 Hz, 2H), 3.64 (dd, J=11.8, 3.9 Hz, 1H), 3.59 (q, J=6.5 Hz, 1H), 3.57–3.45 (m, 2H), 3.43 (dd, J=9.8, 3.4 Hz, 1H), 3.24 (dd, J=9.8, 7.9 Hz, 1H), 2.35–2.15 (m, 5H), 1.96–1.90 (m, 1H), 1.72–1.66 (m, 2H), 1.16 (d, J=6.4 Hz, 3H), 1.11 (t, J=7.1 Hz, 3H), 1.08 (d, J=6.5 Hz, 3H); $^{13}$C NMR (125 MHz, D$_2$O) δ 180.1, 175.0, 174.9, 171.8, 103.7, 76.7, 72.9, 70.1, 68.4, 63.3, 63.2, 59.0, 57.4, 55.9, 46.9, 37.6, 34.6, 33.5, 20.6, 18.5, 15.7, 13.6; MS m/e calc'd for $C_{22}H_{36}N_2O_{12}Na$ (M+Na$^+$): 543.2166, found 543.2175.

Figure 3:
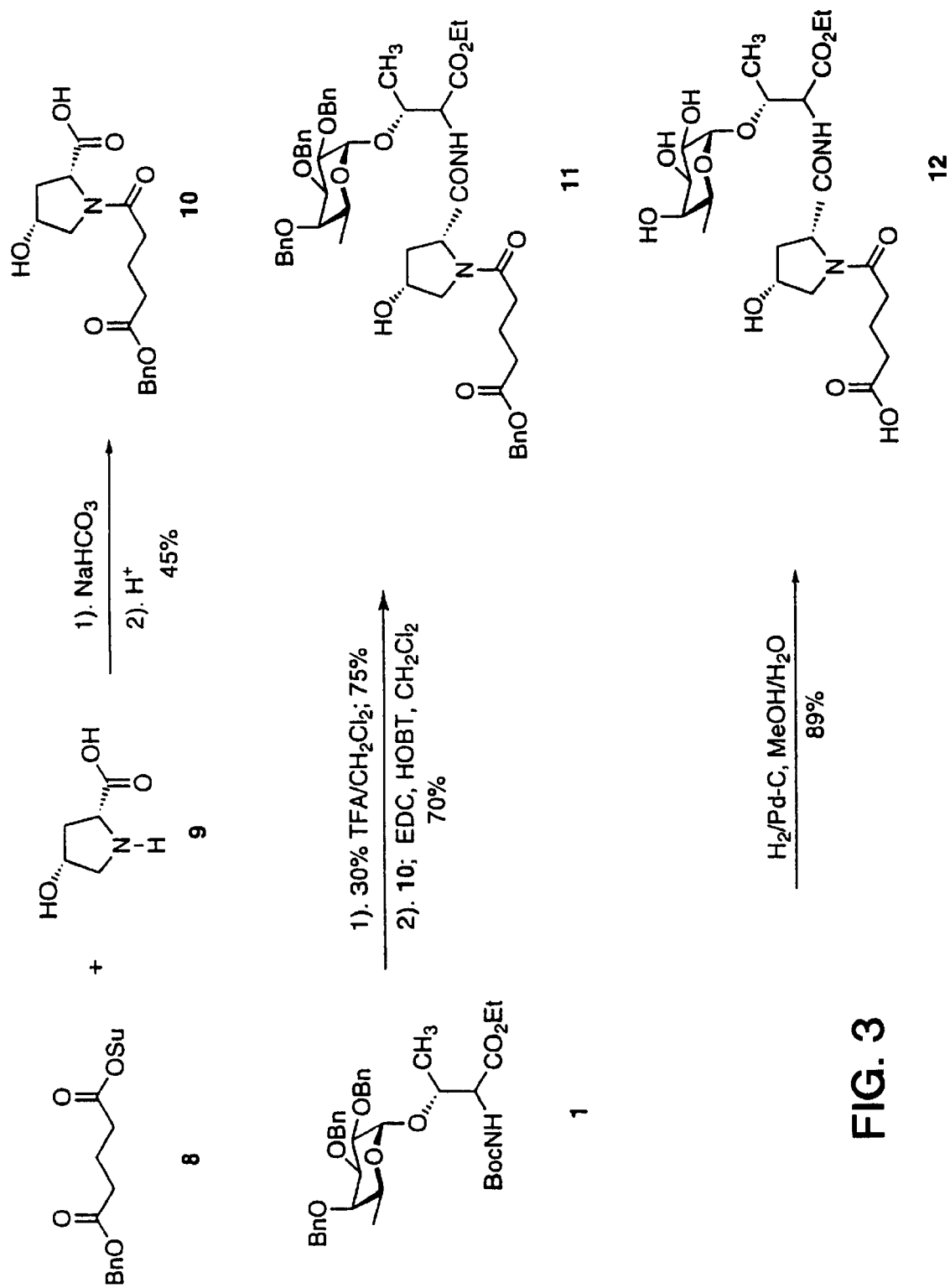
FIG. 3 illustrates the synthesis of fucopeptide 12.

Synthesis of Compound 10 as Illustrated in FIG. 3

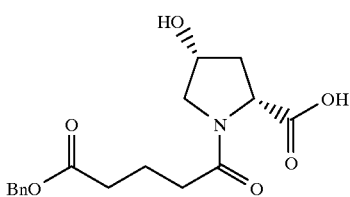

10

Compound 10

A solution of cis-4-hydroxy-L-proline 9 (115 mg, 0.88 mmole; Aldrich) and sodium hydrogen carbonate (73.5 mg, 0.88 mmole) in water (1 mL) is treated with a solution of 8 (207, 0.58 mmole; formed via addition of 1.1 equivalents succinic anhydride to 1.0 equivalents benyl monoglutarate obtained from Aldrich) in 1,4-dioxane (1 mL). One hour later water (1 mL) was added and the solution was extracted with ether (2×5 mL). The aqueous layer was acidified to pH 2 with 1 N HCl and then extracted with EtOAc (2×5 mL). The organic layer was washed with brine twice, dried over $MgSO_4$, filtered and concentrated. The residue was applied to silica gel column chromatograph ($CHCl_3$:MeOH=4:1) to obtain compound 10. $^1$H NMR (500 MHz, $CD_3O$) δ 7.35–7.28 (m, 5H), 5.09 (s, 2 $H_a$), 5.08 (s, 2 $H_b$), 4.43–4.32 (m, 2H), 3.67 (dd, J=10.8, 5.0 Hz, 1 Ha), 3.61 (dd, J=12.8, 3.7 Hz, 1 $H_b$), 3.50–3.44 (m, 1H), 2.46–2.31 (m, 5 $H_a$, 6 $H_b$), 2.06–2.04 (m, 1 $H_a$) 1.92–1.88 (m, 2H); $^{13}$C NMR (125 MHz, $CD_3O$) δ 175.0, 174.7, 174.5, 173.9, 137.7, 129.6, 129.3, 129.2, 71.2, 69.8, 67.2, 56.3, 56.0, 40.3, 38.3, 34.2, 34.2, 34.1, 33.9, 26.3, 21.4, 21.1; MS m/e calc'd for $C_{17}H_{21}NO_6Na$ (M+Na$^+$): 358.1267, found 358.1254.

Synthesis of Compound 11 as Illustrated in FIG. 3

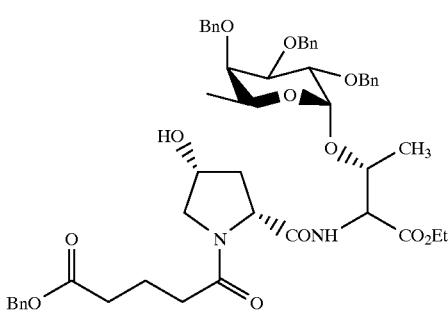

11

Compound 11 (30 μmol) dissolved in 30% TFA in $CH_2Cl_2$ (2 mL) was allowed to stand for 30 min at room temperature and evaporated in vacuo. The residue was dissolved in $CH_2Cl_2$ (1 mL) and neutralized with $Et_3N$ (0.5 mL). To the solution were successively added 1-hydroxybenztriazole (HOBT, 5.4 mg, 40 μmol), 10 (40 μmol; synthesized supra) and EDCI (7.7 mg, 40 μmol) at 0° C. The solution was stirred for 1 h at 0° C. and the temperature was allowed to rise to room temperature within 15 h. The reaction mixture was washed with 10% HCl, 5% $NaHCO_3$ and brine, successively, and dried over $MgSO_4$. After evaporation in vacuo, the residue was applied to silica gel column chromatography (hexane:EtOAc=1:2) to obtain the compound 11. $^1$H NMR (500 MHz, $CDCl_3$) δ 8.20 (d, J=9.2 Hz, 1H), 7.42–7.25 (m, 20H), 5.22 (d, J=9.6 Hz, 1H), 5.08 (dd, J=15.1, 12.3 Hz, 2H), 4.97–4.61 (m, 7H), 4.84 (br., 1H), 4.46 (dd, J=9.0, 1.7 Hz, 1H), 4.41–4.39 (m, 1H), 4.33 (dd, J=6.2, 1.9 Hz, 1H), 4.16–4.13 (m, 1H), 4.07–4.00 (m, 3H), 3.75 (q, J=6.6 Hz, 1H), 3.67 (br., 1H), 3.59–3.49 (m, 2H), 2.48–2.24 (m, 5H), 2.16–2.14 (m, 1H), 2.02–1.92 (m, 2H), 1.21 (t, J=7.2 Hz, 3H), 1.20 (d, J=6.3 Hz, 3H), 1.05 (d, J=6.6 Hz, 3H); $^{13}$C NMR (125 MHz, $CDCl_3$) δ 173.9, 173.0, 172.0, 169.8, 139.0, 138.6, 138.5, 135.9, 128.6, 128.4, 128.3, 128.2, 128.2, 127.9, 127.7, 127.6, 127.5, 127.4, 95.5, 79.2, 76.2, 74.8, 73.4, 73.0, 72.0, 71.0, 66.9, 66.2, 61.5, 59.3, 57.4, 57.2, 35.8, 33.3, 33.2, 29.7, 19.8, 16.7, 16.6, 14.1; MS m/e calc'd for $C_{50}H_{60}O_{12}N_2Cs$ (M+Cs$^+$): 1013.3201, found 1013.3225.

Synthesis of Compound 12 as Illustrated in FIG. 3

12

Compound 12

Compound 11 (16 mg, 0.015 mmole) was dissolved in methanol:$H_2O$ (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P2 (water). The collect fractions were combined and freeze dried to afford the title compound 12 (5.6 mg, 70%). $^1$H NMR (500 MHz, $D_2O$) δ 4.86 (d, J=0.8 Hz, 1 $H_a$), 4.84 (d,J=3.9 Hz, 1 $H_b$), 4.50 (d,J=2.2 Hz, 1 $H_b$), 4.48 (d,J=2.1 Hz, 1 $H_a$), 4.43–4.29 (m, 3H), 4.14–3.99 (m, 2H), 3.71 (dd, J=11.4, 3.9 Hz, 1 $H_b$), 3.64–3.56 (m, 4 $H_b$, 6 $H_a$), 3.49 (dd, J=11.4, 2.7 Hz, 1 $H_b$), 2.53–2.49 (m, 1 $H_a$), 2.43–2.37 (m, 1 $H_b$), 2.28 (t, J=7.3 Hz, 2 $H_b$), 2.30–2.20 (m, 3 Ha), 2.10 (t, J=7.5 Hz, 2 $H_b$), 2.06 (t, J=7.9 Hz, 2 $H_a$), 1.94–1.90 (m, 1 $H_b$), 1.71–1.64 (m, 2 $H_a$, 2 $H_b$), 1.14 (t, J=7.2 Hz, 3 $H_b$), 1.14 (t, J=7.2 Hz, 3 $H_a$), 1.11 (d, J=6.3 Hz, 3 $H_a$), 1.05 (d, J=6.2 Hz, 3 $H_b$), 1.05 (d, J=6.6 Hz, 3 $H_b$), 1.05–1.04 (3 $H_a$); $^{13}$C NMR (125 MHz, $D_2O$) n 182.6, 182.2, 175.9, 175.6, 175.5, 175.3, 172.2, 172.2, 94.9, 94.7, 71.9, 71.3, 70.7, 70.0, 69.7, 69.7, 68.7, 68.0, 67.4, 67.3, 63.4, 63.0, 60.0, 59.6, 58.2, 57.6, 55.5, 55.1, 39.8, 37.4, 36.7, 36.5, 33.9, 33.6, 21.5, 15.6, 14.6, 13.8, 13.7, 13.6; MS m/e calc'd for $C_{22}H_{35}N_2O_{12}$ (M–H)$^-$: 519, found 519.

Figure 4:
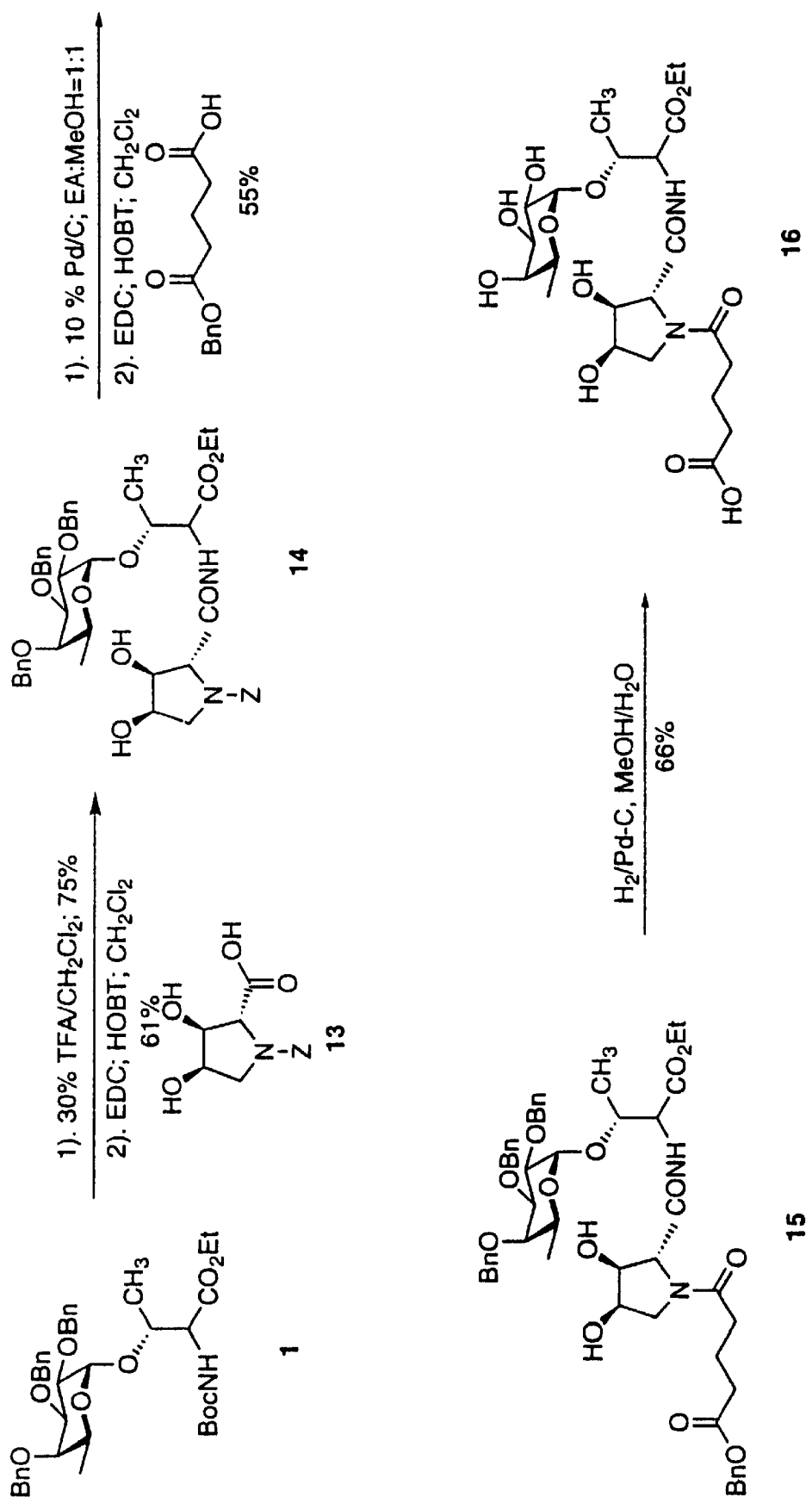
FIG. 4 illustrates the synthesis of fucopeptide 16.

Synthesis of Compound 14 as Illustrated in FIG. 4.

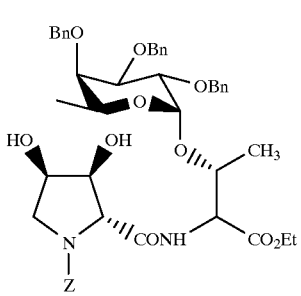

14

Compound 14

A solution of N-Boc-L-threonine esters 1 (30 μmol) dissolved in 30% TFA in $CH_2Cl_2$ (2 mL) was allowed to stand for 30 min at room temperature and evaporated in vacuo. The residue was dissolved in CH₂Cl₂ (1 mL) and neutralized with Et₃N (0.5 mL). To the solution were successively added 1-hydroxybenztriazole (HOBT, 5.4 mg, 40 μmol), 13 (40 μmol; synthesized in pending U.S. application Ser. No. 08/519,203 (TSRI 473.1)) and EDCI (7.7 mg, 40 μmol) at 0° C. The solution was stirred for 1 h at 0° C. and the temperature was allowed to rise to room temperature within 15 h. The reaction mixture was washed with 10% HCl, 5% NaHCO₃ and brine, successively, and dried over MgSO₄. After evaporation in vacuo, the residue was applied to silica gel column chromatography (hexane:EtOAc=1:2) to obtain the compound 14. The FMOC-trans-3,4-dihydroxy-L-proline 13 was prepared as follows: 1.1 equivalents of FMOC-chloride is added to 1.0 equivalents of trans-3,4-dihydroxy-L-proline (Aldrich company) and allowed to stir for 12 hour at 25° C. in 0.10 M methylene chloride. The resulting mixture is quenched with water, washed with sodium bicarbonate and dried over magnesium sulfate (standard workup conditions). The crude compound can then be purified by flash chromatography Synthesis of Compound 15 as Illustrated in FIG. 4

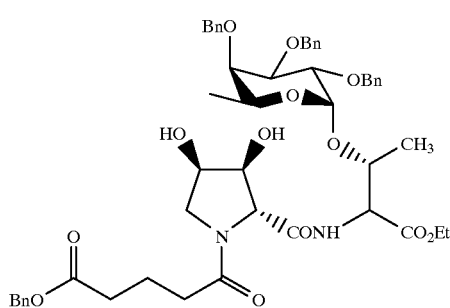

Compound 15

Compound 14 (16 mg, 0.015 mmole) was dissolved in methanol:H₂O (2:1, 2 mL), and then a catalytic amount of Pd on carbon was added. Hydrogen was supplied to the reaction system through a ballon. The reaction was completed in 6 h. The mixture was filtered through celite and concentrated in vacuo. The residue was dissolved in 4 mL THF and then were succesively added benyl monoglutarate (Aldrich), 1-hydroxybeztiazole (HOBT, 73 mg, 0.54 mmole) and 1-(3-dimethylaminopropyl)-3-ethylcarbodiimide (EDC) (104 mg, 0.54 mmole) at 0° C. After being stirred at 0°0 C. for 10 h, the solvent was evaporated and the residue was diluted with EtOAc. The resulting organic layer was washed with H₂O (2×10 mL), 1 N HCl (2×5 mL), saturated aqueous NaHCO₃ (2×5 mL), brine, dried over MgSO₄, filtered and concentrated. The organic residue was purified by flash column chromatography eluting with Toluene:EtOAc (1:1) then (1:2) to afford the product 15. ¹H NMR (500 MHz, CDCl₃) δ 7.58 (d, J=9.5 Hz, 1H), 7.43–7.25 (m, 20H), 5.07 (s, 2H), 4.94 (d, J=11.5 Hz, 1H), 4.85 (d, J=3.7 Hz, 1H), 4.80–4.59 (m, 6H), 4.38 (t, J=7.9 Hz, 1H), 4.30 (d, J=6.3 Hz, 1H), 4.18 (dd, J=10.6, 7.2 Hz, 1H), 4.06–4.03 (m, 2H), 3.99 (dd, J=10.6, 7.2 Hz, 1H), 3.92–3.87 (m, 2H), 3.68–3.63 (m, 2H), 3.51–3.43 (m, 2H), 2.39 (t, J=7.3 Hz, 2H), 2.30–2.22 (m, 2H), 1.91 (t, J=7.1 Hz, 2H), 1.23 (t, J=7.1 Hz, 3H), 1.18 (d, J=6.2 Hz, 3H), 1.05 (d, J=6.4 Hz, 3H); ¹³C NMR (125 MHz, CDCl₃) δ 173.1, 172.0, 170.4, 170.3, 138.4, 138.3, 137.4, 135.9, 128.6, 128.6, 128.5, 128.4, 128.2, 128.2, 128.1, 128.1, 128.0, 127.8, 127.6, 127.5, 93.7, 79.0, 76.0, 74.8, 74.2, 72.6, 71.5, 70.7, 66.6, 66.0, 64.2, 61.5, 56.3, 51.8, 33.1, 32.7, 29.6, 20.0, 19.8, 16.5, 16.1, 14.0; MS m/e calc'd for C₅₀H₆₀N₂O₁₃Cs (M+Cs⁺): 1029.9406, found 1029.9368.

Synthesis of Compound 16 as Illustrated in FIG. 4

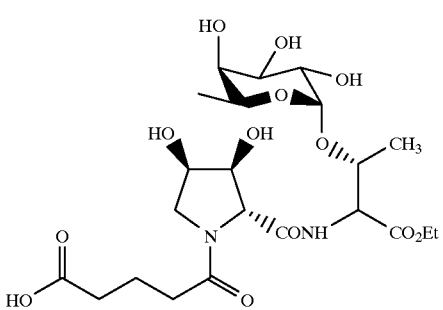

Compound 16

Compound 15 (16 mg, 0.015 mmole) was dissolved in methanol:H₂O (2:1, 2 mL), and then a catalytic amount of Pd(OH)₂ (Degussa type) on carbon was added. Hydrogen was supplied to the reaction system through a ballon. The reaction was completed in 6 h. The mixture was filtered through celite and concentrated in vacuo. The crude product was purified by biogel P2 (water). The collect fractions were combined and freeze dried to afford the title compound 16 (66% yield). ¹H NMR (500 MHz, D₂O) d 4.93 (d, J=3.4 Hz, 1H), 4.46–4.40 (m, 1H), 4.29–4.17 (m, 4H), 4.13–4.08 (m, 1H), 3.81 (dd, J=11.5, 4.4 Hz, 1H), 3.73–3.67 (m, 4H), 3.60–3.58 (m, 2H), 2.39–2.27 (m, 4H), 1.77 (t, J=7.2 Hz, 2H), 1.25–1.19 (m, 6H), 1.15 (d, J=5.8 Hz, 3H); ¹³C NMR (125 MHz, D₂O) δ 171.0, 169.1, 168.9, 167.8, 90.3, 70.7, 67.7, 66.6, 66.4, 65.5, 63.7, 63.1, 63.0, 60.3, 59.0, 53.4, 47.9, 28.6, 16.3, 11.3, 10.0, 9.4; MS m/e calc'd for C₂₂H₃₆N₂O₁₃Cs (M+Cs⁺): 669.1272, found 669.1287.

Figure 5:
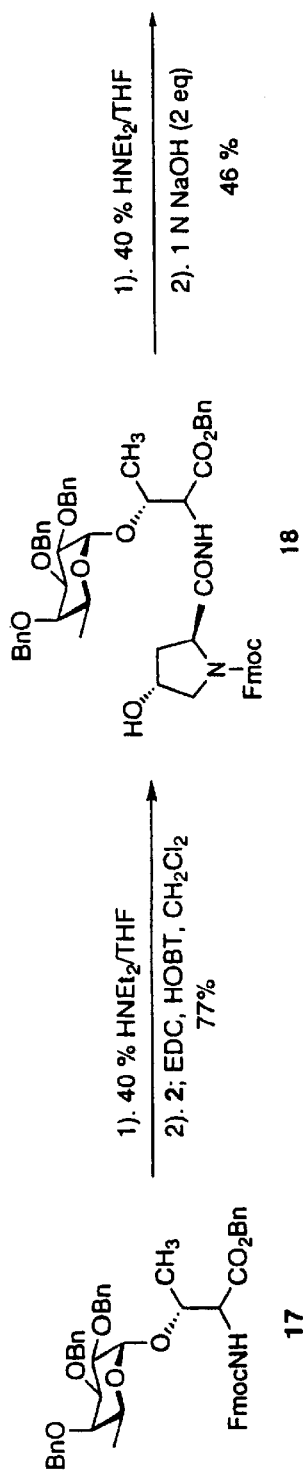
FIG. 5 illustrates the synthesis of fucopeptide 20 and the synthesis of lipid fragment 23.
Figure 5:
Figure 5:
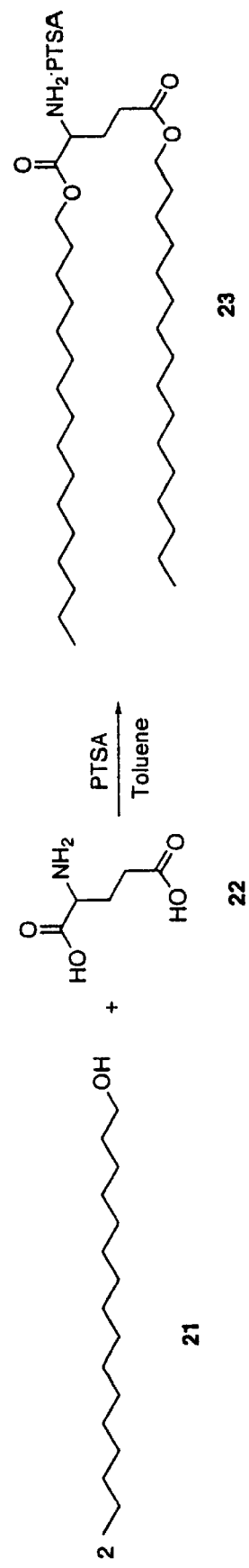

Synthesis of Compound 17 as Illustrated in FIG. 5

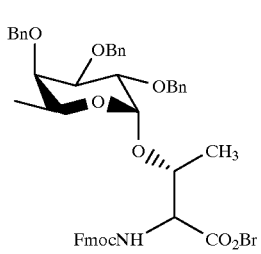

Compound 17

L-Fucose (Sigma) was first converted to tribenzylfucosyl phosphite, from methodology established by Muller et. Al. *Liebigs Ann. Chem.* 1994, 325 and Wong et. Al. *J. Org. Chem.* 1994, 59, 864. The resulting compound (1.0 equivalents) was successfully coupled to Fmoc-L-Thr-OBn (1.1 equivalents; Wong et. al. *J. Org. Chem.* 1994, 59, 864) using trifluromethanesulfonic acid or TMSOTf (0.1 equivalents) as catalyst in methylene chloride at 0° C. to give the Fmoc-L-Thr (tri-o-benzyl-α-Fuc)-OBn (17) in 80% yield after standard workup and purification (1× water, 1× NaHCO₃, brine, dry over sodium sulfate and then flash chromatography).

Synthesis of Compound 18 as Illustrated in FIG. 5

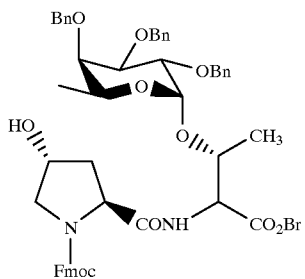

Compound 18

A solution of N-Boc-L-threonine esters 17 (30 μmol) in 40% HNEt (ethylamine; Aldrich chemical company) in THF (10 mL) was allowed to proceed at room temperature for 2 h and evaporated in vacuo The residue was dissolved in $CH_2Cl_2$ (1 mL) and neutralized with $Et_3N$ (0.5 mL). To the solution were successively added 1-hydroxybenztriazole (HOBT, 5.4 mg, 40 μmol), 2 (40 μmol; synthesized infra) and EDCI (7.7 mg, 40 μmol) at 0° C. The solution was stirred for 1 h at 0° C. and the temperature was allowed to rise to room temperature within 15 h. The reaction mixture was washed with 10% HCl, 5% $NaHCO_3$ and brine, successively, and dried over $MgSO_4$. After evaporation in vacuo, the residue was applied to silica gel column chromatography (hexane:EtOAc=1:2) to obtain the compound 18. The FMOC-trans-4-hydroxy-L-proline 2 was prepared as follows: 1.1 equivalents of FMOC-chloride is added to 1.0 equivalents of trans-4-hydroxy-L-proline (Aldrich company) and allowed to stir for 12 hour at 25° C. in 0.10 M methylene chloride. The resulting mixture is quenched with water, washed with sodium bicarbonate and dried over magnesium sulfate (standard workup conditions). The crude compound can then be purified by flash chromatography. Mass Spectral analysis: m/e calc'd for $C_{53}H_{58}O_{11}N_2Cs$ (M+Cs+): 1031.3095, found 1031.3143.

Synthesis of Compound 19 as Illustrated in FIG. 5

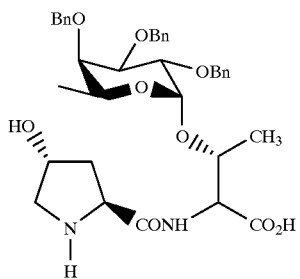

Compound 19

A solution of N-Boc-L-threonine esters 18 (30 μmol) in 40% HNEt (ethylamine; Aldrich chemical company) in THF (10 mL) was allowed to proceed at room temperature for 2 h and evaporated in vacuo. The residue was dissolved in 1N NaOH (2 equivalents) in 0.10 Molar THF and allowed to stir for 12 hour at 0° C. The resulting mixture is then exposed to excess Dowex 50 in methanol for 2 hours and then evaporated in vacuo. The crude compound can then be purified by flash chromatography to yield compound 19 in 46% yield.

Synthesis of Compound 20 as Illustrated in FIG. 5

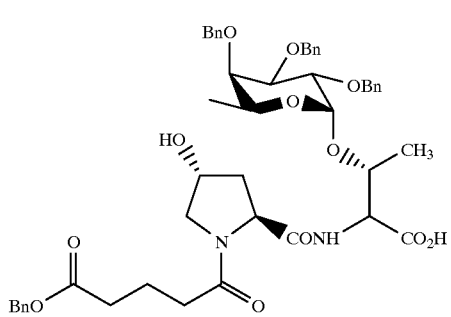

Compound 20

A solution of compound 19 (115 mg, 0.88 mmole) and sodiun hydrogen carbonate (73.5 mg, 0.88 mmole) in water (1 mL) is treated with a solution of 8 (207, 0.58 mmole; formed via addition of 1.1 equivalents succinic anhydride to 1.0 equivalents benyl monoglutarate obtained from Aldrich) in 1,4-dioxane (1 mL). One hour later water (1 mL) was added and the solution was extracted with ether (2×5 mL). The aqueous layer was acidified to pH 2 with 1 N HCl and then extracted with EtOAc (2×5 mL). The organic layer was washed with brine twice, dried over $MgSO_4$, filtered and concentrated. The residue was applied to silica gel column chromatograph ($CHCl_3$:MeOH=4:1) to obtain compound 20. $^1$H NMR (500 MHz, $CDCl_3$) δ 7.36–7.26 (m, 20H), 5.05 (d, J=12.4 Hz, 1H), 5.04 (d, J=12.4 Hz, 1H), 4.88 (d, J=11.5 Hz, 1H), 4.88 (d, J=4.0 Hz, 1H), 4.74–4.65 (m, 4H), 4.60 (d, J=11.6 Hz, 1H), 4.49–4.44 (m, 3H), 4.35 (br., 1H), 4.08 (dd, J=10.1, 4.0 Hz, 1H), 3.80 (q, J=6.3 Hz, 1H), 3.74 (dd, J=10.1, 2.3 Hz, 1H), 3.69 (br., 1H), 3.32–3.30 (m, 1H), 3.09–3.07 (m, 1H), 2.55 (br., 1H), 2.39–2.30 (m, 2H), 2.23–2.19 (m, 1H), 2.15–2.10 (m, 1H), 1.97–1.96 (m, 2H), 1.89–1.82 (m, 2H), 1.24 (d, J=6.3 Hz, 3H), 1.09 (d, J=6.4 Hz, 3H); $^{13}$C NMR (125 MHz, $CDCl_3$) δ 174.0, 173.2, 172.3, 171.2, 138.3, 137.0, 135.9, 128.6, 128.6, 128.5, 128.5, 128.4, 128.4, 128.4, 128.3, 128.3, 128.2, 128.1, 128.1, 128.1, 128.1, 128.0, 128.0, 128.0, 127.8, 127.7, 127.4, 127.0, 92.0, 79.4, 76.0, 74.8, 73.8, 72.1, 66.5, 66.1, 566.5, 66.1, 59.0, 56.8, 56.0, 37.0, 33.3, 33.2, 25.3, 19.9, 16.5, 13.9; MS m/e calc'd for $C_{48}H_{56}O_{12}N_2Cs$ (M+Cs+): 985.2888, found 985.2913.

Synthesis of Compound 23 as Illustrated in FIG. 5

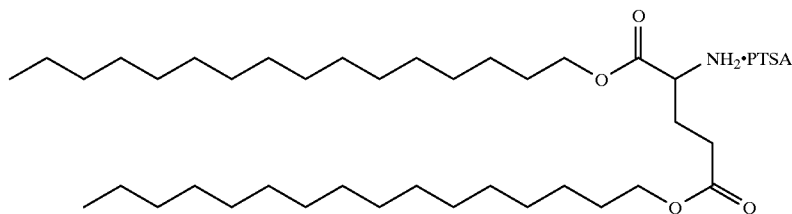

23

Compound 23

The compound is synthesized according to the procedure of Wong et al. JACS 1995, 37, 9515.

Figure 6:
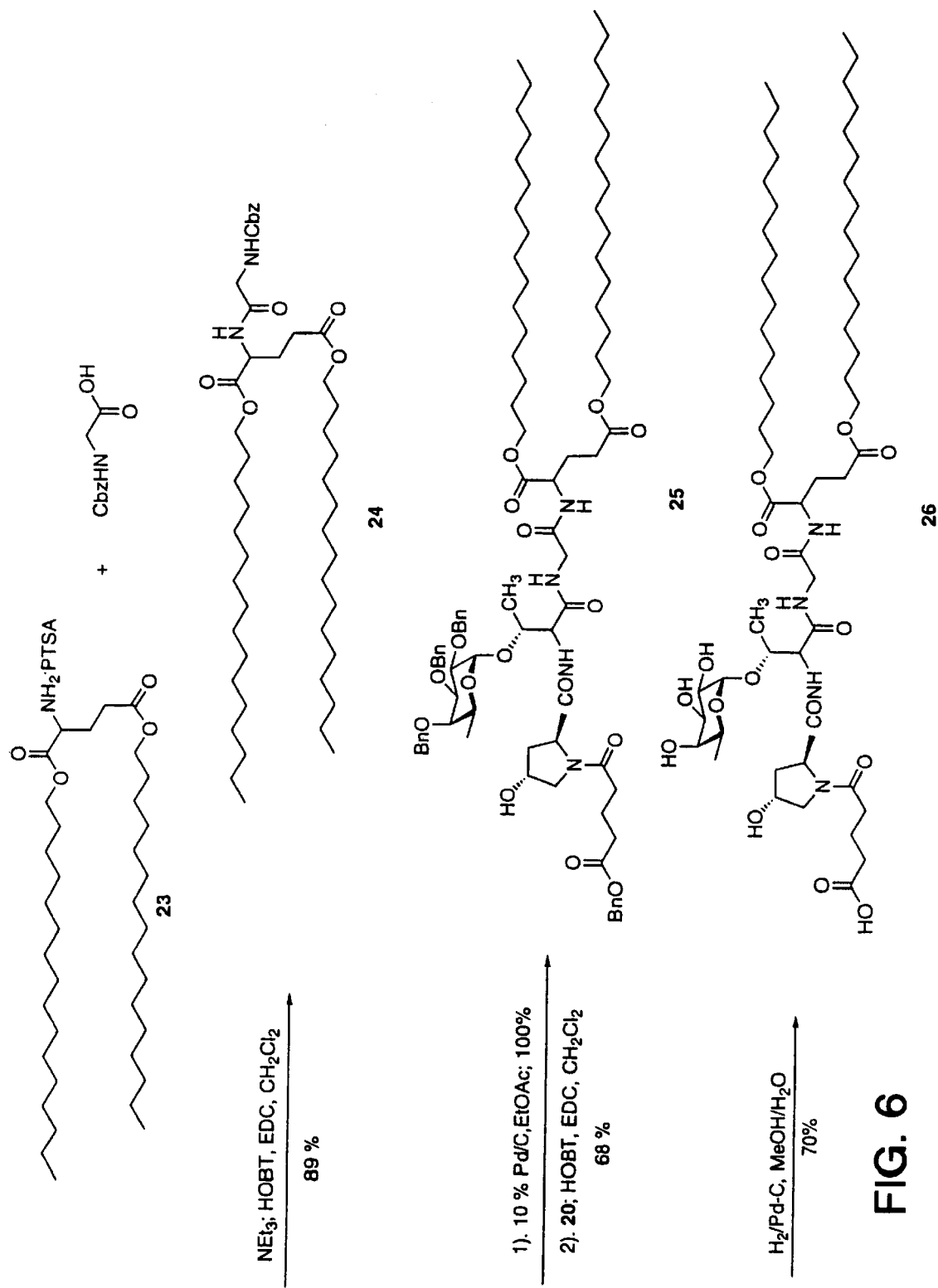
FIG. 6 illustrates the synthesis of liposomic fucopeptide 26.

Synthesis of Compound 24 as Illustrated in FIG. 6

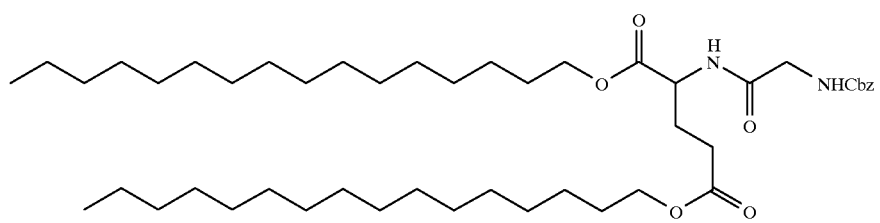

24

Compound 24

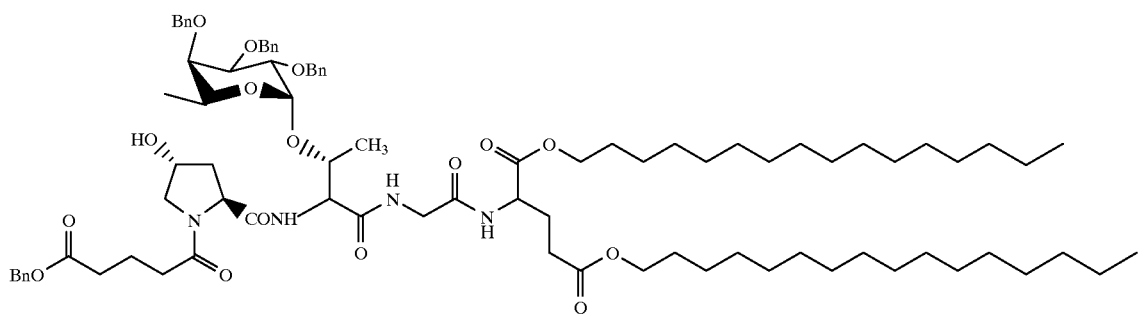

25

Compound 23 was dissolved in CH$_2$Cl$_2$ (1 mL) and neutralized with Et$_3$N (0.5 mL)). To the solution were successively added 1-hydroxybenztriazole (HOBT, 5.4 mg, 40 μmol), carbobenzyloxy(CBZ)-Gly (40 μmol; Aldrich) and EDCI (7.7 mg, 40 μmol) at 0° C. The solution was stirred for 1 h at 0° C. and the temperature was allowed to rise to room temperature within 15 h. The reaction mixture was washed with 10% HCl, 5% NaHCO$_3$ and brine, successively, and dried over MgSO$_4$. After evaporation in vacuo, the residue was applied to silica gel column chromatography (hexane:EtOAc=1:2) to obtain the compound 24 in 89% yield. 1H NMR (500 MHz, CDCl$_3$) δ 7.37–7.31 (m, 5H), 6.73 (d, J=6.8 Hz, 1H), 5.38 (br., 1H), 4.63–4.59 (m, 1H), 4.13 (t, J=6.8 Hz, 2H), 4.05 (t, J=6.8 Hz, 2H), 3.97–3.93 (m, 2H), 2.42–2.31 (m, 2H), 2.24–2.11 (m, 1H), 2.04–1.96 (m, 1H), 1.66–1.57 (m, 4H), 1.28 (br., 52H), 0.88 (t, J=6.7 Hz, 6H); $^{13}$C NMR (125 MHz, CDCl$_3$) δ 173.0, 171.6, 163.1, 128.6, 128.2, 128.1, 67.3, 66.0, 65.1, 57.1, 51.8, 44.4, 31.9, 30.2, 29.7, 29.7, 29.6, 29.5, 29.4, 29.3, 29.2, 28.5, 27.2, 25.9, 25.8, 22.7, 14.1; MS m/e calc'd for C$_{47}$H$_{82}$N$_2$O$_9$Cs (M+Cs$^+$): 919.5176, found 919.5154.

Compound 25

Compound 24 (16 mg, 0.015 mmole) was dissolved in methanol:H$_2$O (2:1, 2 mL), and then a catalytic amount of Pd on carbon was added. Hydrogen was supplied to the reaction system through a ballon. The reaction was completed in 6 h. The mixture was filtered through celite and concentrated in vacuo. The residue was dissolved in 4 mL THF and then were succesively added compound 20, 1-hydroxybeztiazole (HOBT, 73 mg, 0.54 mmole) and 1-(3-dimethylaminopropyl)-3-ethylcarbodiimide (EDC) (104 mg, 0.54 mmole) at 0° C. After being stirred at 0° C. for 10 h, the solvent was evaporated and the residue was diluted with EtOAc. The resulting organic layer was washed with H$_2$O (2×10 mL), 1 N HCl (2×5 mL), saturated aqueous NaHCO$_3$ (2×5 mL), brine, dried over MgSO$_4$, filtered and concentrated. The organic residue was purified by flash column chromatography eluting with Toluene:EtOAc (1:1) then (1:2) to afford the product 25. $^1$H NMR (500 MHz, CDCl$_3$) δ 7.98 (d, J=8.3 Hz, 1H), 7.63 (t, J=6.1 Hz, 1H), 7.42–7.25 (m, 20H), 6.63 (d, J=7.8 Hz, 1H), 5.05 (d, J=12.4

Hz, 1H), 5.04 (d, J=12.4 Hz, 1H), 5.00 (d, J=3.9 Hz, 1H), 4.91 (d, J=11.4 Hz, 1H), 4.81 (d, J=11.5 Hz, 1H), 4.77 (d, J=11.8 Hz, 1H), 4.78 (d, J=11.8 Hz, 1H), 4.61–4.55 (m, 4H), 4.52–4.49 (m, 2H), 4.35 (br., 1H), 4.11–3.94 (m, 9H), 3.87 (q, J=6.4 Hz, 1H), 3.85 (dd, J=10.2, 2.8 Hz, 1H), 3.81–3.76 (m, 1H), 3.66 (d, J=2.8 Hz, 1H), 3.36 (dd, J=11.2, 4.5 Hz, 1H), 3.30–3.27 (m, 1H), 2.35–2.26 (m, 6H), 2.25–2.21 (m, 1H), 2.16–2.11 (m, 1H), 2.08–2.03 (m, 1H), 2.00–1.96 (m, 1H), 1.89–1.85 (m, 1H), 1.83–1.77 (m, 1H), 1.59–1.55 (m, 4H), 1.26 (br., >50), 1.13 (d, J=6.4 Hz, 3H), 0.88 (t, J=6.8 Hz, 6H); $^{13}$C NMR (125 MHz, CDCl$_3$) δ 173.7, 173.2, 173.0, 172.8, 171.3, 170.3, 169.3, 138.9, 138.6, 138.2, 135.8, 128.6, 128.5, 128.5, 128.5, 128.4, 128.4, 128.3, 128.3, 128.2, 128.2, 128.0, 127.9, 127.5, 127.4, 127.2, 92.1, 79.6, 76.6, 74.8, 73.7, 72.6, 69.9, 67.9, 66.8, 66.2, 65.8, 65.0, 59.9, 57.5, 55.1, 51.8, 42.4, 38.4, 33.4, 33.1, 31.9, 30.2, 29.8, 29.8, 29.7, 29.7, 29.6, 29.5, 29.4, 29.3, 29.3, 29.2, 28.5, 28.4, 27.3, 25.9, 25.8, 22.7, 19.7, 16.6, 14.1, 14.1, 14.0; MS m/e calc'd for $C_{87}H_{130}N_4O_{16}Cs$ (M+Cs$^+$): 1619.8536, found 1619.858.

Synthesis of Compound 26 as Illustrated in FIG. 6

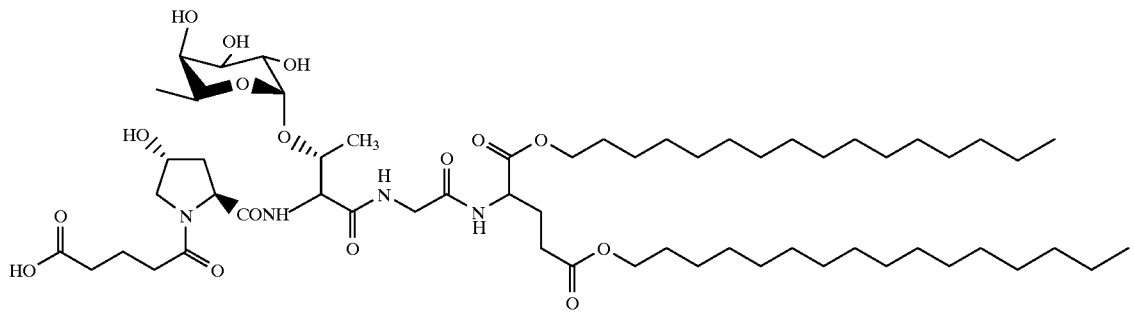

26

Compound 26

Compound 25 (16 mg, 0.015 mmole) was dissolved in methanol:H$_2$O (2:1, 2 mL), and then a catalytic amount of Pd on carbon was added. Hydrogen was supplied to the reaction system through a ballon. The reaction was completed in 6 h. The mixture was filtered through celite and concentrated in vacuo. The crude product was purified by biogel P2 (water). The collect fractions were combined and freeze dried to afford the title compound 26 in 70% yield.

Figure 7:
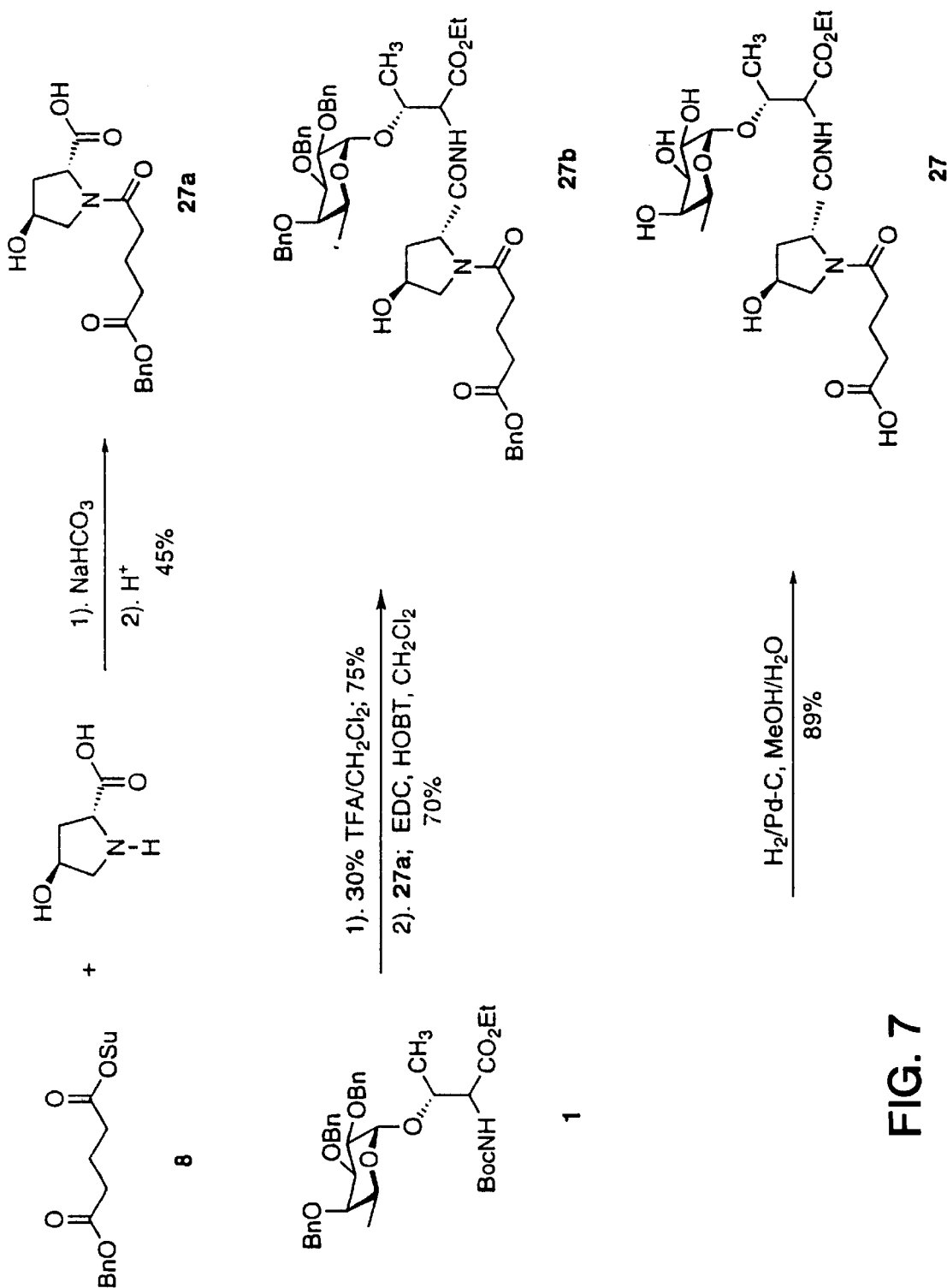
FIG. 7 illustrates the synthesis of fucopeptide 27.

Synthesis of Compound 27(a) as Illustrated in FIG. 7

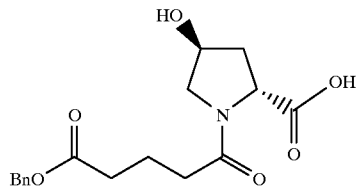

27a

Compound 27(a)

A solution of trans-4-hydroxy-L-proline 9 (115 mg, 0.88 mmole; Aldrich) and sodiun hydrogen carbonate (73.5 mg, 0.88 mmole) in water (1 mL) is treated with a solution of 8 (207, 0.58 mmole; formed via addition of 1.1 equivalents succinic anhydride to 1.0 equivalents benyl monoglutarate obtained from Aldrich) in 1,4-dioxane (1 mL). One hour later water (1 mL) was added and the solution was extracted with ether (2×5 mL). The aqueous layer was acidified to pH 2 with 1 N HCl and then extracted with EtOAc (2×5 mL). The organic layer was washed with brine twice, dried over MgSO$_4$, filtered and concentrated. The residue was applied to silica gel column chromatograph (CHCl$_3$:MeOH=4:1) to obtain compound 27(a).

Synthesis of Compound 27(b) as Illustrated in FIG. 7

27b

Compound 27(b)

A solution of N-Boc-L-threonine ester 1 (30 μmol) dissolved in 30% TFA in CH$_2$Cl$_2$ (2 mL) was allowed to stand for 30 min at room temperature and evaporated in vacuo. The residue was dissolved in CH$_2$Cl$_2$ (1 mL) and neutralized with Et$_3$N (0.5 mL). To the solution were successively added 1-hydroxybenztriazole (HOBT, 5.4 mg, 40 μmol), 27a (40 μmol; synthesized supra) and EDCI (7.7 mg, 40 μmol) at 0° C. The solution was stirred for 1 h at 0° C. and the temperature was allowed to rise to room temperature within 15 h. The reaction mixture was washed with 10% HCl, 5% NaHCO$_3$ and brine, successively, and dried over MgSO$_4$. After evaporation in vacuo, the residue was applied to silica gel column chromatography (hexane:EtOAc=1:2) to obtain the compound 27b.

Synthesis of Compound 27 as Illustrated in FIG. 7

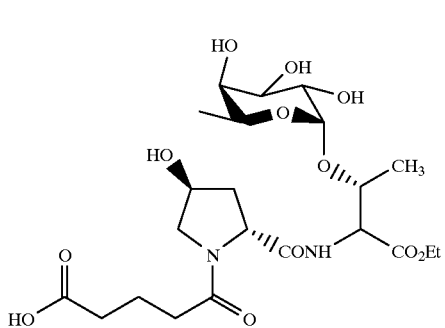

27

Compound 27

Compound 27(b) (16 mg, 0.015 mmole) was dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P2 (water). The collect fractions were combined and freeze dried to afford the title compound 27 (5.6 mg, 70%).

Figure 8:
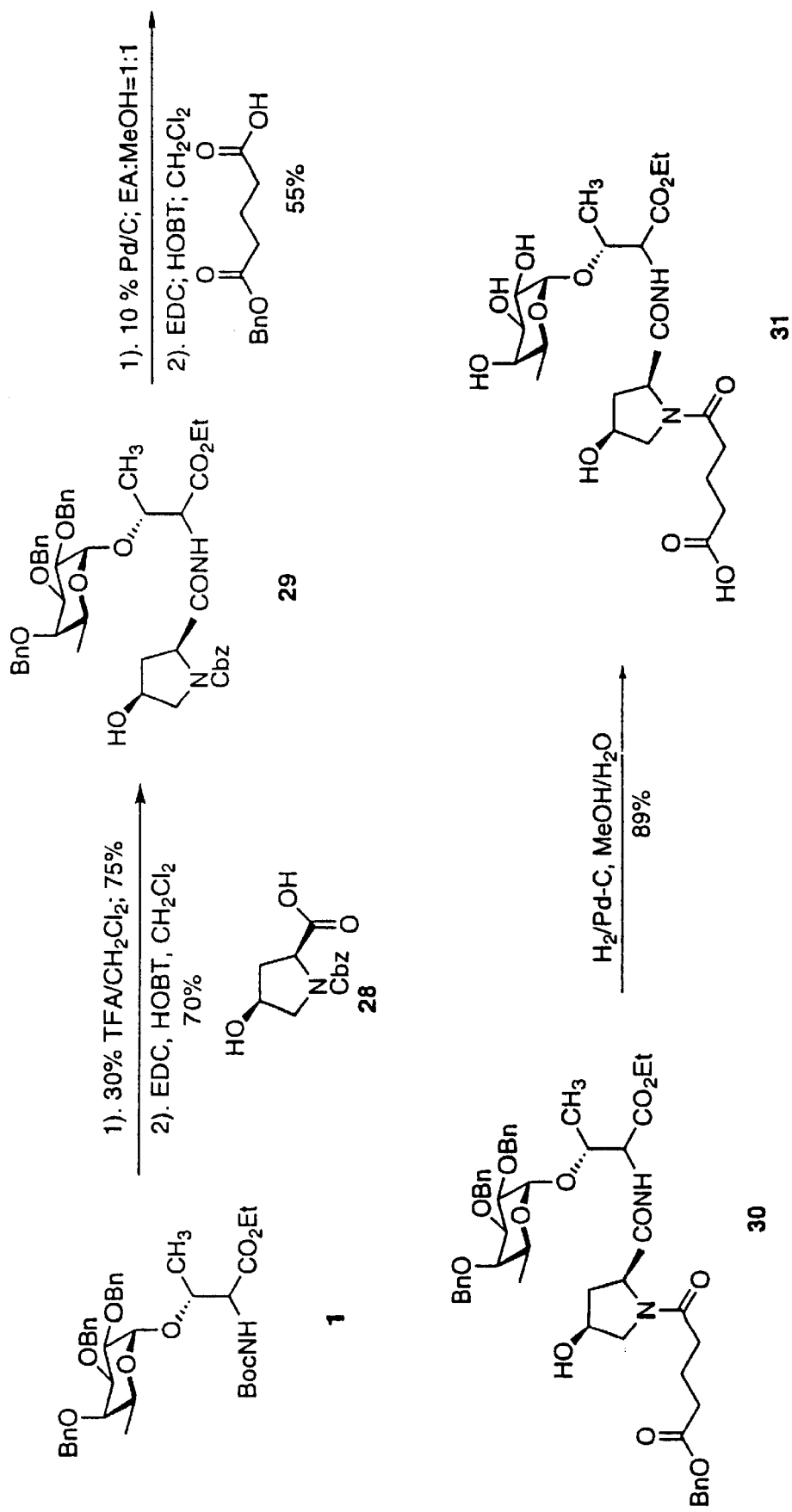
FIG. 8 illustrates the synthesis of fucopeptide 31.

Synthesis of Compound 29 as Illustrated in FIG. 8

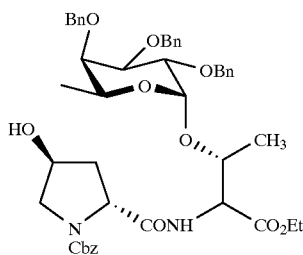

29

Compound 29

A solution of N-Boc-L-threonine esters 1 (30 μmol) dissolved in 30% TFA in CH$_2$Cl$_2$ (2 mL) was allowed to stand for 30 min at room temperature and evaporated in vacuo. The residue was dissolved in CH$_2$Cl$_2$ (1 mL) and neutralized with Et$_3$N (0.5 mL). To the solution were successively added 1-hydroxybenztriazole (HOBT, 5.4 mg, 40 μmol), CBZ-cis-4-hydroxy-L-proline 28 (40 μmol; synthesized infra) and EDCI (7.7 mg, 40 μmol) at 0° C. The solution was stirred for 1 h at 0° C. and the temperature was allowed to rise to room temperature within 15 h. The reaction mixture was washed with 10% HCl, 5% NaHCO$_3$ and brine, successively, and dried over MgSO$_4$. After evaporation in vacuo, the residue was applied to silica gel column chromatography (hexane:EtOAc 1:2) to obtain the compound 29. The CBZ-cis-4-hydroxy-L-proline 28 was prepared as follows: 1.1 equivalents of (carbobenzyoxy)CBZ-chloride (Aldrich company) is added to 1.0 equivalents of cis-4-hydroxy-L-proline (Aldrich company) and allowed to stir for 12 hour at 25° C. in 0.10 M methylene chloride. The resulting mixture is quenched with water, washed with sodium bicarbonate and dried over magnesium sulfate (standard workup conditions). The crude compound can then be purified by flash chromatography Synthesis of Compound 30 as Illustrated in FIG. 8

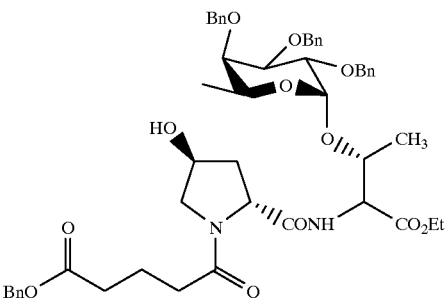

30

Compound 30

Compound 29 (16 mg, 0.015 mmole) was dissolved in methanol:H$_2$O (2:1, 2 mL), and then a catalytic amount of Pd on carbon was added. Hydrogen was supplied to the reaction system through a ballon. The reaction was completed in 6 h. The mixture was filtered through celite and concentrated in vacuo. The residue was dissolved in 4 mL THF and then were succesively added benyl monoglutarate (Aldrich), 1-hydroxybeztiazole (HOBT, 73 mg, 0.54 mmole) and 1-(3-dimethylaminopropyl)-3-ethylcarbodiimide (EDC) (104 mg, 0.54 mmole) at 0° C. After being stirred at 0° C. for 10 h, the solvent was evaporated and the residue was diluted with EtOAc. The resulting organic layer was washed with H$_2$O (2×10 mL), 1 N HCl (2×5 mL), saturated aqueous NaHCO$_3$ (2×5 mL), brine, dried over MgSO$_4$, filtered and concentrated. The organic residue was purified by flash column chromatography eluting with Toluene:EtOAc (1:1) then (1:2) to afford the product 30.

Synthesis of Compound 31 as Illustrated in FIG. 8

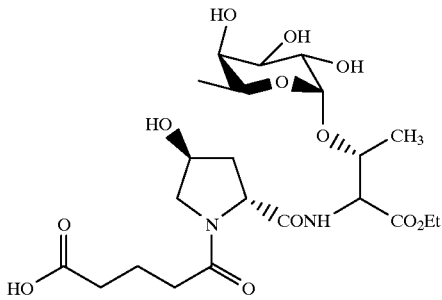

31

Compound 31

Compound 30 (16 mg, 0.015 mmole) was dissolved in methanol:H$_2$O (2:1, 2 mL), and then a catalytic amount of Pd(OH)$_2$ (Degussa type) on carbon was added. Hydrogen was supplied to the reaction system through a ballon. The reaction was completed in 6 h. The mixture was filtered through celite and concentrated in vacuo. The crude product was purified by biogel P2 (water). The collect fractions were combined and freeze dried to afford the title compound 31. (89% yield).

Figure 9:
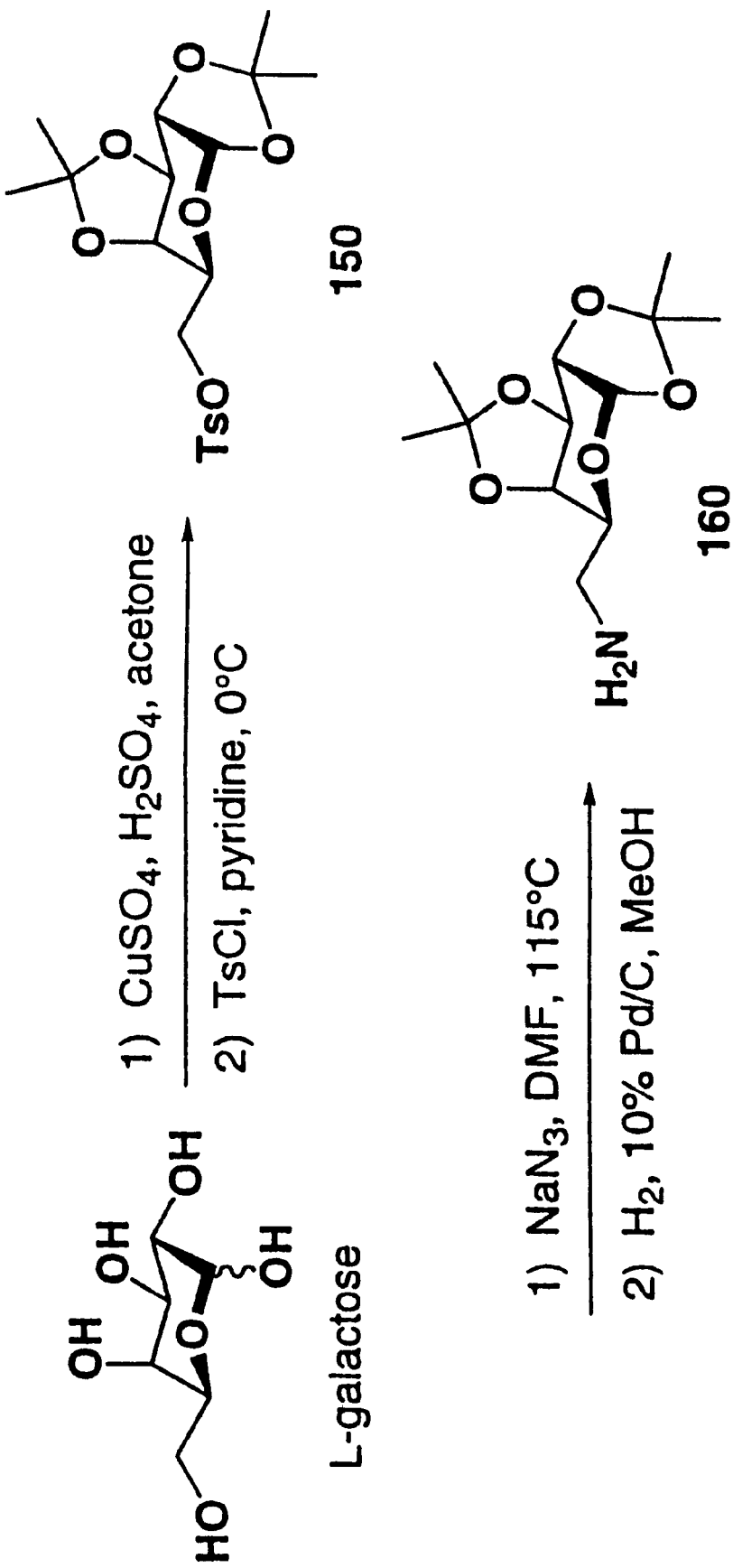
FIG. 9 illustrates the preparation of the galactose amine core 160.

Synthesis of 6-Amino-6-Deoxy-1,2:3,4-Di-O-Isopropylidene-α-L-Galactopyranoside (160) as Illustrated in FIG. 9

Aminoglycoide 160 was prepared exactly as described in May et al. *J. Med. Chem.* 1979, 22, 971.

Figure 10:
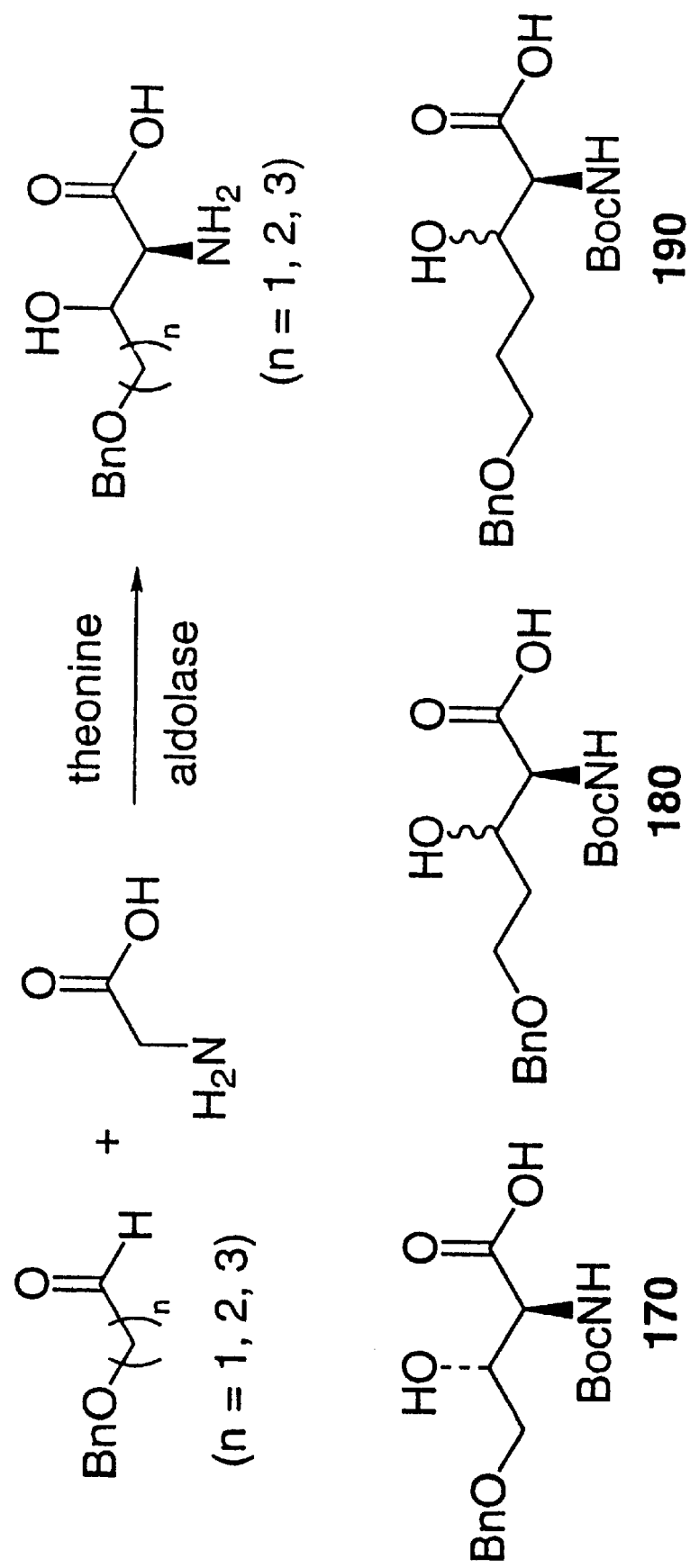
FIG. 10 illustrates the synthesis of amino acid's 170–190.

Synthesis of 2-Amino-4-Benzyloxy-3-Hydroxy Alkanoic Acids as Shown in FIG. 10

The amino acids 170, 180, and 190 were synthesized via a threonine aldolase catalyzed reaction of glycine with the appropriately protected hydroxyl aldehyde following exactly the published literature procedure as described in Vassilev et al. *Tetrahedron Lett.* 1995, 36, 4081. The resulting benzyl protected dihydroxy amino acids were treated with BOC-anhydride as described below affording amino acids 170 (99%), 180 (83%), and 190 (85%) in high yield. Amino acids 180 and 190 were isolated as a 1:1 mixture about the 2° OH center and were carried on without separation.

BOC Protection of 2-Amino-4-Benzyloxy-3-Hydroxy Alkanoic Acids to Form (2S, 3R) 2-Amino-4-Benzyloxy-3-Hydroxybuteric Acid (170) and Related Compounds 180 and 190 as Illustrated in FIG. 10

A solution of di-tert butyl dicarbonate (524 mg, 2.4 mmol; Aldrich) in dioxane (10 mL) was added to a stirred solution of (2S, 3R) 2-amino-4-benzyloxy-3-hydroxy butanoic acid (for 170) (450 mg, 2.0 mmol; use ) in $H_2O$ (10 mL) containing $Et_3N$ (310 μL, 2.2 mmol) at 23° C. After 10 h, the mixture was poured into $Et_2O/H_2O$ (1:1, 100 mL) and the upper organic layer discarded. The lower aqueous layer was washed with $Et_2O$ (3×50 mL) and then acidified to pH 3 using 1 M HCl solution. The acidic solution was then extracted with EtOAc (5×30 mL). The combined organic extracts were washed with saturated $NaHCO_3$ (3×25 mL), dried ($MgSO_4$) and evaporated giving 170 (644 mg, 99%) as a colorless oil: $[\alpha]_D$+27 (c. 1.02 in $CHCl_3$); $^1H$ NMR (250 MHz; $CD_3OD$) δ 7.38–7.22 (5H, m, aromatic), 4.54 (2H, s, $OCH_2Ph$), 4.32 (1H, br d, J=4.9, H2), 4.07 (1H, q, J=5.0, H3), 3.62 (1H, dd, J=10.1 and 4.7, $H4_aH4_b$), 3.56 (1H, dd, J=10.1 and 5.6, $H4_aH4_b$), 1.32 (9H, s, $^tBu$); $^{13}C$ NMR (63 MHz; $CD_3OD$) δ 173.86, 157.95, 139.48, 129.34, 128.87, 128.66, 80.73, 74.41, 72.46, 71.70, 57.93, 28.68; HRMS (FAB, Doped with CsI) Found: M+Cs$^+$, 458.0590. $C_{16}H_{23}NO_6$ requires M+Cs$^+$ 458.0580.

DATA for (2S, 3R and 3S) 2-Amino-5-Benzyloxy-3-Hydroxypropionic Acid (180)

As for 170 above to giving 180 as a colorless oil (83%): $^1H$ NMR (250 MHz; $CD_3OD$) δ 7.22–7.11 (5H, m, aromatics), 4.39 (1H, s, $CH_2Ph$), 4.38 (1H, s, $CH_2Ph$), 4.22–4.18 (0.5H, m, H2), 4.08–4.05 (1H, m, H2+H3), 3.96–3.89 (0.5H, m, H3), 3.56–3.44 (2H, m, 2×$C5H_2$), 1.78–1.59 (2H, m, 2×$C4H_2$), 1.32 (9H, m, 2×$^tBu$); $^{13}C$ NMR (63 MHz; $CD_3OD$) δ 174.54, 173.49, 156.35, 156.13, 137.42, 128.48, 127.80, 80.51, 80.25, 73.27, 71.80, 71.27, 68.45, 67.99, 58.10, 57.61, 32.71, 28.25; HRMS (FAB, Doped with CsI): Found M+Cs, 472.0728. $C_{17}H_{25}NO_6$ requires M+Cs, 472.0736.

DATA for (2R, 3R and 3S) 2-Amino-6-Benzyloxy-3-Hydroxyhexanoic Acid (190)

As for 170 above to give 190 as a colorless oil (85%): $^1H$ NMR (250 MHz; $CD_3OD$) δ 7.23–7.13 (5H, m, aromatics), 4.38 (2H, s, 2×$CH_2Ph$), 4.07–3.97 (1.5H, m, 2×H2+H3), 3.72–3.68 (0.5H, m, H3), 3.43–3.38 (2H, m, $C6H_2$), 1.67–1.46 (4H, m, 2×H4+2×H5), 1.33 (9H, s, 2×$^tBu$); $^{13}C$ NMR (63 MHz; $CD_3OD$) δ 174.57, 173.40, 156.38, 156.14, 137.63, 128.40, 127.79, 80.18, 72.89, 71.65, 70.00, 58.12, 57.61, 30.79, 30.46, 28.23, 26.07; HRMS (FAB, Doped with CsI): Found M+Cs, 486.0914. $C_{18}H_{27}NO_6$ requires M+Cs, 486.0893.

Figure 11:
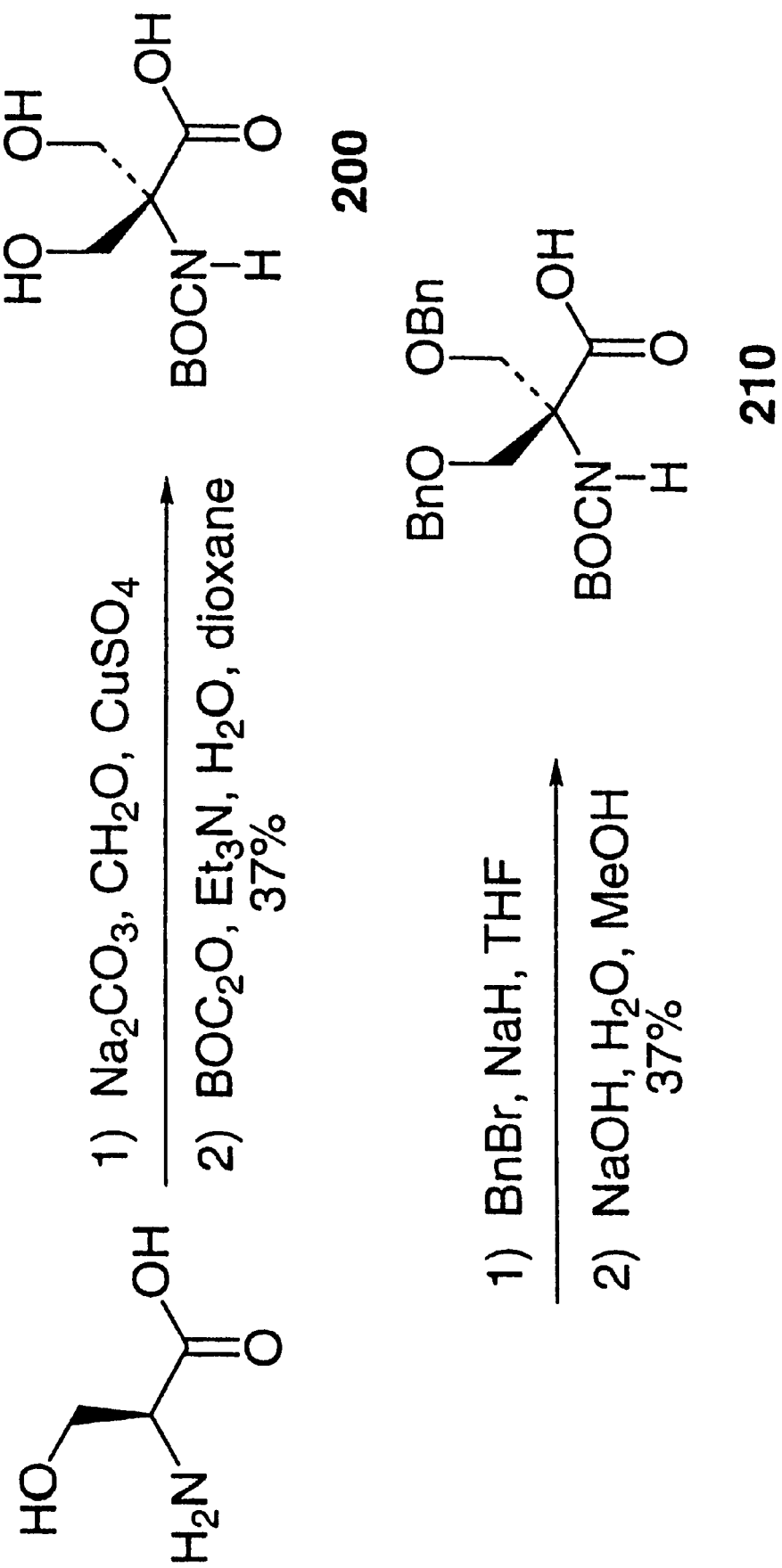
FIG. 11 illustrates the synthesis of dihydroxy amino acid 210.

Synthesis of Amino Acid 210 as Illustrated in FIG. 11

Amino acid 210 was prepared synthetically as shown in FIG. 11 following the procedure described exactly by Otani et al. *Biochm. Biophys.* 1960, 90, 254. Treatment of serine with $Na_2CO_3$ and formaldehyde in the presence of $CuSO_4$ afforded the desired diol which was converted to the BOC derivative 200 (see also Nakamura et al. *Bull. Chem. Soc. Jpn* 1994, 67, 2151) in 37% yield for this two-step conversion. Standard perbenzylation with excess BnBr and (2.2 equivalents of NaH) in 0.50 Molar THF followed by simple hydrolysis of the ester using 10% sodium hydroxide in 1:1 methanol water (0.1 Molar total) and subsequent work-up acidification using dilute HCl afforded the protected amino acid 210 in 37% yield which was used in the subsequent coupling studies.

Figure 12:
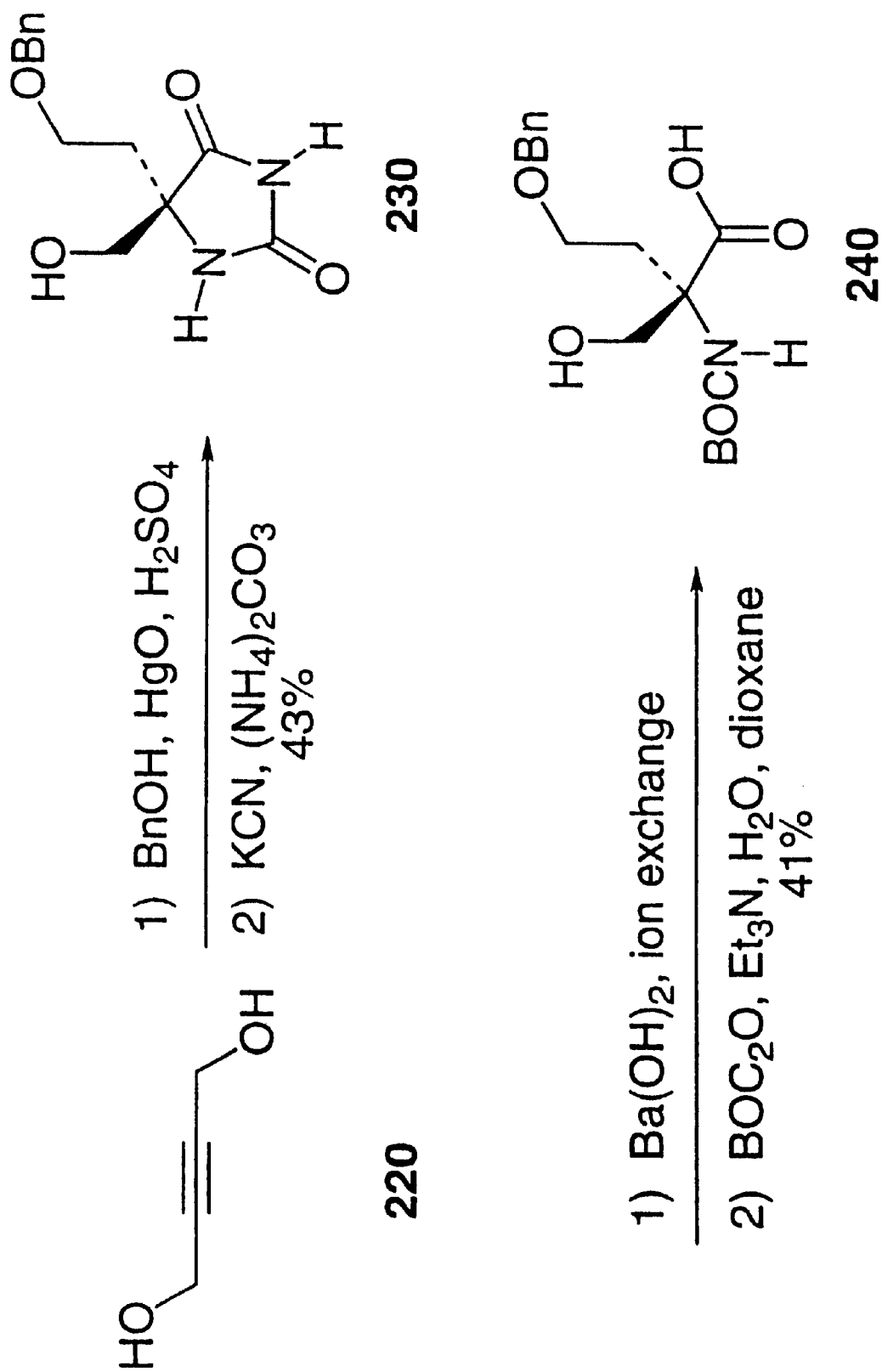
FIG. 12 illustrates the synthesis of amino acid 240.

Synthesis of 1-Hydroxymethyl-1-Benzyloxyethylhydantoin (230) as Illustrated in FIG. 12

The ketone intermediate was synthesized from 2-butyne-1,4-diol 220 (1.004 g, 11.66 mmol; Aldrich) according to the exact procedure as described by Hennion et al. *J. Org. Chem.* 1953, 18, 1601, with one exception: instead of EtOH, BnOH (3.33 mL total) was used. When the conversion was complete, the mixture was extracted with $CH_2Cl_2$ (3 times) and the collected organic layers were washed with 1 M $Na_2CO_3$, 1 N HCl, brine, dried ($MgSO_4$) and concentrated under vacuum silica gel column chromatography (EtOAc/hexanes, 3:7) affording the intermediate as a colorless oil in 54% yield (1.217 g): $^1H$ NMR (250 MHz, $CDCl_3$) δ 2.68 (t, 2H, J=6.0 Hz, $COCH_2CH_2$), 3.17 (br, 1H, OH), 3.76 (t, 2H, J=6.0 Hz, $CH_2O$), 4.28 (s, 2H, $CH_2OH$), 4.50 (s, 2H, $CH_2Ph$), 7.25–7.38 (m, 5H, Ph); $^{13}C$ NMR (63 MHz, $CDCl_3$) δ 38.83, 64.80, 68.70, 73.12, 127.55, 127.66, 128.32, 137.57, 208.38.

The above ketone (1.00 g, 5.15 mmol) was converted to the hydantoin 230 following the exact procedure described by Krüger et al. *Houben-Weyl: Methoden der Organischen Chemie, Band E5*; Falb, J., Ed.; Dusseldorf, 1995, 504. Recrystallization from EtOH/$H_2O$ afforded 230 (1.092 g, 80% yield): m.p. 157.5° C.–158.5° C.; $^1H$ NMR (400 MHz, MeOD/$CDCl_3$) δ 2.12, 2.24 (m 8 lines ($H_a$), dt ($H_b$), 2H, $J_{AX}$=5.9 Hz, $J_{AY}$=8.3 Hz, $J_{BX}$=4.6 Hz, $J_{AB}$=14.3 Hz, $CCH_2$), 3.59–3.63 (m, 2H, $CH_2O$), 4.31, 4.55 (two d, 2H, J=9.1 Hz, $CH_2OH$), 4.48, 4.52 (two d, 2H, J=11.9 Hz, $CH_2Ph$), 7.28–7.38 (m, 5H, Ph); $^{13}C$ NMR (100 MHz, $CDCl_3$) δ 36.15, 63.40, 65.72, 72.98, 73.30, 127.36, 127.42, 127.96, 128.03, 137.06, 159.01, 175.28; HRMS calcd for $C_{13}H_{16}N_2O_4$ (M+H$^+$): 265.1188; found 265.1184.

Synthesis of N-Butyloxycarbonyl-1-Benzyloxyethylserine (240) as Illustrated in FIG. 12

The title amino acid was prepared from the hydantoin 230 (0.695 g, 2.63 mmol) by hydrolysis using Ba(OH)$_2$ following the exact procedure described by Krüger et al. *Houben-Weyl: Methoden der Organischen Chemie, Band E5*; Falb, J., Ed.; Dusseldorf, 1995, 504. After a reaction time of 48 h, 1 M NaHCO$_3$ was added and the precipitate was filtered. The filtrate was evaporated to a small volume under reduced pressure and acidified with HOAc to pH 3. Ion exchange column chromatography (Dowex 50W H$^+$, gradient of 0.5 N NH$_4$OH), followed by lyophilization afforded the product (0.583 g, 93%) as a white solid: $^1H$ NMR (250 MHz, $D_2O$, Ref. $CH_3CN$) δ 1.78–2.07 (m, 2H, $CCH_2CH_2$), 3.55, 3.81 (two d, 2H, J=11.4 Hz, $CH_2OH$), 3.62–3.67 (m, 2H, $CH_2O$), 4.54 (s, 2H, $CH_2Ph$), 7.35–7.47 (m, 5H, Ph); $^{13}C$ NMR (63 MHz, $D_2O$, Ref. $CH_3CN$) δ 34.27, 64.00, 67.38, 67.62, 73.62, 129.02, 129.22, 129.46, 138.05, 179.33; HRMS calcd for $C_{12}H_{17}NO_4$ (M+Na$^+$): 262.1055; found 262.1060.

The above amino acid (92 mg, 0.385 mmol) was dissolved in a mixture of $H_2O$ (1 mL) and dioxane (1 mL). Triethylamine (64 μL, 0.46 mmol) and Boc$_2$O (101 mg, 0.46 mmol) were added and the mixture was stirred for 2 days at 23° C., during which time 3 additional portions of Boc$_2$O (101 mg, 0.46 mmol) and Et$_3$N (64 mg, 0.46 mmol) were added. The dioxane was evaporated under reduced pressure and the residue was acidified with 1 N HCl to pH 3 and extracted with CH$_2$Cl$_2$ (3×5 mL). The collected organic layers were washed with brine, dried (MgSO$_4$) and concentrated under reduced pressure. Purification by column chromatography (CH$_2$Cl$_2$/MeOH, 96:4) afforded 240 as an oil (57 mg, 44%): $^1$H NMR (250 MHz, CDCl$_3$) δ 1.42 (s, 9H, C(CH$_3$)$_3$), 2.15–2.34 (m, 2H, CCH$_2$), 3.59–3.63 (m, 2H, CH$_2$CH$_2$O), 3.83, 4.03 (two d, 2H, J=11.0 Hz, CH$_2$OH), 4.45, 4.51 (two d, 2H, J=11.7 Hz, CH$_2$Ph), 5.50 (br, 1H, COOH), 6.25 (br, 1H, NH), 7.26–7.35 (m, 5H, Ph); $^{13}$C NMR (63 MHz, CDCl$_3$) δ 28.25, 32.35, 63.62, 66.25, 73.20, 80.15, 127.73, 128.40, 137.51, 155.93, 175.95; HRMS calcd for C$_{17}$H$_{25}$NO$_6$ (M+Na$^+$): 362.1580; found 362.1573.

General Coupling of N-Protected Amino Acids 180, 190, 210, and 240 to 6-Amino-6-Deoxy-1,2:3,4-Di-O-Isopropylidene-α-L-Galactopyranose (160) to Form Mimetic Compounds 250–290 as Illustrated in FIG. 13

The following coupling and deprotection procedure is identical to that which was used in the synthesis of all compounds 250–290.

Representative Synthesis of Glycpeptide 250 as Illustrated in FIG. 13

1-(3-Dimethylaminopropyl)-3-ethylcarbodiimide hydrochloride (EDCI) (124 mg, 0.65 mmol) was added to a stirred solution of 6-amino-6-deoxy-1,2:3,4-diisopropylidene-α-L-galactopyranoside 160 (155 mg, 0.6 mmol), N-Boc amino acid 170 (211 mg, 0.65 mmol), 1-hydroxy benzotriazole (HOBt) (88 mg, 0.65 mmol) and 4-methyl morpholine (143 µL, 1.3 mmol ) in dry DMF (2 mL) under argon at −20° C. The resulting mixture was stirred at −20° C. for 1 h and then allowed to warm slowly to 23° C. After 14 h, the reaction solution was quenched with a 5% citric acid solution (20 mL) and extracted with EtOAc (6×25 mL). The combined organic extracts were washed with saturated NaHCO$_3$ solution (50 mL), a saturated NaCl solution (50 mL), dried (MgSO$_4$) and evaporated down under reduced pressure. The residual oil was purified by silica gel flash chromatography (40%Æ50%Æ66% EtOAc in hexanes) to give the product (287 mg, 84%) as a white amorphous foam: [α]$_D$+7.4 (c. 1.02 in CHCl$_3$); $^1$H NMR (400 MHz; CDCl$_3$) δ 7.33–7.25 (5H, m, aromatic), 6.72 (1H, m, C6NH), 5.62 (1H, br d, J=7.4, C2'NH), 5.49 (1H, d, J=5.0, H1), 4.56 (1H, dd, J=7.9 and 2.4, H3), 4.55 (2H, s, OCH$_2$Ph), 4.28 (1H, dd, J=5.0 and 2.4, H2), 4.23–4.20 (1H, br m, H2'), 4.16 (1H, dd, J=7.9 and 1.8, H4), 3.95–3.91 (2H, m, H5+H3'), 3.66 (1H, ddd, J=14.0, 7.5 and 3.6, H6$_a$H6$_b$), 3.65–3.58 (2H, m, C4'H$_2$), 3.46 (1H, br d, J=7.0, C3'OH), 3.17 (1H, ddd, J=14.0, 9.1 and 4.5, H6$_a$H6$_b$), 1.45 (3H, s, acetonide Me), 1.43 (3H, s, acetonide Me), 1.41 (9H, s, $^t$Bu), 1.31 (3H, s, acetonide Me), 1.28 (3H, s, acetonide Me); $^{13}$C NMR (100 MHz; CDCl$_3$) δ 170.64, 155.60, 137.77, 128.41, 128.22, 127.84, 109.48, 108.79, 96.37, 79.95, 73.45, 71.76, 71.48, 71.45, 70.80, 70.43, 65.63, 55.75, 40.03, 28.26, 25.93, 24.88, 24.32; IR 3349, 2979, 2933, 1712, 1666, 1497, 1454, 1382, 1369, 1253, 1211, 1167, 1110, 1070, 1006, 901, 859, 736, 698 cm$^{-1}$; HRMS (FAB, Doped with CsI) Found: M+Cs$^+$, 699.1876. C$_{28}$H$_{42}$N$_2$O$_{10}$ requires M+Cs$^+$ 699.1894; Elemental Analysis Found: C, 59.07; H, 7.39; N, 4.94. C$_{28}$H$_{42}$N$_2$O$_{10}$ requires C, 59.35; H, 7.47; N, 4.94.

A solution of the above glycopeptide (187 mg, 322 µmol) with 10% TFA in dry CH$_2$Cl$_2$ (2 mL) was stirred under argon at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give 250 (108 mg, 70%): [α]$_D$+ 2.6 (c. 2.22 in CHCl$_3$); $^1$H NMR (400 MHz; CDCl$_3$) δ 7.51 (1H, br dd, J=7.3 and 4.4, C6NH), 7.31–7.21 (5H, m, aromatic), 5.45 (1H, d, J=5.0, H1), 4.54 (1H, d, J=11.9, OCH$_a$H$_b$Ph), 4.52 (1H, dd, J=7.9 and 2.4, H3), 4.45 (1H, d, J=11.9, OCH$_a$H$_b$Ph), 4.24 (1H, dd, J=5.0 and 2.4, H2), 4.13 (1H, dd, J=7.9 and 1.7, H4), 3.88–3.83 (2H, m, H5+H3'), 3.66–3.55 (2H, m, H6$_a$H6$_b$+C4'H$_2$), 3.41 (1H, d, J 11.9, H2'), 3.17 (1H, ddd, J=14.0, 9.1 and 4.4, C6H$_a$H$_b$), 2.80–1.50 (2H, br s, C2'NH$_2$), 1.42 (3H, s, acetonide Me), 1.40 (3H, s, acetonide Me), 1.27 (3H, s, acetonide Me), 1.25 (3H, s, acetonide Me); $^{13}$C NMR (100 MHz; CDCl$_3$) δ 174.27, 137.93, 128.39, 127.68, 127.65, 109.38, 108.70, 96.28, 73.41, 72.26, 71.59, 71.42, 70.76, 70.46, 66.16, 56.58, 39.70, 25.95, 25.93, 24.91, 24.29; IR 3367, 2986, 2932, 1654, 1529, 1454, 1382, 1254, 1211, 1166, 1108, 1068, 1005, 900, 738, 698 cm$^{-1}$; HRMS (FAB, Doped with CsI) Found: M+Cs$^+$, 599.1353. C$_{23}$H$_{34}$N$_2$O$_8$ requires M+Cs$^+$599.1369.

Synthesis of Glycopeptide 260 as Illustrated in FIG. 13

Following the coupling procedure described above coupling amino acid 180 with 160 afforded 88% of a pale yellow amorphous foam: $^1$H NMR (400 MHz; CDCl$_3$) 7.33–7.22 (5H, m, aromatic), 6.96 (0.5H, br m, C6NH), 6.89 (0.5H, br m, C6NH), 5.58 (0.5H, br d, C2'NH), 5.55 (0.5H, br d, C2'NH), 5.47 (1H, apparent t, 2×H1), 4.55 (1H, dt, J 7.9 and 2.3, 2×H3), 4.52–4.45 (2H, m, 2×CH$_2$Ph), 4.26 (0.5H, dd, J 5.0 and 2.3, H2), 4.25–4.21 (0.5H, m, H2'), 4.24 (0.5H, dd, J=5.0 and 2.3, H2), 4.16 (1H, dt, J=7.9 and 1.8, 2×H4), 4.14–4.10 (0.5H, m, H2'), 4.09–4.06 (0.5H, m, H3'), 3.95–3.90 (1H, m, 2×H5), 3.87–3.80 (0.5H, m, H3'), 3.70–3.58 (4H, m, 2×H6$_a$H6$_b$+2×C3'OH+2×C5'H$_2$), 3.23 (0.5H, ddd, J=13.9, 8.7 and 4.3, H6$_a$H6$_b$), 3.22 (0.5H, ddd, J=13.9, 9.3 and 4.5, H6$_a$H6$_b$), 2.01–1.66 (2H, m, 2×C4'H$_2$), 1.42 (6H, s, acetonide Me), 1.41 (4.5H, s, $^t$Bu), 1.40 (4.5H, s, $^t$Bu),1.30 (3H, s, acetonide Me), 1.25 (1.5H, s, acetonide Me), 1.23 (1.5H, s, acetonide Me); $^{13}$C NMR (100 MHz; CDCl$_3$) δ 171.00, 170.80, 155.96, 155.63, 137.99, 137.87, 128.48, 128.44, 128.42, 128.38, 128.32, 127.70, 127.65, 109.46, 109.40, 108.78, 108.69, 96.39, 96.28, 79.92, 79.79, 73.24, 73.21, 71.53, 71.44, 70.79, 70.69, 70.46, 70.42, 68.45, 67.49, 65.72, 65.58, 57.66, 57.44, 39.96, 33.51, 31.82, 29.65, 28.29, 25.90, 25.82, 24.93, 24.85, 24.31; IR 3343, 2979, 2933, 1707, 1654, 1497, 1454, 1369, 1254, 1211, 1167, 1110, 1071, 1008, 902, 860, 735, 698 cm$^{-1}$; HRMS (FAB, Doped with CsI) Found M+Cs, 713.2081. C$_{29}$H$_{44}$N$_2$O$_{10}$ requires M+Cs$^+$, 713.2050; Elemental Analysis Found: C, 59.90; H, 7.77; N, 4.74. C$_{29}$H$_{44}$N$_2$O$_{10}$ requires C, 60.00; H, 7.64; N, 4.82.

Deprotection of the BOC group as above gave 260 (85%) as a yellow foam: $^1$H NMR (400 MHz; CDCl$_3$) δ 7.63 (0.5H, br m, C6NH), 7.50 (0.5H, br m, C6NH), 7.34–7.24 (5H, m, aromatic), 5.50 (0.5H, d, J=5.0, H1), 5.49 (0.5H, d, J=5.0, H1), 4.57 (1H, dd, J=7.9 and 2.3, 2×H3), 4.49 (2H, s, 2×OCH$_2$Ph), 4.28 (0.5H, dd, J=5.0 and 2.4, H2), 4.27 (0.5H, dd, J=5.0 and 2.4, H2), 4.17 (1H, dt, J=7.9 and 2.0, 2×H4), 4.06–4.03 (0.5H, m, H3'), 3.95–3.87 (1.5H, m, 2×H5+H3'), 3.75–3.63 (3H, m, 2×H6$_a$H6$_b$+2×C5'H$_2$), 3.32 (0.5H, br d, J=6.3, H2'), 3.30 (0.5H, br d, J=4.4, H2'), 3.24–3.14 (1H, m, 2×H6$_a$H6$_b$), 1.98–1.73 (4H, m, 2×C2'NH$_2$+2×C4'H$_2$), 1.44 (3H, s, acetonide Me), 1.43 (3H, s, acetonide Me), 1.31 (3H; s, acetonide Me), 1.28 (3H, s, acetonide Me); $^{13}$C NMR (63 MHz; CDCl$_3$) δ 173.70,137.81, 128.39, 127.66, 109.35, 108.66, 96.29, 73.31, 72.59, 71.62, 71.29, 70.76, 70.46, 68.12, 66.21, 66.12, 58.45, 39.69, 39.61, 32.24, 25.91, 24.91, 24.27; IR 3362, 2984, 2923, 1654, 1527, 1454, 1382, 1255, 1211, 1167, 1109, 1069, 1006, 901, 859, 739, 698 cm$^{-1}$; HRMS (FAB, Doped with CsI) Found M+H, 481.2573. $C_{24}H_{36}N_2O_8$ requires M+H, 481.2550; Elemental Analysis Found: C, 59.76; H, 7.57; N, 5.60. $C_{24}H_{36}N_2O_8$ requires C, 60.00; H, 7.55; N, 5.83.

Synthesis of Glycopeptide 270 as Illustrated in FIG. 13

Via the procedure described above coupling amino acid 190 with 160, the product was obtained (86%) as a pale yellow amorphous foam: $^1$H NMR (400 MHz; CDCl$_3$) δ 7.33–7.25 (5H, m, aromatic), 6.82 (0.5H, br m, C6NH), 6.64 (0.5H, br m, C6NH), 5.49–5.45 (1H, br s, 2×C2'NH), 5.48 (0.5H, d, J=5.0, H1), 5.47 (0.5H, d, J=5.0, H1), 4.58–4.55 (1H, dm, J=7.9, 2×H3), 4.49 (1H, s, CH$_2$Ph), 4.48 (1H, s, CH$_2$Ph), 4.27 (0.5H, dd, J=5.0 and 2.3, H2), 4.26 (0.5H, dd, J=5.0 and 2.3, H2), 4.17 (1H, dd, J=7.9 and 1.5, 2×H4), 4.12 (0.5H, br d, H2'), 4.09–4.06 (0.5H, m, H2'), 3.98–3.92 (1.5H, m, 2×H5+H3'), 3.78–3.76 (1H, m, 2×C3'OH), 3.69–3.56 (1.5H, m, 2×H6aH6$_b$+H3'), 3.51–3.43 (2H, m, 2×C6'H$_2$), 3.26–3.15 (1H, m, 2×H6$_a$H6$_b$), 1.85–1.49 (4H, m, 2×C4'H$_2$+2×C5'H$_2$), 1.44 (3H, s, acetonide Me), 1.42 (9H, s, 2×$^t$Bu), 1.41 (3H, s, acetonide Me), 1.31 (3H, s, acetonide Me), 1.27 (3H, s, acetonide Me); $^{13}$C NMR (100 MHz; CDCl$_3$) δ 171.63, 171.43, 156.02, 155.69, 138.36, 138.08, 128.40, 128.34, 127.71, 127.63, 127.53, 109.53, 109.42, 108.73, 96.39, 96.31, 79.91, 72.99, 72.86, 71.52, 71.46, 71.29, 70.79, 70.45, 70.26, 70.11, 65.63, 65.50, 57.77, 57.27, 39.98, 30.49, 29.62, 28.28, 26.40, 26.03, 25.92, 24.95, 24.85, 24.30; IR 3345, 2980, 2933, 1707, 1662, 1497, 1454, 1369, 1254, 1167, 1110, 1070, 1007, 918, 902, 859, 736, 698 cm$^{-1}$; HRMS (FAB, Doped with CsI): Found M+Cs, 727.2237. $C_{30}H_{46}N_2O_{10}$ requires M+Cs, 727.2207.

Via the deprotection procedure described afforded 270 (86%) as a yellow foam: $^1$H NMR (400 MHz; CDCl$_3$) δ 7.59 (0.5H, br m, C6NH), 7.44 (0.5H, br m, C6NH), 7.35–7.26 (5H, m, aromatic), 5.49 (1H, d, J=5.0, 2×H1), 4.57 (1H, dd, J=7.9 and 2.3, 2×H3), 4.50 (2H, s, 2×OCH$_2$Ph), 4.30–4.27 (1H, m, 2×H2), 4.19 (1H, d, J 7.9, 2×H4), 4.01–3.98 (0.5H, m, H3'), 3.95–3.89 (1.0H, m, 2×H5), 3.71–3.64 (1.5H, m, 2×H6$_a$H6$_b$+H3'), 3.56–3.49 (2H, m, 2×C6'H$_2$), 3.28–3.18 (1H, m, 2×H6aH6$_b$), 3.24 (0.5H, br d, J=3.6, H2'), 3.21 (0.5H, br d, J=4.5, H2'), 1.85–1.45 (6H, m, 2×C2'NH$_2$+2×C4'H$_2$+2×C5'H$_2$), 1.45 (3H, s, acetonide Me), 1.44 (3H, s, acetonide Me), 1.32 (3H, s, acetonide Me), 1.29 (3H, s, acetonide Me): $^{13}$C NMR (63 MHz; CDCl$_3$) δ 174.71, 174.07, 138.22, 138.13, 128.33, 127.64, 109.35, 108.65, 96.27, 73.21, 72.90, 71.89, 71.62, 70.76, 70.46, 70.23, 66.18, 66.00, 58.79, 58.64, 39.66, 30.04, 29.86, 29.62, 26.36, 25.92, 25.71, 24.89, 24.24; IR 3368, 2987, 2932, 2857, 1657, 1526, 1454, 1383, 1255, 1211, 1167, 1109, 1070, 1007, 919, 902, 736, 698 cm$^{-1}$; HRMS (Doped with CsI): Found M+H, 495.2727. $C_{25}H_{38}N_2O_8$ requires M+H, 495.2706; Elemental Analysis: Found; C, 61.01; H, 8.02; N, 5.36. $C_{25}H_{38}N_2O_8$ requires; C, 60.71; H, 7.74; N, 5.66.

Synthesis of Glycopeptide 280 as Illustrated in FIG. 13

Via the coupling procedure described above coupling amino acid 210 with 160 affording the product (87%) as a colorless oil: [α]$_D$+14 (c. 2.88 in CHCl$_3$); $^1$H NMR (400 MHz; CDCl$_3$) δ 7.33–7.24 (11H, m, 2×aromatics+C6NH), 5.64 (1H, br s, C2'NH), 5.45 (1H, d, J=5.0, H1), 4.55 (1H, dd, J=8.0 and 2.4, H3), 4.53–4.47 (4H, m, 2×OCH$_2$Ph), 4.27 (1H, dd, J=5.0 and 2.4, H2), 4.17 (1H, dd, J=7.9 and 1.7, H4), 3.98–3.95 (2H, br m, 2×CH$_a$H$_b$OBn), 3.91 (1H, ddd, J=8.5, 4.8 and 1.8, H5), 3.88–3.83 (2H, br m, 2×CH$_a$H$_b$OBn), 3.60 (1H, ddd, J=13.7, 7.4 and 4.8, H6$_a$H6$_b$), 3.32 (1H, ddd, J=13.7, 8.5 and 4.5, H$^6$$_a$H$^6$$_b$), 1.43 (3H, s, acetonide Me), 1.42 (3H, s, acetonide Me), 1.40 (9H, s, $^t$Bu), 1.29 (3H, s, acetonide Me), 1.28 (3H, s, acetonide Me); $^{13}$C NMR (100 MHz; CDCl$_3$) δ 171.28, 154.74, 137.74, 137.69, 128.48, 128.42, 128.35, 128.26, 127.67, 127.58, 109.34, 108.69, 96.26, 73.55, 73.47, 71.44, 70.79, 70.53, 70.04, 65.94, 62.07, 39.85, 28.29, 26.05, 25.96, 25.03, 24.43; IR 3380, 2979, 2923, 1715, 1678, 1484, 1454, 1367, 1253, 1211, 1167, 1097, 1070, 1006, 901, 739, 698 cm$^{-1}$; HRMS (FAB, Doped with CsI) Found M+Cs, 789.2385. $C_{35}H_{48}N_2O_{10}$ requires M+Cs, 789.2363; Elemental Analysis Found: C, 64.04; H, 7.58; N, 4.36. $C_{35}H_{48}N_2O_{10}$ requires C, 64.00; H, 7.36; N, 4.26.

Via the deprotection procedure described above, 28 was obtained (66%) as a colorless oil.: [α]$_D$+9.7 (c. 5.7 in CHCl$_3$); $^1$H NMR (400 MHz; CDCl$_3$) δ 8.05–8.01 (1H, m, C6NH), 7.34–7.24 (10H, m, 2×aromatics), 5.47 (1H, d, J=5.0, H1), 4.53 (1H, dd, J=7.9 and 2.4, H3), 4.54–4.44 (4H, m, 2×OCH$_2$Bn), 4.27 (1H, dd, J=5.0 and 2.4, H2), 4.15 (1H, dd, J 7.9 and 1.7, H4), 3.87 (1H, ddd, J 8.6, 4.2 and 1.6, H5), 3.77 (1H, d, J 8.9, CH$_a$H$_b$OBn) 3.64 (1H, d, J 9.0, CH$_a$H$_b$OBn), 3.64–3.58 (1H, m, H6$_a$H6$_b$), 3.53 (LH, d, J 8.8, CH$_a$H$_b$OBn) 3.52 (1H, d, J 9.0, CH$_a$H$_b$OBn) 3.25 (1H, ddd, J 13.8, 8.6 and 4.4, H6$_a$H6$_b$), 1.97 (2H, br s, C2'NH$_2$), 1.43 (3H, s, acetonide Me), 1.38 (3H, s, acetonide Me), 1.30 (3H, s, acetonide Me), 1.28 (3H, s, acetonide Me); $^{13}$C NMR (100 MHz; CDCl$_3$) 175.84, 109.50, 108.76, 96.40, 71.50, 70.81, 70.46, 65.65, 65.43, 61.96, 39.79, 25.89, 25.80, 24.83, 24.24; IR 3378, 2985, 2917, 2861, 1670, 1517, 1453, 1382, 1254, 1211, 1169, 1097, 1070, 1006, 902, 738, 698 cm$^{-1}$; HRMS (FAB, Doped with CsI) Found M+Cs, 689.1818. $C_{30}H_{40}N_2O_8$ requires M+Cs, 689.1839; Elemental Analysis Found: C, 64.57; H, 6.97; N, 4.96. $C_{30}H_{40}N_2O_8$ requires C, 64.73; H, 7.24; N, 5.03.

Synthesis of Glycopeptide 290 as Illustrated in FIG. 13

Via the coupling procedure described above coupling amino acid 240 with 160, the product was obtained (78%) as a pale yellow amorphous foam: $^1$H NMR (400 MHz; CDCl$_3$) δ 7.35–7.25 (5H, m, aromatic), 6.96 (0.5H, br s, C6NH), 6.83 (0.5H, br s, C6NH), 6.41 (0.5H, br s, C2'NH), 5.93 (0.5H, br s, C2'NH), 5.48 (1H, t, J=5.2, 2×H1), 4.57 (0.5H, dd, J=7.9 and 2.4, H3), 4.56 (0.5H, dd, J=7.9 and 2.4, H3), 4.51–4.45 (2H, m, 2×OCH$_2$Ph), 4.28 (0.5H, dd, J=5.0 and 2.4, H2), 4.27 (0.5H, dd, J=5.0 and 2.4, H2), 4.19 (0.5H, dd, J=7.9 and 1.8, H4), 4.16 (0.5H, dd, J=7.9 and 1.7, H4), 4.15–4.10 (1H, m, 2×CH$_a$H$_b$OH), 4.00–3.90 (2.0H, m, 2×H5+2×CH$_a$H$_b$OH), 3.70–3.51 (4H, m, 2×H6$_a$H6$_b$+2×C4'H$_{2+2}$×CH$_2$OH), 3.25–3.18 (1H, m, 2×H6$_a$H6$_b$), 2.31–2.09 (2H, m, 2×C3'H$_2$), 1.45 (1.5H, s, acetonide Me), 1.44 (1.5H, s, acetonide Me), 1.43 (3H, s, acetonide Me), 1.39 (9H, s, 2×$^t$Bu), 1.30 (3H, s, acetonide Me), 1.29 (1.5H, s, acetonide Me), 1.28 (1.5H, s, acetonide Me); $^{13}$C NMR (100 MHz; CDCl$_3$) δ 173.99, 173.09, 155.08, 137.53, 137.48, 128.45, 127.84, 127.73, 109.38, 108.75, 96.35, 80.08, 73.31, 73.27, 71.53, 70.79, 70.48, 66.74, 66.58, 66.48, 65.61, 65.40, 63.26, 62.70, 39.99, 33.55, 32.79, 29.67, 28.40, 28.31, 28.25, 25.97, 24.96, 24.91, 24.31, 24.27; IR 3374, 2979, 2935, 1717, 1667, 1486, 1455, 1369, 1254, 1212, 1167, 1070, 1005, 902, 734, 698 cm$^{-1}$; HRMS (FAB, Doped with CsI) Found M+Cs, 713.2074. $C_{29}H_{44}N_2O_{10}$ requires M+Cs, 713.2050; Elemental Analysis Found: C, 60.26; H, 7.78; N, 4.92. $C_{29}H_{44}N_2O_{10}$ requires C, 60.00; H, 7.64; N, 4.82.

Via the deprotection procedure described above affording 290 (73%) as a yellow foam: $^1$H NMR (400 MHz; CDCl$_3$) δ 8.13 (0.5H, br m, NH), 8.04 (0.5H, br m, NH), 7.34–7.24 (5H, m, aromatic), 5.50 (1H, d, J=5.0, 2×H1), 4.58–4.55

(1H, dm, J=7.9, 2×H3), 4.50 (0.5H, d, J=11.7, OCH$_a$H$_b$Ph), 4.45 (1H, s, OCH$_2$Ph), 4.44 (0.5H, d, J=11.7, OCH$_a$H$_b$Ph), 4.28 (1H, dd, J=5.0 and 2.4, 2×H2), 4.17 (1H, dm, J=7.9, 2×H4), 4.05–4.02 (0.5H, m, H5), 3.91–3.88 (0.5H, m, H5), 3.79 (0.5H, d, J 11.0, CH$_a$H$_b$OH), 3.72 (0.5H, d, J=10.9, CH$_a$H$_b$OH), 3.69–3.55 (3H, m, 2×H6$_a$H6$_b$+2×C4'H$_2$), 3.46 (0.5H, d, J=10.9, CH$_a$H$_b$OH), 3.34 (0.5H, d, J=11.0, CH$_a$H$_b$OH), 3.21 (0.5H, ddd, J=14.1, 9.1 and 4.6, H6$_a$H6$_b$), 3.15 (0.5H, ddd, J 14.0, 9.7 and 4.9, H6$_a$H6$_b$), 2.20–1.60 (2H, br s, C2'NH2), 2.09–2.00 (1H, m, C3'H$_2$), 1.87 (0.5H, ddd, J=14.7, 7.0 and 4.6, H3'$_a$H3'$_b$), 1.79 (0.5H, ddd, J=14.6, 7.4 and 4.5, H3'$_a$H3'$_b$), 1.47 (1.5H, s, acetonide Me), 1.43 (4.5H, s, acetonide Me), 1.31 (3H, s, acetonide Me), 1.28 (3H, s, acetonide Me); $^{13}$C NMR (100 MHz; CDCl$_3$) δ 176.89, 176.71, 138.00, 137.92, 128.40, 128.36, 128.33, 128.30, 127.69, 127.66, 109.46, 109.40, 108.75, 108.63, 96.53, 96.35, 73.21, 73.15, 71.70, 71.54, 70.91, 70.82, 70.47, 69.28, 68.83, 66.90, 66.83, 66.03, 65.10, 60.86, 60.43, 39.79, 39.72, 35.53, 35.37, 25.98, 25.96, 25.93, 25.76, 24.96, 24.87, 24.31; IR 3372, 2973, 2933, 1650, 1522, 1382, 1254, 1211, 1166, 1103, 1069, 1005, 902 cm$^{-1}$; HRMS (FAB, Doped with CsI) Found: Found M+Cs, 613.1550. C$_{24}$H$_{36}$N$_2$O$_8$ requires M+Cs, 613.1526.

Succinic Anhydride Coupling to Form Mimics 2000, 5000, and 8000 as Illustrated in FIG. 14

The coupling reaction of amine 250, 260 or 270 with with succinic anhydride is shown below and is representative of the procedure used for the synthesis of all mimics reacted with succinic anydridride. This procedure was also used for the glutaric derivatives:

Coupling Procedure of Amine 250, 260 or 270 with Succinic Anhydride as Illustrated in FIG. 14 (Coupling Method A)

Succinic anhydride (6.6 mg, 66 μmol) was added to a stirred solution of amino glycopeptide 250, 260 or 270 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product (24.6 mg, 71%) as a white amorphous foam: [α]$_D$+1.8 (c. 2.52 in CHCl$_3$); $^1$H NMR (400 MHz; CD$_3$OD) δ 7.90 (1H, br t, J=5.6, C6NH), 7.38–7.24 (5H, m, aromatic), 5.46 (1H, d, J=5.0, H1), 4.60 (1H, dd, J=7.9 and 2.4, H3), 4.56–4.51 (3H, m, H2'+OCH$_2$Ph), 4.33 (1H, dd, J=5.0 and 2.4, H2), 4.20 (1H, dd, J=7.9 and 1.8, H4), 4.03 (1H, br dd, J=10.2 and 5.2, H3'), 3.94 (1H, ddd, J=8.4, 4.4 and 1.7, H5), 3.62 (1H, dd, J=10.2 and 4.1, H4'$_a$H4'$_b$), 3.58 (1H, dd, J=10.2 and 5.2, H4'$_a$H4'$_b$), 3.47–3.41 (1H, m, H6$_a$H6$_b$), 3.28–3.24 (1H, m, H6$_a$H6$_b$), 2.60–2.46 (4H, m, C2''H$_2$+C3''H$_2$), 1.46 (3H, s, acetonide Me), 1.40 (3H, s, acetonide Me), 1.32 (3H, s, acetonide Me), 1.30 (3H, s, acetonide Me); $^{13}$C NMR (100 MHz; CD$_3$OD) δ 174.54, 172.38, 139.55, 129.39 129.04, 129.00, 128.73, 110.48, 109.99, 97.81, 74.43, 72.65, 72.15, 71.87, 71.33, 67.51, 57.10, 41.06, 40.94, 31.62, 26.41, 26.33, 25.19, 24.57; IR 3304, 2986, 2933, 1721, 1643, 1536, 1453, 1382, 1254, 1211, 1166, 1109, 1069, 1004, 900, 752, 698 cm$^{-1}$; HRMS (FAB, Doped with CsI) Found: M+Cs$^+$, 699.1510. C$_{27}$H$_{38}$N$_2$O$_{11}$ requires M+Cs$^+$ 699.1530.

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P2 (water). The collect fractions were combined and freeze dried to afford the title compound 2000, 5000 or 8000 (5.6 mg, 70%).

Succinic Anhydride Coupling to Form Mimics 3000, 6000, and 9000 as Illustrated in FIG. 14

The coupling reaction of amine 250, 260 or 270 with glutaric anhydride is shown below and is representative of the procedure used for the synthesis of all mimics reacted with glutaric anydridride.

Coupling Procedure of Amine 250, 260 or 270 with Glutaric Anhydride as Illustrated in FIG. 14 (Coupling Method B)

Glutaric anhydride (6.6 mg, 66 μmol; Aldrich) was added to a stirred solution of amino glycopeptide 250, 260 or 270 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product (24.6 mg, 71%) as a white amorphous foam: [α]$_D$+1.8 (c. 2.52 in CHCl$_3$); $^1$H NMR (400 MHz; CD$_3$OD) δ 7.90 (1H, br t, J=5.6, C6NH), 7.38–7.24 (5H, m, aromatic), 5.46 (1H, d, J=5.0, H1), 4.60 (1H, dd, J=7.9 and 2.4, H3), 4.56–4.51 (3H, m, H2'+OCH$_2$Ph), 4.33 (1H, dd, J=5.0 and 2.4, H2), 4.20 (1H, dd, J=7.9 and 1.8, H4), 4.03 (1H, br dd, J=10.2 and 5.2, H3'), 3.94 (1H, ddd, J=8.4, 4.4 and 1.7, H5), 3.62 (1H, dd, J=10.2 and 4.1, H4'$_a$H4'$_b$), 3.58 (1H, dd, J=10.2 and 5.2, H4'$_a$H4'$_b$), 3.47–3.41 (1H, m, H6$_a$H6$_b$), 3.28–3.24 (1H, m, H6$_a$H6$_b$), 2.60–2.46 (4H, m, C2''H$_2$+C3''H$_2$), 1.46 (3H, s, acetonide Me), 1.40 (3H, s, acetonide Me), 1.32 (3H, s, acetonide Me), 1.30 (3H, s, acetonide Me); $^{13}$C NMR (100 MHz; CD$_3$OD) δ 174.54, 172.38, 139.55, 129.39 129.04, 129.00, 128.73, 110.48, 109.99, 97.81, 74.43, 72.65, 72.15, 71.87, 71.33, 67.51, 57.10, 41.06, 40.94, 31.62, 26.41, 26.33, 25.19, 24.57; IR 3304, 2986, 2933, 1721, 1643, 1536, 1453, 1382, 1254, 1211, 1166, 1109, 1069, 1004, 900, 752, 698 cm$^{-1}$; HRMS (FAB, Doped with CsI) Found: M+Cs$^+$, 699.1510. C$_{27}$H$_{38}$N$_2$O$_{11}$ requires M+Cs$^+$ 699.1530.

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 3000, 6000 or 9000 (5.6 mg, 70%).

N-Cbz-γ-Benzyl Ester of Aspartic Acid Coupling to Form Mimics 4000, 7000, and 1000 as Illustrated in FIG. 14

The coupling reaction of amine 250, 260 or 270 with glutaric anhydride is shown below and is representative of the procedure used for the synthesis of all mimics reacted with N-Cbz-γ-benzyl ester of aspartic acid.

Coupling Procedure of Amine 250, 260 or 270 with the N-Cbz-γ-Benzyl Ester of Aspartic Acid as Illustrated in FIG. 14 (Coupling Method C) to Form Mimics 4000, 7000, and 1000

EDCI (14.3 mg, 75 μmol) was added to a stirred solution of 250, 260 or 270 (33.4 mg, 71.5 μmol), N-Cbz-γ-benzyl ester of aspartic acid (26.8 mg, 75 μmol; Aldrich/Sigma), HOBt (10.1 mg, 75 μmol) and 4-methyl morpholine (17 μL, 150 μmol) in dry DMF (2 mL) under argon at −20° C. The resulting mixture was stirred at −20° C. for 1 h and then allowed to warm slowly to 23° C. After 12 h, the reaction solution was quenched 5% w/v citric acid solution (20 mL) and extracted with EtOAc (6×25 mL). The combined organic extracts were washed with saturated NaHCO$_3$ solution (50 mL) and saturated NaCl solution (50 mL), dried (MgSO$_4$) and evaporated down under reduced pressure. The residual oil was then purified by silica gel flash chromatography (40%Æ50%Æ66% EtOAc in hexanes) to give the product (43.2 mg, 75%) as a pale yellow oil: $[\alpha]_D$+2.4 (c. 1.57 in CHCl$_3$); $^1$H NMR (400 MHz; CDCl$_3$) δ 7.56 (1H, br d, J=7.9, C2'NH), 7.35–7.24 (15H, m, aromatic), 6.92–6.90 (1H, br m, C6NH), 5.88 (1H, br d, J=8.7, C2"NH), 5.48 (1H, d, J=5.0, H1), 5.12–5.03 (4H, m, OCH$_2$Ph [ester & Cbz]), 4.60–4.47 (4H, m, H2'+H2"+OCH$_2$Ph [Et2O]), 4.56 (1H, dd, J=7.9 and 2.3, H3), 4.27 (1H, dd, J=5.0 and 2.4, H2), 4.15 (1H, dd, J=7.9 and 1.7, H4), 4.04–4.00 (1H, br m, H3'), 3.90–3.87 (1H, m, H5), 3.70–3.54 (4H, m, H6$_a$H6$_b$+C3'OH+C4'H2), 3.15 (1H, ddd, J=14.0, 9.4 and 4.2, H6$_a$H6$_b$), 3.07 (1H, dd, J=17.2 and 4.5, H3"$_a$H3"$_b$), 2.78 (1H, dd, J=17.2 and 4.5, H3"$_a$H3"$_b$), 1.44 (3H, s, acetonide Me), 1.43 (3H, s, acetonide Me), 1.31 (3H, s, acetonide Me), 1.27 (3H, s, acetonide Me); $^{13}$C NMR (100 MHz; CDCl$_3$) δ 171.68, 170.39, 169.47, 155.99, 137.69, 135.85, 135.22, 138.59, 128.56, 128.43, 128.41, 128.29, 128.25, 127.89, 127.81, 109.47, 108.85, 96.30, 73.42, 71.45, 71.24, 70.76, 70.66, 70.41, 67.39, 66.96, 66.12, 55.45, 51.30, 39.96, 36.26, 25.94, 24.90, 24.31; IR 3304, 2986, 2934, 1729, 1647, 1533, 1498, 1454, 1328, 1255, 1212, 1167, 1109, 1068, 1003, 901, 739, 697 cm$^{-1}$; HRMS (FAB, Doped with CsI) Found: M+Cs$^+$, 938.2453. C$_{42}$H$_{51}$N$_2$O$_{13}$ requires M+Cs$^+$ 938.2476; Elemental Analysis Found: C, 62.35; H, 6.15; N, 4.99. C$_{42}$H$_{51}$N$_2$O$_{13}$ requires C, 62.60; H, 6.38; N, 5.21.

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 4000, 7000 or 1000 (5.6 mg, 70%).

Coupling Procedure of Amine 280 with BnO$_2$C—(CH$_2$)$_2$COCl as Illustrated in FIG. 14 (Coupling Method D) to Provide Mimetic 1100

BnO$_2$C—(CH$_2$)$_2$COCl (6.6 mg, 66 μmol; Aldrich) was added to a stirred solution of amino glycopeptide 280 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product;

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 1100 (5.6 mg, 70%).

Coupling Procedure of Amine 280 with BnO$_2$C—(CH$_2$)$_3$COCl as Illustrated in FIG. 14 (Coupling Method E) to Provide 1200

BnO$_2$C—(CH$_2$)$_3$COCl (6.6 mg, 66 μmol; Aldrich) was added to a stirred solution of amino glycopeptide 280 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product (24.6 mg, 71%) as a white amorphous foam;

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 1200 (5.6 mg, 70%).

Coupling Procedure of Amine 290 with BnO$_2$C—(CH$_2$)$_2$COOH as Illustrated in FIG. 14 (Coupling Method F) to Provide 1300

BnO$_2$C—(CH$_2$)$_2$COOH (6.6 mg, 66 μmol; Aldrich) was added to a stirred solution of amino glycopeptide 290 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product (24.6 mg, 71%) as a white amorphous foam;

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1 CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 1300 (5.6 mg, 70%).

Coupling Procedure of Amine 290 with BnO$_2$C—(CH$_2$)$_3$COOH as Illustrated in FIG. 14 (Coupling Method G) to Provide 1400

BnO$_2$C—(CH$_2$)$_3$COOH (6.6 mg, 66 μmol; Aldrich) was added to a stirred solution of amino glycopeptide 290 (28.8 mg, 56 μmol) in MeOH (2 mL) at 23° C. After 30 min, the solution was evaporated down under reduced pressure. The residual solid was purified by silica gel flash chromatography (2Æ5% acetic acid in EtOAc) to give the product (24.6 mg, 71%) as a white amorphous foam;

A solution of the above glycopeptide (187 mg, 322 μmol) with 90% TFA in water (2 mL) was stirred at 23° C. After 2 hr, the solution was evaporated down under reduced pressure and the residual oil dissolved up in n-BuOH:H$_2$O:MeOH (5:3:2 10 mL). To the solution was added Dowex (Cl$^-$ form, prewashed with MeOH, 100 mg) and the mixture stirred for 30 min, filtered and the solid washed with MeOH (3×5 mL). The combined filtrate and washings were then evaporated down under reduced pressure. The residual oil was purified by silica gel flash chromatography (19:0.9:0.1Æ14:0.9:0.1CH$_2$Cl$_2$:MeOH:NH$_4$OH) to give the benzylated intermediate.

The intermediate (16 mg, 0.015 mmole) was next dissolved in methanol:H$_2$O (2:1, 2 mL), and then a catalytic amount of Pd on carbon was added. Hydrogen was supplied to the reaction system through a balloon. The reaction was completed in 6 h. The mixture was filtered through celite and concentrated in vacuo. The crude product was purified by biogel P$_2$ (water). The collect fractions were combined and freeze dried to afford the title compound 1400 (5.6 mg, 70%).

Resolution of Enantiomerically Pure Alcohol 8000a and 8000b

Compound 270 was resolved by conversion of the secondary alcohol to the chiral camphanate derivative, separation using HPLC, and hydrolysis of the chiral auxiliary using conditions reported exactly as described in Lampe et al *J. Chem. Soc., Perkin Trans.* 1 1992, 2899. Experimental data for selected intermediates is shown below. After resolution the coupling and deprotection sequence is identical to those used for all of the mimics.

Conversion of 270 to 300a. Data for the Camphanate Derivative $^1$H NMR (400 MHz; CDCl$_3$) δ 7.34–7.23 (5H, m, aromatic), 6.56–6.54 (1H, br m, C6NH), 5.46 (1H, d, J=5.0, H1), 5.38 (1H, br d, J=8.4, C2'NH), 5.07–5.04 (1H, br m, H3'), 4.64–4.61 (1H, br m, H2'), 4.57 (1H, dd, J=7.9 and 2.4, H3), 4.46 (2H, s, OCH$_2$Ph), 4.27 (1H, dd, J=5.0 and 2.4, H2), 4.17 (1H, dd, J=7.9 and 1.8, H4), 3.91 (1H, ddd, J=8.1, 4.3 and 1.7, H5), 3.62 (1H, ddd, J=14.0, 7.0 and 4.4, H6$_a$H6$_b$), 3.49–3.40 (2H, m, C6'H$_2$), 3.27 (1H, ddd, J=14.0, 8.2 and 4.4, H6$_a$H6$_b$), 2.39 (1H, ddd, J=13.6, 10.8 and 4.2, Camphanate), 2.05 (1H, ddd, J=13.6, 9.3 and 4.3, Camphanate), 1.88 (1H, ddd, J=13.1, 10.8 and 4.6, Camphanate), 1.80–1.56 (5H, m, C4'H$_2$+C5'H$_2$+Camphanate), 1.44 (3H, s, acetonide Me), 1.43 (3H, s, acetonide Me), 1.41 (9H, s, $^t$Bu), 1.31 (3H, s, acetonide Me), 1.26 (3H, s, acetonide Me), 1.08 (3H, s, Camphanate Me), 1.04 (3H, s, Camphanate Me), 0.96 (3H, s, Camphanate Me); $^{13}$C NMR (100 MHz; CDCl$_3$) δ 178.23, 168.35, 167.66, 155.35, 138.26, 128.36, 127.73, 127.58, 109.49, 108.68, 96.27, 91.13, 80.07, 76.48, 72.97, 71.61, 70.77, 70.49, 69.59, 65.23, 55.65, 54.86, 54.19, 40.20, 30.72, 28.95, 28.28, 25.96, 25.76, 25.69, 24.93, 24.28, 16.55, 16.51, 9.69; IR 3350, 2977, 2934, 1789, 1716, 1673, 1494, 1454, 1369, 1312, 1258, 1211, 1167, 1104, 1069, 1006, 754, 698 cm$^{-1}$; MS (FAB, Doped with CsI) Found: M+Cs$^+$, 907.3033. C$_{40}$H$_{58}$N$_2$O$_{13}$ requires M+Cs$^+$ 907.2993; Found: C, 61.74; H, 7.33; N, 3.48. C$_{40}$H$_{58}$N$_2$O$_{13}$ requires C, 61.99; H, 7.54; N, 3.61.

Data for 300a $^1$H NMR (400 MHz; CDCl$_3$) δ 7.34–7.23 (5H, m, aromatic), 6.63 (1H, br s, C6NH), 5.49–5.47 (1H, br m, C2'NH), 5.48 (1H, d, J=5.0, H1), 4.56 (1H, dd, J 7.9 and 2.4, H3), 4.47 (2H, s, OCH$_2$Ph), 4.27 (1H, dd, J=5.0 and 2.4, H2), 4.17 (1H, dd, J=7.9 and 1.7, H4), 3.98–3.92 (2H, m, H5+H2'), 3.77 (1H, br d, J=5.0, C3'-OH; disappears when shaken with D$_2$O), 3.67 (1H, ddd, J=14.0, 7.5 and 3.7, H6$_a$H6$_b$), 3.60–3.55 (1H, m, H3'; when shaken with D$_2$O gives a ddd, J 8.9, 6.2 and 2.9), 3.52–3.43 (2H, m, C6'H$_2$), 3.17 (1H, ddd, J=14.0, 9.0 and 4.4, H6$_a$H6$_b$), 1.86–1.52 (4H, m, C4'H$_2$+C5'H$_2$), 1.43 (3H, s, acetonide Me), 1.42 (3H, s, acetonide Me), 1.41 (9H, s, $^t$Bu), 1.31 (3H, s, acetonide Me), 1.27 (3H, s, acetonide Me); $^{13}$C NMR (100 MHz; CDCl$_3$) δ 171.62, 155.68, 138.34, 128.35, 127.64, 127.53, 109.52, 108.73, 96.38, 79.95, 77.23, 72.93, 72.86, 71.44, 70.78, 70.41, 70.10, 65.47, 57.78, 39.98, 30.46, 28.28, 26.04, 25.90, 24.85, 24.30; IR 3337, 2979, 2934, 1703, 1657, 1497, 1454, 1368, 1254, 1211, 1167, 1110, 1070, 1006, 902, 737, 698 cm$^{-1}$; MS (FAB, Doped with CsI) Found: M+Cs$^+$, 727.2229. C$_{30}$H$_{46}$N$_2$O$_{10}$ requires M+Cs$^+$ 727.2209; Found: C, 60.24; H, 7.57; N, 4.59. C$_{30}$H$_{46}$N$_2$O$_{10}$ requires C, 60.59; H, 7.80; N, 4.71.

Conversion of 270 to 300b

Data for the Camphanate Derivative $^1$H NMR (400 MHz; CDCl$_3$) δ 7.32–7.22 (5H, m, aromatic), 6.69 (1H, br s, C6NH), 5.58–5.54 (1H, br m, H3'), 5.44 (1H, d, J=5.0, H1), 5.29 (1H, br d, J=9.3, C2'NH), 4.55 (1H, dd, J=7.9 and 2.3, H3), 4.44 (2H, s, OCH$_2$Ph), 4.38 (1H, br dd, J=9.1 and 3.0, H2'), 4.25 (1H, dd, J=5.0 and 2.3, H2), 4.12 (1H, dd, J=7.9 and 1.5, H4), 3.85–3.80 (1H, m, H5), 3.61–3.55 (1H, br m, H6$_a$H6$_b$), 3.45–3.42 (2H, m, C6'H$_2$), 3.15 (1H, ddd, J=13.9, 8.4 and 3.7, H6$_a$H6$_b$), 2.41–2.34 (1H, br m, Camphanate), 1.98–1.84 (2H, m, 2×Camphanate), 1.78–1.57 (5H, m, C4'H₂+C5'H₂+Camphanate), 1.41 (15H, s, ᵗBu+2×acetonide Me), 1.30 (3H, s, acetonide Me), 1.25 (3H, s, acetonide Me), 1.06 (3H, s, Camphanate Me), 1.00 (3H, s, Camphanate Me), 0.87 (3H, s, Camphanate Me); $^{13}$C NMR (100 MHz; CDCl₃) δ 178.34, 169.16, 166.58, 155.57, 138.33, 128.32, 127.61, 127.50, 109.44, 108.70, 96.14, 91.09, 80.55, 74.82, 72.77, 71.64, 70.74, 70.42, 69.42, 65.79, 56.49, 54.86, 54.35, 40.14, 30.88, 28.86, 28.22, 27.66, 25.98, 25.46, 24.95, 24.29, 16.58, 16.36, 9.65; IR 3328, 2977, 2934, 1790, 1753, 1712, 1675, 1516, 1454, 1368, 1309, 1258, 1211, 1167, 1106, 1088, 1006, 753, 698 cm⁻¹; MS (FAB, Doped with CsI) Found: M+Cs⁺, 907.3031. $C_{40}H_{58}N_2O_{13}$ requires M+Cs⁺ 907.2993; Found: C, 61.83; H, 7.34; N, 3.47. $C_{40}H_{58}N_2O_{13}$ requires C, 61.99; H, 7.54; N, 3.61.

Data for 300b $^1$H NMR (400 MHz; CDCl₃) δ 7.35–7.25 (5H, m, aromatic), 6.83–6.80 (1H, br m, C6NH), 5.47 (2H, br d, J=5.0, H1+C2'NH), 4.57 (1H, dd, J=7.9 and 2.4, H3), 4.49 (2H, s, OCH₂Ph), 4.27 (1H, dd, J=5.0 and 2.4, H2), 4.17 (1H, dd, J=7.9 and 1.7, H4), 4.12 (1H, br d m, J=7.7, H2'), 4.09–4.03 (1H, br m, H3'; when shaken with D₂O gives a ddd, J=8.9, 6.2 and 2.9), 3.93 (1H, ddd, J=8.7, 3.8 and 1.6, H5), 3.79 (1H, br s, C3'-OH; disappears when shaken with D₂O), 3.62 (1H, ddd, J 14.0, 7.2 and 4.0, H6ₐH6ᵦ), 3.52–3.49 (2H, m, C6'H₂), 3.22 (1H, ddd, J=14.0, 8.7 and 4.6, H6ₐH6ᵦ), 1.81–1.51 (4H, m, C4'H₂+C5'H₂), 1.44 (6H, s, 2×acetonide Me), 1.42 (9H, s, ᵗBu), 1.31 (3H, s, acetonide Me), 1.27 (3H, s, acetonide Me); $^{13}$C NMR (100 MHz; CDCl₃) δ 171.42, 155.02, 138.05, 128.42, 127.72, 127.65, 109.42, 108.73, 96.38, 79.92, 73.00, 71.51, 71.31, 70.79, 70.45, 70.28, 65.60, 57.25, 39.96, 29.63, 28.28, 26.42, 25.94, 24.96, 24.30; IR 3350, 2979, 2934, 1702, 1661, 1495, 1454, 1368, 1253, 1211, 1167, 1109, 1070, 1007, 901, 735, 697 cm⁻¹; MS (FAB, Doped with CsI) Found: M+Cs⁺, 727.2227. $C_{30}H_{46}N_2O_{10}$ requires M+Cs⁺ 727.2209; Found: C, 60.24; H, 7.72; N, 4.57. $C_{30}H_{46}N_2O_{10}$ requires C, 60.59; H, 7.80; N, 4.71.

General Conditions for Deprotection to Give the Final Mimics

TFA Deprotection

The following procedure is representative of the deprotection sequence used for all of the mimics. A solution of glycopeptide (0.01M solution in 90% TFA in H₂O) was stirred at 23° C. After 3 h, the reaction solution was evaporated down under reduced pressure and azeotroped twice with toluene (2×5 mL). An $^1$H NMR and accurate mass were performed on the crude product to ensure that the isopropylidene moieties were removed and then the crude reaction mixture was taken on to the next step without purification.

Hydrogenation

10% Palladium on carbon (50 mg) was added carefully to a stirred solution of crude glycopeptide in 80% acetic acid in H₂O (5 mL) and hydrogenated (1 atm) at 23° C. After 14 h, the 10% palladium on carbon was filtered through Celite® and the solid washed twice with 80% acetic acid in H₂O (2×5 mL). The combined filtrate and washings were evaporated down under reduced pressure. The crude product was purified by Biogel P2 column, and lyophilization of the fractions containing the compound gave the required compound.

We claim:

1. A compound of the formula:

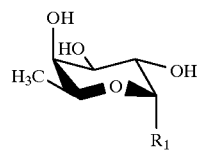

wherein

R₁ is a radical selected from a group represented by one of the following structures:

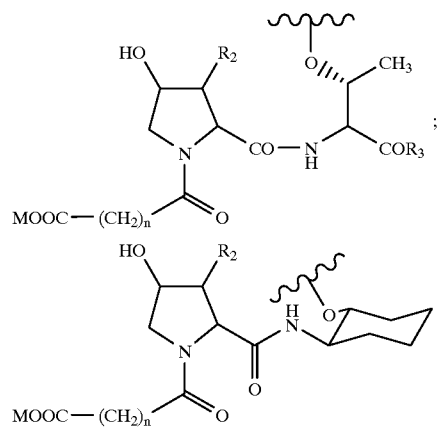

wherein $1 \leq n \leq 5$;

R₂ is a radical selected from the group consisting of H and —OH;

R₃ is a radical selected from the group consisting of —OM, —O—(C₁–C₁₈(alkyl)), —NH(CH₂)ₘCONHR_y, wherein $1 \leq m \leq 5$ and NHR_y wherein R_y is a radical represented by the following structure:

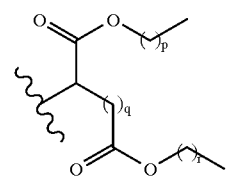

wherein $1 \leq p \leq 20$; $1 \leq q \leq 3$; $1 \leq r \leq 20$; and

M is a counter ion;

with the proviso that the compound cannot be represented by the following structures:

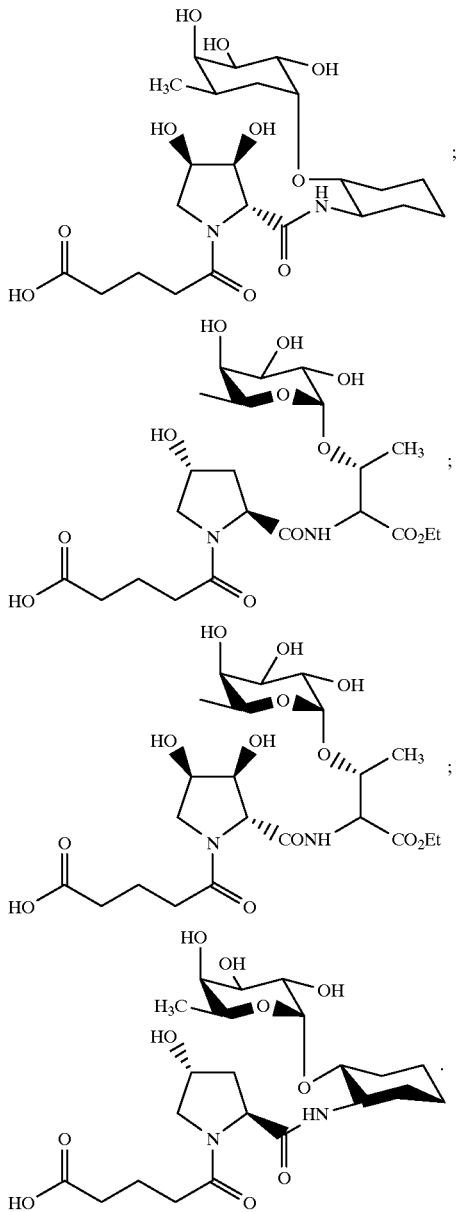

2. A compound as described in claim 1 represented by the following structure:

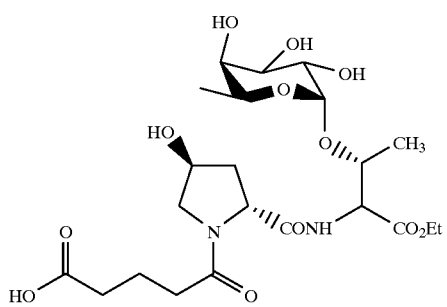

3. A compound as described in claim 1 represented by the following structure:

4. A compound as described in claim 1 represented by the following structure:

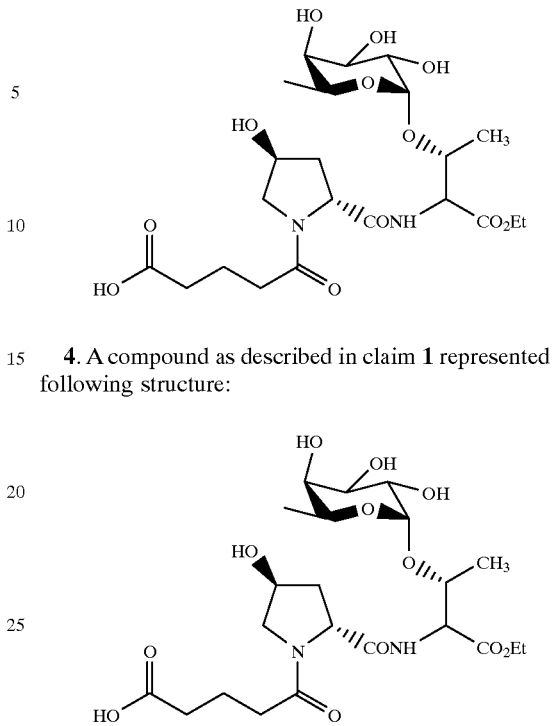

5. A compound as described in claim 1 represented by the following structure:

6. A compound as described in claim 1 represented by the following structure:

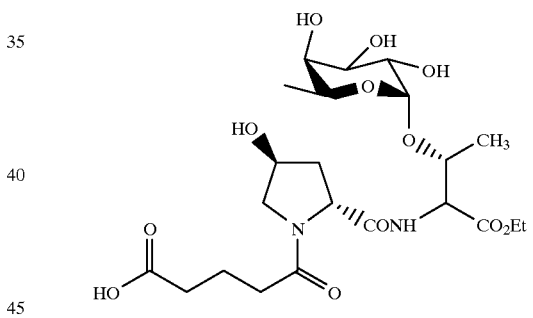

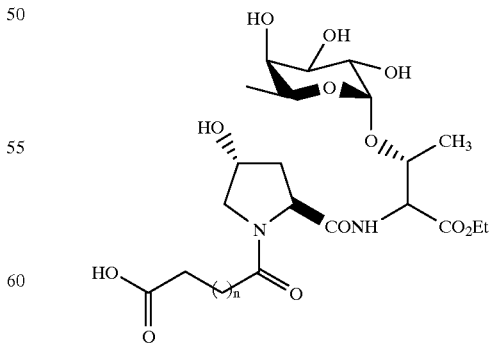

wherein $1 \leq n \leq 4$.

7. A compound as described in claim 1 represented by the following structure:

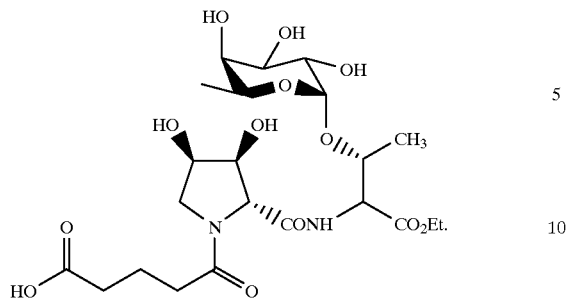
8. A compound as described in claim 1 represented by the following structure:
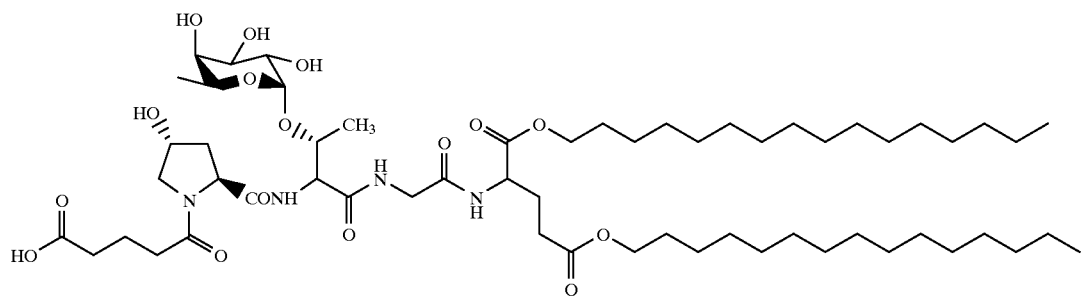
* * * * *